(12) United States Patent
Harvey et al.

(10) Patent No.: US 10,182,561 B2
(45) Date of Patent: *Jan. 22, 2019

(54) METHOD OF USING A TRANSGENIC CHICKEN TO PRODUCE EXOGENOUS PROTEINS IN ITS EGGS

(71) Applicant: ALEXION PHARMACEUTICALS, INC., New Haven, CT (US)

(72) Inventors: Alex J. Harvey, Athens, GA (US); Jeffrey C. Rapp, Athens, GA (US)

(73) Assignee: ALEXION PHARMACEUTICALS, INC., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/181,987

(22) Filed: Jun. 14, 2016

(65) Prior Publication Data

US 2016/0353718 A1 Dec. 8, 2016

Related U.S. Application Data

(60) Continuation of application No. 14/194,010, filed on Feb. 28, 2014, now abandoned, which is a continuation of application No. 13/747,201, filed on Jan. 22, 2013, now abandoned, which is a continuation of application No. 13/179,281, filed on Jul. 8, 2011, now Pat. No. 8,383,399, which is a division of application No. 11/978,360, filed on Oct. 29, 2007, now abandoned, and a continuation-in-part of application No. 11/799,253, filed on May 1, 2007, now abandoned, and a continuation-in-part of application No. 11/699,257, filed on Jan. 26, 2007, now Pat. No. 7,541,512, which is a continuation-in-part of application No. 11/210,165, filed on Aug. 23, 2005, now abandoned.

(60) Provisional application No. 60/930,491, filed on May 16, 2007, provisional application No. 60/994,203, filed on Sep. 18, 2007, provisional application No. 60/640,203, filed on Dec. 29, 2004.

(51) Int. Cl.

| C12P 21/00 | (2006.01) |
|---|---|
| A01K 67/027 | (2006.01) |
| C07K 14/56 | (2006.01) |
| C07K 14/705 | (2006.01) |
| C12N 15/85 | (2006.01) |
| C12N 7/00 | (2006.01) |
| C12N 15/86 | (2006.01) |

(52) U.S. Cl.

CPC ...... *A01K 67/0278* (2013.01); *A01K 67/0275* (2013.01); *C07K 14/56* (2013.01); *C07K 14/70521* (2013.01); *C12N 7/00* (2013.01); *C12N 15/8509* (2013.01); *C12N 15/86* (2013.01); *A01K 2207/15* (2013.01); *A01K 2217/052* (2013.01); *A01K 2227/30* (2013.01); *A01K 2267/01* (2013.01); *C07K 2319/30* (2013.01); *C12N 2015/8518* (2013.01); *C12N 2740/11043* (2013.01); *C12N 2800/24* (2013.01); *C12N 2830/008* (2013.01); *C12N 2830/15* (2013.01); *C12N 2830/90* (2013.01)

(58) Field of Classification Search
USPC ......................................... 800/3, 18, 2, 4, 19
See application file for complete search history.

(56) References Cited

U.S. PATENT DOCUMENTS

| 4,237,224 A | 12/1980 | Cohen et al. |
|---|---|---|
| 4,296,134 A | 10/1981 | Boldt |
| 4,496,537 A | 1/1985 | Kwan et al. |
| 4,603,112 A | 7/1986 | Paoletti et al. |
| 4,722,848 A | 2/1988 | Paoletti et al. |
| 4,769,330 A | 9/1988 | Paoletti et al. |
| 4,903,635 A | 2/1990 | Hebrank |
| 4,959,317 A | 9/1990 | Sauer et al. |
| 4,997,763 A | 3/1991 | Hughes et al. |
| 5,011,780 A | 4/1991 | Perry |
| 5,056,464 A | 10/1991 | Lewis |
| 5,162,215 A | 11/1992 | Bosselman et al. |
| 5,174,993 A | 12/1992 | Paoletti et al. |
| 5,175,384 A | 12/1992 | Krimpendort et al. |
| 5,304,489 A | 4/1994 | Rosen |
| 5,338,683 A | 8/1994 | Paoletti et al. |
| 5,354,674 A | 10/1994 | Hodgson |
| 5,364,783 A | 11/1994 | Ruley et al. |
| 5,367,054 A | 11/1994 | Lee et al. |
| 5,378,618 A | 1/1995 | Sternberg et al. |
| 5,464,764 A | 11/1995 | Capecchi et al. |
| 5,487,992 A | 1/1996 | Capecchi et al. |
| 5,494,807 A | 2/1996 | Paoletti et al. |

(Continued)

FOREIGN PATENT DOCUMENTS

| WO | WO 97/47739 A1 | 12/1997 |
|---|---|---|
| WO | WO 99/19472 A1 | 4/1999 |
| WO | WO 00/11151 A2 | 3/2000 |
| WO | WO 00/56932 A2 | 9/2000 |
| WO | WO 03/081993 A2 | 10/2003 |
| WO | WO 06/120455 A2 | 11/2006 |

OTHER PUBLICATIONS

Yu (PNAS, 1986, vol. 83, p. 3194-3198).*
Flamant (J Gen Virol., Jan. 1993, vol. 74, Pt 1, p. 39-46).*
Bird Classification/Families of the Eastern US Birds, 2009.*
Proudman, 2001, "The quest for transgenic poultry: birds are not mice with feathers" Biotechnology in Animal Husbandry, vol. 5, Kluwer Academic Publishers, p. 283-299; p. 284, lines 1-6.*
Mizuarai (Biochemical and Biophysical Res. Comm. Aug. 24, 2001, vol. 286, p. 456-463).*

(Continued)

*Primary Examiner* — Michael C Wilson
(74) *Attorney, Agent, or Firm* — Mueting, Raasch & Gebhardt, P.A.

(57) ABSTRACT

A transgenic avian containing in its genome an exogenous nucleotide sequence which includes a promoter component and a vector with reduced promoter interference wherein the exogenous nucleotide sequence is integrated into the genome and the avian.

5 Claims, 14 Drawing Sheets

Specification includes a Sequence Listing.

(56) References Cited

U.S. PATENT DOCUMENTS

| | | |
|---|---|---|
| 5,505,941 A | 4/1996 | Paoletti et al. |
| 5,580,859 A | 12/1996 | Felgner et al. |
| 5,589,466 A | 12/1996 | Felgner et al. |
| 5,591,639 A | 1/1997 | Bebbington |
| 5,595,886 A | 1/1997 | Chapman et al. |
| 5,677,177 A | 10/1997 | Wahl et al. |
| 5,714,353 A | 2/1998 | Pathak et al. |
| 5,731,178 A | 3/1998 | Sippel et al. |
| 5,741,957 A | 4/1998 | Deboer et al. |
| 5,784,992 A | 7/1998 | Petitte et al. |
| 5,885,567 A | 3/1999 | Spekellick et al. |
| 5,897,998 A | 4/1999 | Speksnijder et al. |
| 5,879,933 A | 5/1999 | Hodgson |
| 6,027,722 A | 2/2000 | Hodgson |
| 6,069,133 A | 5/2000 | Chiu et al. |
| 6,287,863 B1 | 9/2001 | Hodgson |
| 6,410,220 B1 | 6/2002 | Hodgson et al. |
| 6,825,396 B2* | 11/2004 | MacArthur ........ A01K 67/0275  435/325 |
| 6,875,588 B2* | 4/2005 | Harvey ................. C07K 14/56  435/320.1 |
| 7,294,507 B2* | 11/2007 | Harvey .............. A01K 67/0275  435/320.1 |
| 7,335,761 B2 | 2/2008 | Harvey et al. |
| 7,375,258 B2* | 5/2008 | Harvey ................. C07K 14/56  800/19 |
| 7,511,120 B2 | 3/2009 | Ivarie et al. |
| 7,521,591 B2* | 4/2009 | Ivarie ................ A01K 67/0275  435/320.1 |
| 7,524,626 B2 | 4/2009 | Harvey et al. |
| 7,534,929 B2* | 5/2009 | Ivarie ................. C12N 15/8509  800/19 |
| 7,541,512 B2* | 6/2009 | Rapp .................. A01K 67/0275  800/19 |
| 7,585,963 B2 | 9/2009 | Leavitt et al. |
| 8,507,749 B2* | 8/2013 | Ivarie ................ A01K 67/0275  800/19 |
| 8,519,214 B2* | 8/2013 | Ivarie ................ A01K 67/0275  800/19 |
| 2002/0028488 A1 | 3/2002 | Singh et al. |
| 2003/0039636 A1* | 2/2003 | Leboulch ............... C12N 15/86  424/93.2 |
| 2003/0101472 A1 | 5/2003 | Balitmore et al. |
| 2003/0172387 A1 | 9/2003 | Zhu et al. |
| 2004/0019923 A1 | 1/2004 | Ivarie et al. |
| 2004/0235169 A1 | 11/2004 | Evans et al. |
| 2005/0176047 A1 | 8/2005 | Harvey et al. |
| 2005/0251872 A1 | 11/2005 | Bear et al. |
| 2006/0015960 A1 | 1/2006 | Ivarie et al. |
| 2006/0046248 A1 | 3/2006 | Rapp et al. |
| 2006/0130170 A1 | 6/2006 | Leavitt et al. |
| 2007/0077650 A1 | 4/2007 | Harvey |
| 2007/0113299 A1 | 5/2007 | Harvey et al. |
| 2007/0124829 A1 | 5/2007 | Rapp et al. |
| 2007/0243165 A1 | 10/2007 | Ivarie et al. |

OTHER PUBLICATIONS

Bosselman et al., "Germline transmission of exogenous genes in the chicken" Science, 1989; 243:533-5.
Bosselman et al.,"Replication-Defective Vectors of Reticuloendotheliosis virus transduce exogenous genes" J Virol, 1989; 63:2680-9.
Catterall et al., "The chick ovomucoid gene contains at least six intervening sequences" Nature, 1979; 278:323-7.
Cosset et al. "Improvement of avian leucosis virus (ALV)-based retrovirus vectors by using different cis-acting sequences from ALV's" J of Virol, 1991; 65:3388-94.
Cosset et al., "Use of helper cells with two host ranges to generate high-titer retroviral vectors" Virology, 1993; 193:385-95.
Davis et al., "Single chain antibody (SCA) encoding genes: one-step construction and expression in eukaryotic cells" Biotechnology, 1991; 9:165-9.
Dierich et al., "Cell-specificity of the chicken ovalbumin and conalbumin promoters" EMBO Journal, 1987; 6:2305-2312.
Etches et al., "Contributions to somatic and germ line lineages of chicken blastodermal cells maintained in culture" Mol. Reprod. and Dev, 1996; 45:291-298.
Flamant et al., "Importance of 3' non-coding sequences for the efficient retrovirus-mediated gene transfer in avian cells revealed by self-inactivating vectors" J. Gen. Virol, 1993; 74:39-46.
Gannon et al., "Organization and sequences at the 5' end of a cloned complete ovalbumin gene" Nature, 1979; 276:428-434.
Gibbins, "Gene Constructs for testing transgenic poultry" The Thirty-Seventh Annual National Breeders roundtable, 1988; 1-12.
Ginn et al., "Promoter interference mediated by the U3 region in early-generation HIV-1-derived lentivirus vectors can influence detection of transgenic expression in a cell-type and species-specific manner" Human Gene Therapy, 2003; 14:1127-1137.
Gordon et al., "Production of Human tissue plasminogen activator in transgenic mouse milk" Biotechnology, 1987; 5:1183-1187.
Harvey et al., "Expressions of exogenous protein in the egg white of transgenic chickens" Nature Biotechnology, 2002; 20:396-399.
Harvey et al., "Validating the Hen as a bioreactor for the production of exogenous proteins in egg white" Poultry Science, 2003; 82:49-60.
Ilves et al., "Retroviral vectors designed for targeted expression of RNA polymerase III-driven transcripts: a comparative study" Gene, 1996; 171:203-208.
Jung et al., "Exons encode functional and structural units of chicken lysozyme" PNAS USA, 1980; 77:5759-5763.
Kato et al., "A far upstream estrogen response element of the ovalbumin gene contains several half-palindromic 5'-TGACC-3' motifs acting synergistically" Cell, 1992; 68:731-742.
Kaye et al., "A close association between sites of Dnase I hypersensitivity and sites of enhanced cleavage by micrococcal nuclease in the 5'-flanking region of the actively transcribed ovalbumin gene" EMBO J, 1984; 3:1127-1144.
Lai et al., "The ovalbumin gene: structural sequences in native chicken DNA are not contagious" PNAS USA, 1978; 75:2205-2209.
Love et al., "Transgenic birds by DNA microinjection" Biotech, 1994; 12:60-3.
Nakajima et al., "An improved retroviral vector for assaying promoter activity. Analysis of promoter interference in pIP211 vector" FEBS Letters, 1993; 315:129-33.
Park et al., "Modulation of transcriptional activity of the chicken ovalbumin gene promoter in primary cultures of chicken oviduct cells: effects of putative regulatory elements in the 5'-flanking region" Biochem. Mol. Bioi. Int, 1995; 36:811-816.
Roop et al., "Definition of the 5' and 3' ends of transcripts of the ovalbumin gene" Cell, 1980; 19:63-68.
Royal et al., "The ovalbumin gene region: common features in the organization of three genes expressed in the chicken oviduct under hormonal control" Nature, 1997; 279:324-331.
Sanders et al., "Positive and negative regulatory elements control the steroid-responsive ovalbumin promoter" Biochem, 1988; 27:6550-6557.
Scott et al., "Generation of tissue-specific transgenic birds with lentiviral vectors" PNAS USA, 2005; 102:16443-16447.
Scott et al., "Ovoinhibitor introns specify functional Domains as in the related and linked ovomucoid gene" J Biol Chem, 1987; 26:5899-5907.
Scott et al., "Deoxyribonuclease I sensitivity of the ovomucoid-ovoinhibitor gene complex in oviduct nuclei and relative location of CR1 repetitive sequences" Biochem, 1987; 26:6831-6840.
Shimizu et al., "Analysis of an Approach to oviduct-specific expression of modified chicken lysozyme genes" Biochem. Cell Biol, 2005; 83:49-60.
Shuman, "Production of transgenic birds" Experientia, 1991; 47:897-905.
Stover et al., "Bone-directed expression of Col1a1 prompter-driven self-inactivating retroviral vector in bone marrow cells and transgenic mice" Molecular Therapy, 2001; 3:543-550.
Thoraval et al., "Germ line transmissions of exogenous genes in chickens using helper-free ecotropic avian leucosis virus-based vectors" Transgenic Research, 1995; 4:369-376.

(56) References Cited

OTHER PUBLICATIONS

Vick et al., "Transgenic birds from transformed primordial germ cells" Proc. R. Soc. Land. B, 1993; 33:179-183.
Wilmut et al. "Methods of gene transfer and their potential use to modify milk composition" Theriogenology, 1990; 33:113-123.
Yee et al., "Generation of high-titer pseudotyped retroviral vectors with very broad host range" Methods in Cell Biology, 1994; 43:99-112.
Yu et al., "Self-inactivating retroviral vectors designed for transfer of whole genes into mammalian cells" PNAS, 1986; 83:3194-3198.
Zhu et al., "Production of human monoclonal antibody in eggs of chimeric chickens" Nature Biotechnology, 2005; 23:1159-1169.
Zufferey et al., "Self-inactivating lentivirus vector for safe and efficient in vivo gene delivery" J. Virol, 1998; 72:9873-9880.

\* cited by examiner

```
ctgcagccca ggcagcacac tagagcagag aaatctagtt agcagcaacc actggcagac     60
agaaatgatt atatagatta catactgacc ctagcctctt acactgccta ctgcatcact    120
gaaaggactg ggaagaagag agtgcaataa cgaagctgaa gctaggagga aggcaaggag    180
aactgaagct gactagggaa aaggggggatt aaaggtttaa gtgtctattc catagtttgc    240
tggtttgttt tttgtcaatt cctgaatcag taatttttat gttaattagc aaaaaattac    300
aaacactccc caagtcagga ctgttaccta caacagaagc tcagatcagc tgagccttag    360
tcttttggtc cctccctagg gaatgctgta tgtgtctctc tctccaggcc tgctcaaaat    420
tgacctcaga cccaaacttt tgctgaatct ccagtaccac ctcttttgct cctaactaga    480
taacaaagcc ctgagcgctt tgcttttagc aaagctttaa gtgccattac caactgcacc    540
tggagccttt acctacccct atggacccag gctctatatt taagctctgc cctgaacctt    600
cacttctttc ctgtcctaag ttagatgtac tagtatggtg tgtactatgt ctccagttca    660
aacacagctg tgcccatacc tggccaagga ctcctagtat gacctgggct gtgccttgct    720
gctaaggacc tgctgggtga ttgctggacc tgatcctaat cctgaattaa gaaatgattt    780
cttggcttga ctggatgtgc cctgtggtat gatactgcct tatgatttgg actcttgttt    840
gcagctgtgc aaatccctaa ggagcccagt ctctggccac ctggaatctt gtcactacca    900
aacttcctga gggactggtc ttgctctggg ttctgatctc tggacagtac tcacccttta    960
ctcagcccag gctcccagtt aagccccttt ccaccctgcc aggctctccg ctccatccct   1020
agcaggggct ctcatgacag tgtgaccccc ccttactcag gtcagggcca cttgtgccac   1080
gttcctttcc tgtcttctgt ccctgccttg gctctaaagc agtgtgctac catccacaac   1140
cactgcatct ctctaaagta agcctctcct gagcccaagt ctctgtaacg aggaaggatg   1200
cactttgctc agaaggatgc gaggctgctt ctgagctctg agggcactga cctcccatga   1260
ggtacacccc atacccagga ccacaatcca gcctgctgga accatccaact cctgctggag   1320
taaggccata gcaagaccag catccacctc cctgcagccc tgccctgccc agatattggg   1380
cctgctgatc tcaggatgca gacttgcttc tcagcttgac ctaagcattg ccctgtcttt   1440
atggacccac ctggttagca agttcagtgc agaaggaggc tgttggcatc tagctaattt   1500
tccacccaca ttactgtctg ctgactcatt ctacgtctct cccatcttgt tacaataata   1560
atttgggaga tcatattgaa ggtcttaata aagtcaaggc atgtgatatt ctctgctttg   1620
cctttgtttc tagaataagc cacttcatca tagaagatga aatgctgat cagcagagat    1680
ctgtgcttga taaatccatg ctggctttc ctatcacctt atattccttc atatgccttg   1740
agacacccaa ggaggccttg gatcagagct gtctgtagca gtcctaactg gtatacaatt   1800
agttgtacaa caggtagtga tccgtacaat agttgccgtg agaaagtggg cctgtgctgt   1860
gtcaagcata gagtttgggt tccagtcctg ttctgcatgg cacatatgcc tgagcagctg   1920
ggtaatctct gcattccaat tggaaggcag gggcctgtag gcagttccca cttggcatgg   1980
gtgattgtac cacctgtgtc ctcatctgtg aagcatcatg tttttcattca aatatccttt   2040
tgtttgacag tagaaatgaa cagaattgtt tttttttcct aagcaaattc tgcaagagct   2100
ctgaagaaca aggtgtcagt gaacttctag ctccatagat aggacttgca tcacatgtca   2160
tgccttgatt ggaggtctat ccgatactga acaacttgtg gttccctgag ggaatgtaag   2220
attactgata ctactctctc tttatgttag ctacaataaa tggtaggtta agcaatagat   2280
acagagtttg agtgcctttc ttacaagcat catagtgaac aaatccactg gtgatctacc   2340
ttttcaataa ctacagaaa ttgtaatctc ttggattctc ctccttcccc gttctgaaaa   2400
tgtgttcttt ttttccaaat cagaaccttc cctcaaccac cctgactact ctttggacat   2460
tgttttgttc ttgctcctaa ataggcttta taattttgtt aagtgaaagg ctttgcatgc   2520
aggtgaggct acaactcatt cagtaacaat gaggaagact gtcagatttt ggggaaaatt   2580
ctcccaccca accttttgct agccagtaag atgtaatcac tgaatgtcat gccacaaaga   2640
ccataccaac atcagaccac atatctacag gaagctttaa ggaatcattg actgtacagt   2700
gaagggtaaa tcaaattaaa atgaatgtga ggtctgatac gagatatcct catgggaatc   2760
aagagcaaag acaaatagtt tttcacagtc ttgtcatgat ctgtcacaga ccaaggcagc   2820
acagcaggca acaatgttgg tctcttcaga atggcacagc accgctgcag aaaaatgcca   2880
ggtggactat gaactcacat ccaaggagc ttgacctgat acctgatttt cttcaaacag   2940
gggaaacaac acatcccaac aaaatcccac agagaagaaac catcactgat ggctacagca   3000
ccaaggtatg caatggcaat ccattcgaca ttcatctgtg acctgagcaa aatgatttat   3060
ctctccatga atggttgctt ctttccctca tgaaaaggca atttccacac tcacaatatg   3120
caacaaagac aaacagagaa caattaatgt gctccttcct aatgtcaaaa ttgtagtggc   3180
aaagaggaga acaaaatctc aagttctgag taggttttag tgattggata gaggcttg    3240
acctgtgagc tcacctggac ttcatatcct tttggataaa agtgctttt ataactttca   3300
ggtctccgag tctttattca tgagactgtt ggtttaggga cagacccaca atgaaatgcc   3360
tggcatagga aagggcagca gagccttagc tgaccttttc tgggacaag cattgtcaaa    3420
caatgtgtga caaaactatt tgtactgctt tgcacagctg tgctgggcag ggcaatccat   3480
tgccacctat cccaggtaac cttcaactg caagaagatt gttgcttact ctctctagac    3540
cccaagtca aaccaactat gcaggtatgc tgacaagca atgatgacag cctgttctga    3600
tcaagatctc atttgttcat ggacaatttt tgttgcttgc agctggtctt ccattgggaa   3660
agagtgtagt atatccttct catctgacag aaaagcagaa attctcatgc tccacactta   3720
atctacattg ttttaaacca ccagctactt cttggagagg aaaaatggct tttataagac   3780
tcacaaaaca aagctctgca agtcaaatgc atacaaaact gttctgtagg tctggaatca   3840
```

FIG. 8a

```
ggacactatg tggaagtcaa atagagaagc tttaaaaaaa cctttgggat cattctcatc   3900
ttatatttgc agcacgatac tatgacagtg ataactgaca taactgcatc aatttccttg   3960
atattttatt tgtcttaaag tacaagacat agagatggac gtaaagatgg acatatgact   4020
caggtctgga caggtccgtg gtccatgtat gataaaagag atgaagggaa ggagaatgga   4080
gactgtctaa gaagggcttc agggacgttc tgaaggcaga tttgactgaa tcagatgtac   4140
tgtccaagtc tcatatgtag caatggaaga ctgatattgg agaaatataa agaaatggct   4200
gtgaactcaa agtgaccctg aacagaaaag ggatatggag ttaaaataat ggcacagaac   4260
tgaggtttat atgatatacc atgggctgca gagggtcaga gtgctccacc atgggcctct   4320
cttgggctgc agggaacttc tgttctacac ctggaacacc tcctgccctc ctccgcactg   4380
acctcagtgt catcagggct gtttctctca cattttctca ctcacctctc ccaactacca   4440
ttgtacagca gttgttctta catcttgctc ctcctgaggt gcatctagca tcgatcactg   4500
gctcagctct ggccagtggc agctccctt tgaggacacg ggacagctgc tgggctctgt    4560
tcacagaggc cactccagca gacctccact accacaactt gtagtgtaaa tccactacaa   4620
ctttctgagc tacagaaatg aaatggagac cctctctgct atgggataca aagaggaaa    4680
cgtggcgttt agtgctctgg ctcactggta cacccaacca cagggtgaga agcagcctgt   4740
tgttattcac tactcttagg acagattatg gtgaattgtt aataaaagca tttcttcata   4800
acatccaaag gaggaaatac actaaattat attttttatt tattaattac acatgcttaa   4860
ttatatatgg catggttgct ttgaagaaac cttgtcctta ctgaccagat ctgctgtttg   4920
ctgagacaaa atggctgaca attttggcca tggtggatac cttccccctt tctgtagca    4980
ttaggacaga agttattctg gagcctgtct gacaagtcag acttgataac tttaagtatt   5040
tggaagtgtg cttttcatgc tggatgtcat ctccagaacc tccctgtctg gtaagcagtt   5100
ccctgcctta gtaagagccg aaacggtctc tcttttcctt gttatctcac caggatatta   5160
caatgtgaca ggactatctg aactacgcca acctgcaaat tccaaatata tatatatata   5220
tgtaagatat ctatacacaa attattagtg tttgattgac accagatgac agagaagtgc   5280
atctgagaaa acctattccc aatctccctt ctctttctgc agactgacat gcattttcata  5340
ggtagagata acatttactg ggaagcacat ctatcatcat aaaaagcagg caagattttc   5400
agactttctt agtggctgaa atagaagcaa aagacgtgat taaaaacaaa atgaaacaaa   5460
aaaaatcagt tgatacctgt ggtgtagaca tccagcaaaa aaatattatt tgcactacca   5520
tcttgtctta agtcctcaga cttggcaagg agaatgtaga tttctacagt atatatgttt   5580
tcacaaaagg aaggagagaa acaaaagaaa atggcactga ctaaacttca gctagtggta   5640
taggaaagta attctgctta acagagattg cagtgatctc tatgtatgtc ctgaagaatt   5700
atgttgtact ttttttcccc atttttaaat caaacagtgc tttacagagg tcagaatggt   5760
ttctttactg tttgtcaatt ctattatttc aatacagaac aatagcttct ataactgaaa   5820
tatatttgct attgtatatt atgattgtcc ctcgaaccat gaacactcct ccagctgaat   5880
ttcacaattc ctctgtcatc tgccaggcca ttaagttatt catggaagat ctttgaggaa   5940
cactgcaagt tcatatcata aacacatttg aaattgagta ttgttttgca ttgtatgag    6000
ctatgttttg ctgtatcctc agaaaaaaag tttgttataa agcattcaca cccataaaaa   6060
gatagattta aatattccag ctataggaaa gaaagtgcgt ctgctcttca ctctagtctc   6120
agttggctcc ttcacatgca tgcttcttta tttctcctat tttgtcaaga aaataatagg   6180
tcacgtcttg ttctcactta tgtcctgcct agcatggctc agatgcacgt tgtagataca   6240
agaaggatca aatgaaacag acttctggtc tgttactaca accatagtaa taagcacact   6300
aactaataat tgctaattat gttttccatc tctaaggttc ccacattttt ctgtttttctt  6360
aaagatccca ttatctggtt gtaactgaag ctcaatggaa catgagcaat atttcccagt   6420
cttctctccc atccaacagt cctgatggat tagcagaaca ggcagaaaac acattgttac   6480
ccagaattaa aaactaatat ttgctctcca ttcaatccaa aatggaccta ttgaaactaa   6540
aatctaaccc aatcccatta aatgatttct atggcgtcaa aggtcaaact tctgaaggga   6600
acctgtgggt gggtcacaat tcaggctata tattccccag ggctcagcca gtgtctgtac   6660
atacagctag aaagctgtat tgcctttagc agtcaagctc gaaaggtaag caactctctg   6720
gaattacctt ctctctatat tagctcttac ttgcacctaa actttaaaaa attaacaatt   6780
attgtgctat tgttgtatc tttaagggtg aagtacctgc gtgataccc ctataaaaac     6840
ttctcacctg tgtatgcatt ctgcactatt ttattatgtg taaaagcttt gtgtttgttt   6900
tcaggagct tattctttgt gcttaaaata tgttttaat ttcagaacat cttatcctgt     6960
cgttcactat ctgatatgct ttgcagtttg cttgattaac ttctagccct acagagtgca   7020
cagagagcaa aatcatggtg ttcagtgaat ctgggggagt tattttaatg tgaaaattct   7080
ctagaagttt aattcctgca aagtgcagct gctgatcact acacaagata aaatgtggg    7140
gggtgcataa acgtatatct ttacaataat agatacatgt gaacttatat acagaaaaga   7200
aaatgagaaa aatgtgtgtg tgtatactca cacacgtggt cagtaaaaac ttttgagggg   7260
tttaatacag aaaatccaat cctgaggccc cagcactcag tacgcatata aagggctggg   7320
ctctgaagga cttctgactt tcacagatta tataaatctc aggaaagcaa ctagattcat   7380
gctggctcca aaagctgtgc tttatataag cacactggct atacaatagt tgtacagttc   7440
agctctttat aatagaaaca gacagaacaa gtataaatct tctattggtc tatgtcatga   7500
acaagaattc attcagtggc tctgttttat agtaaacatt gctatttat catgtctgca    7560
tttctcttct gtctgaatgt caccactaaa atttaactcc acagaaagtt tatactacag   7620
tacacatgca tatctttgag caaagcaaac catacctgaa agtgcaatag agcagaatat   7680
```

FIG. 8b

```
gaattacatg cgtgtctttc tcctagacta catgacccca tataaattac attacttatc  7740
tattctgcca tcaccaaaac aaaggtaaaa atacttttga agatctactc atagcaagta  7800
gtgtgcaaca aacagatatt tctctacatt tattttttagg gaataaaaat aagaaataaa  7860
atagtcagca agcctctgct ttctcatata tctgtccaaa cctaaagttt actgaaattt  7920
gctctttgaa tttccagttt tgcaagccta tcagattgtg ttttaatcag aggtactgaa  7980
aagtatcaat gaattctagc tttcactgaa caaaaatatg tagaggcaac tggcttctgg  8040
gacagtttgc tacccaaaag acaactgaat gcaaatacat aaatagattt atgaatatgg  8100
ttttgaacat gcacatgaga ggtggatata gcaacagaca cattaccaca gaattacttt  8160
aaaactactt gttaacattt aattgcctaa aaactgctcg taatttactg ttgtagccta  8220
ccatagagta ccctgcatgg tactatgtac agcattccat ccttacattt tcactgttct  8280
gctgtttgct ctagacaact cagagttcac catgggctcc atcggtgcag caagcatgga  8340
attttgtttt gatgtattca aggagctcaa agtccaccat gccatgaga acatcttcta  8400
ctgccccatt gccatcatgt cagctctagc catggtatac ctgggtgcaa aagacagcac  8460
caggacacaa ataataagg tgagcctaca gttaaagatt aaaacctttg ccctgctcaa  8520
tggagccaca gcacttaatt gtatgataat gtccttgga aactgcatag ctcagaggct  8580
gaaaatctga aaccagagtt atctaaaagt gtggccacct ccaactccca gagtgttacc  8640
caaatgcact agctagaaat cttgaaactg gattgcataa cttcttttg tcataaccat  8700
tatttcagct actattattt tcaattacag gttgttcgct ttgataaact tccaggattc  8760
ggagacagta ttgaagctca ggtacagaaa taatttcacc tccttctcta tgtcccttc  8820
ctctggaagc aaaatacaga agatgaagca atctcttagc tgttccaagc cctctctgat  8880
gagcagctag tgctctgcat ccagcagttg ggagaacact gttcataaga acagagaaaa  8940
agaaggaagt aacagggat tcagaacaaa cagaagataa aactcaggac aaaaataccg  9000
tgtgaatgag gaaacttgtg gatatttgta cgcttaagca agacagctag atgattctgg  9060
ataaatgggt ctggttggaa aagaaggaaa gcctggctga tctgctggag ctagattatt  9120
gcagcaggta ggcaggagtt ccctagagaa aagtatgagg gaattacaga agaaaaacag  9180
cacaaaattg taaatattgg aaaaggacca catcagtgta gttactagca gtaagacaga  9240
caggatgaaa aatagttttg taaacagaag tatctaacta ctttactctg ttcatacact  9300
acgtaaaact tactaagtaa taaaactaga ataacaacat ctttctttct ctttgtattc  9360
agtgtggcac atctgtaaac gttcactctt cacttagaga catcctcaac caaatcacca  9420
aaccaaatga tgtttattcg ttcagccttg ccagtgactt ttatgctgaa gagagatacc  9480
caatcctgcc agtaagttgc tctaaaatct gatctgagtg tattccatgc caaagctcta  9540
ccattctgta atgcaaaaac agtcagagtt ccacatgttt cactaagaaa atttcttttt  9600
ctcttgtttt tacaaatgaa agagaggaca aataacattt ctctatcacc gacctgaaac  9660
tctacagtct tcagagaatg aatggcttgc taaaagaatg tcaaatctta ctatacagct  9720
atttcatatt acactactaa atacactata aggcatagca tgtagtaata cagtgtaaaa  9780
tagcttttta cactactata ttattaatat ctgttaattc cagtcttgca tttcacattt  9840
gcaaaacgtt ttgaaattcg tatctgaaag ctgaatactc ttgctttaca ggaatacttg  9900
cagtgtgtga aggaactgta tagaggaggc ttggaaccta tcaactttca aacagctgca  9960
gatcaagcca gagagctcat caattcctgg gtagaaagtc agacaaatgg taaggtagaa  10020
catgctttgt acatagtgag agttggttca ccctaatact gagaacttgg atatagctca  10080
gccagcgtgc tttgcgttca agcttaccag agctgttgta tgcctgttaa gcagggcata  10140
cagtcatgag gctcttgaaa aatcttaaca gacaaagggc aatgaaaat cggagttaag  10200
ggatggtagg gataaaatgc atagaaagag gtaccacaat tttgatttt gccctaatgc  10260
ctctctgcgt ggttcctcaa ttttttctact tcattcctca tctcctcaga gcattccttt  10320
ccctcatgct tgaaacacag atgaaagact gtgaattcta actgagatga aaacatccac  10380
aaccacacaa cctctggtgt ggagtcacat tctgtgaagg caaaaactag gccacgtaat  10440
ctatgcgtgc aagctacgcg taagctatgt gtgtgacagg acaatgtgag gaacatacta  10500
tgtgcacaag gactgcagaa taaacaggag caaagttttt gaagaaaaca gagtaaaatc  10560
ctgttttcct cttttgttac attctttaca tatatctcaa atttcctctt tggttagaag  10620
caagtaatat ttatgttct tggtactgtt tgggttgaag accattctgg gataagagaa  10680
attcagtgg ttcttcccct aatcataaaa tgtcaggttt agttttttttg taacacgaa  10740
atctcttcat cttttatctt ttgttgtgat tcttgataga gagagaaaca agacttactg  10800
acaatagcag caagaaaatc aatcttggaa gaacaagatt gcaattgcaa aaacaaacca  10860
atgtccttgc ccctacatcc tcttccccat aaattctaca ttctctatct accttgtgct  10920
tgccaacatg atatacgtaa actctctttt cctattcatt cttaaaggaa ttatcagaaa  10980
tgtccttcag ccaagctccg tggattctca aactgcaatg gttctggtta atgccattgt  11040
cttcaaagga ctgtgggaga aagcatttaa ggatgaagac acacaagcaa tgcctttcag  11100
agtgactgag gtatatgggc ataccttaga gatgtaatct agaatttatg aagagagtag  11160
acatgttgtt atatgaacac tgcattagcg tatctgctca tttgtctgca tctctttcag  11220
acactgtgtt aaaagcaggg aatttccctt atgtctctct cgtcacaata ttcctgacat  11280
tgcaaagctc ctgagaaata acttcagatt ccactttcc taggaaggct tctggatgag  11340
aactaatcat cttaactgta actagaacatt tctgcatcca agaataatct ttgttaaaac  11400
tatattctct ctctcttttt ttttttttt tggttctcca gcaagaaagc aaacctgtgc  11460
agatgatgta ccagattggt ttatttagag tggcatcaat ggcttctgag aaaatgaaga  11520
```

FIG. 8c

```
tcctggagct tccatttgcc agtgggacaa tgagcatgtt ggtgctgttg cctgatgaag   11580
tctcaggcct tgagcaggta tggccctaga agttggcttc agaatattaa aaacacatgg   11640
aaatttagct gttgtaaagc tcttttcaac acagttatcc taaaacattt aaccagcaca   11700
aatttcatca tgattcaata tgtgattgtt gcatagaagt gtagatttgt cccactgggt   11760
cctgcaatag cccatgctga gcatggcttg ctgaaagaac tgctttagag ggtgaaaagt   11820
ttgacacagc agacaagatg attctcacct aagcagctgt tactgtagtg gcttgaactc   11880
taaaggtctt gtatctccat tcctgtgcac tgaggagctt cttggaaagt tcatataagg   11940
tttactagtt ctaactatta tctcattcgg tggcactcaa tgtgctttgt tcacgtcttc   12000
ataaattaat ctatctaaaa attggatgtg gttaaagcaa tttcagaaat aacatgtaca   12060
taatgtacaa ttattgatat gaacagaaca caggcatagc atattgtaat taggaggact   12120
gtagttattt tgaataggaa acacaatgta ataaatgaga attcattgaa atgttagtat   12180
gctaactcaa tctaaattat aaagataaag aggcatttaa tcacagctag atttccatca   12240
cttgtgacag acaggcatat gaatgattat gtacagctct aggaaaaaaa gtatgtagga   12300
aaactagtac attttgatta gaaagtctga aaatgaggtg cctgatcaa agagaatacg   12360
tgtgtttgag aaaaaaaaag tttggataga ggtggtaaga gagaatatat tgaaatggtg   12420
tttctacaaa ctgccatggc cagatttgtg taagagacat tcagtaagta ggcaaggaaa   12480
gaaatattac taggtacaaa gcaacatcag taataccaaa agaaaccaat tattccagat   12540
gccaatctcg taataggggtt aagagatttc caccccctca gtggtcacca gtgcaaccag   12600
taactttgct aatttacatt ttcttttttt aaatggcaga tatagctttg aactgagtga   12660
tcatgaactg gtactgtgta atagatgaag acatacttga cgactaaact tctgattttt   12720
aaaaactcaa attctcttga aagatcagtt cccagtctag taacagctga tagtttaagt   12780
atcagtaatt ggctaccatt aacaactggc tcctgagagg tcttaaatgt agagacagct   12840
ttaaactcaa aagcacagag tgattttttag aatagatttc ccaagcaaag aaaataaaca   12900
gggaggagct ttaagggagt agccatctca ttattattat tatttaaaga aatggcagca   12960
agcctacaaa agaaaaataa gacagagcag agaagaaaga gtcatggtat gcttttctat   13020
cttagcaaaa ttaatctcta catgcctagg aaaaagccat gacaagagca atcagttcaa   13080
aaggtgtatg caaaaaacca cataatagta actagtactg cattgccagg aaggaagtta   13140
tgtcgccatt ccatggatct cattctcatt tccttgcagc ttgagagtat aatcaacttt   13200
gaaaaactga ctgaatggac cagttctaat gttatggaag agaggaagat caaagtgtac   13260
ttacctcgca tgaagatgga ggaaaaatac aacctcacat ctgtcttaat ggctatgggc   13320
attactgacg tgtttagctc ttcagccaat ctgtctggca tctcctcagc agagagcctg   13380
aagatatctc aagctgtcca tgcagcacat gcagaaatca atgaagcagg cagagaggtg   13440
gtagggtcag cagaggctgg agtggatgct gcaagcgtct ctgaagaatt tagggctgac   13500
catccattcc tcttctgtat caagcacatc gcaaccaacg ccgttctctt ctttggcaga   13560
tgtgtttccc cttaaaaaga agaaagctga aaaactctgt cccttccaac aagacccaga   13620
gcactgtagt atcaggggta aaatgaaaag tatgttatct gctgcatcca gacttcataa   13680
aagctggagc ttaatctaga aaaaaaatca gaaagaaatt acactgctgag aacaggtgca   13740
attcactttt cctttacaca gagtaatact ggtaactcat ggatgaaggc ttaagggaat   13800
gaaattggac tcacagtact gagtcatcac actgaaaaat gcaacctgat acatcagcag   13860
aaggtttatg ggggaaaaat gcagccttcc aattaagcca gatatctgta tgaccaagct   13920
gctccagaat tagtcactca aaatctctca gattaaatta tcaactgtca ccaaccattc   13980
ctatgctgac aaggcaattg cttgttctct gtgttcctga tactacaagg ctcttcctga   14040
cttcctaaag atgcattata aaaatcttat aattcacatt tctccctaaa ctttgactca   14100
atcatggtat gttggcaaat atggtatatt actattcaaa ttgttttcct tgtacccata   14160
tgtaatgggt cttgtgaatg tgctcttttag ttccttaat cataataaaa acatgtttaa   14220
gcaaacactt ttcacttgta gtatttgaag tacagcaagg ttgtgtagca gggaaagaat   14280
gacatgcaga ggaataagta tggacacaca ggctagcagc gactgtagaa caagtactag   14340
tgggtgagaa gttgaacaag agtcccctac aagcaactta atctaataag ctagtggtct   14400
acatcagcta aaagagcata gtgagggatg aaattggttc tccttctaaa gcatcacctg   14460
ggacaactca tctggagcag tgtgtccaat ctgccgctgc cctgatctcg gctggggtga   14520
tgggacagac cttggctgcc actgagacat ctgagacact gagatctgtc tcaactcaga   14580
tttacccaag aacagctcat tgccaacaga acaaaatctc aaacttatgg ctagtgatga   14640
cagcagtcag ttgtcccatc tgtgacccac caaggctggc atgctggaat gagcaggctt   14700
tggtggcatg tagttactgg acagcaccac tgacatggca agggaaaaa ctgagcatgg   14760
tgtaaatcac tgcctcaaag ccactctct gtgcctgcac catgcttgaa agctcttcta   14820
caggagctgg gtttgttcaa gaaagcttct gtttctccca tctgcttctt gtaccttcac   14880
agggacagag ttagaagggt acagccatgg ctggaagggg ctgactttca aatgtgccta   14940
attttcccttt ggttgctgct gcagctgcag aagaagggt tcagaagcca agagctttga   15000
gataaggatg cctaacctat gttgaagaca tttgtgctga cacctcaggc cccaggatag   15060
gacaactgct ggattgtggc taacccacta gctacagaac ctaatttata ttaccagatt   15120
aggaagagca aaagaacatg tatttataac aggaggtctt ctgtgcttct ctactaaaag   15180
gtgctgtgaa ggagcccaca gtgcagcagt gtatgaggcc tgaaagaggc cgcagcacac   15240
gaagagccct ggtaggagca gcacacagag gggcaggagg gctggggaa ctgccaccca   15300
tggggaccctg tgtgaagcag tgcactcctg agggtggac tgcgtgggaa aggaaaagaa   15360
```

FIG. 8d

```
agcaaacaga cctgtgatga actgtcacac agactgcaga gtgacagagg agggcacgag   15420
gcagtgcgcc cactgcaggg agtggcgctc cttcctcaca gcagcgctaa cagcttggca   15480
ccaatattca gtagtctgtg gtgatacttt ttccagtttc accacacagc atttcgcttg   15540
ttctacttgt tttagctttc cccctccaca agataacaca tactttgcca gtcagtccct   15600
aagaccttaa cttaacagtt agcaaacagg atcttgcaaa agaaggaaga taacatgaca   15660
ccaccttcac tggtgtataa atagttcaaa tactttcctt cactttcccg taaattagtt   15720
gattgcaggt caggagataa caggggaact tactgcaaga gagaaaatga tgtttaatat   15780
tgtcttggac tttctggtgg tctgggcatg aaaatggggt actcaaaatc ctcgggacgt   15840
ttattttca cctgatttat tcccaaactg cactatttct aggccattgg agttcttatc    15900
aattaaatta tactttggct ctctgctatc tcactccctt tcatcttcag catcactttc   15960
agcacaatta caggagaaga cttagactca gagctttagg actcatcata agaggctttc   16020
attgctctgt caccacaccc catatagatc t                                  16051
```

FIG. 8e

AATTGAGGAGCTTTGTTCCTTGGGTTCTTGGGAGCAGCAGGAAGCACTATGGGCGCAGC
GTCAATGACGCTGACGGTACAGGCCAGACAATTATTGTCTGGTATAGTGCAGCAGCAGA
ACAATTTGCTGAGGGCTATTGAGGCGCAACAGCATCTGTTGCAACTCACAGTCTGGGGC
ATCAAGCAGCTCCAGGCAAGAATCCTGGCTGTGGAAAGATACCTAAAGGATCAACAGCT
CCTGGTAC

FIG. 9a

AATGTGGGGAGGGCAAGGCTTGCGAATCGGGTTGTAACGGGCAAGGCTTGACTGAGGGG
ACAATAGCATGTTTAGGCGAAAAGCGGGGCTTCGGTTGTACGCGGTTAGGAGTCCCCTC
AGGATATAGTAGTTTCGCTTTTGCATAGGGAGGGGAAAT

FIG. 9b

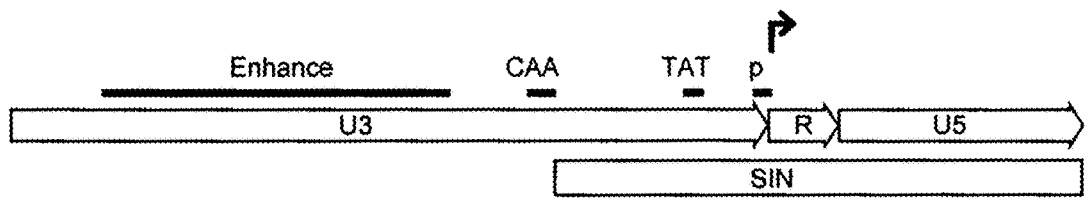

FIG. 10 a

```
AATGTAGTCTTATGCAATACTCTTGTAGTCTTGCAACATGCTTATGTAACGATGAGTTAG      60
CAACATGCCTTATAAGGAGAGAAAAAGCACCGTGCATGCCGATTGGTGGGAGTAAGGTGG     120
TATGATCGTGGTATGATCGTGCCTTGTTAGGAAGGCAACAGACGGGTCTAACACGGATTG     180
GACGAACCACTGAATTCCGCATTGCAGAGATATTGTATTTAAGTGCCTAGCTCGATACAA     240
TAAACGCCATTTGACCATTCACCACATTGGTGTGCACCTGGGTTGATGGCCGGACCGTTG     300
ATTCCCTGRCGACTACGAGCACATGCATGAAGCAGAAGGCTTCATT                   346
```

FIG. 10 b

SEQUENCE LISTING

<160> NUMBER OF SEQ ID NOS: 29

<210> SEQ ID NO 1
<211> LENGTH: 9597
<212> TYPE: DNA
<213> ORGANISM: Artificial Sequence
<220> FEATURE:
<223> OTHER INFORMATION: Description of Artificial Sequence: Synthetic
      pALV-SIN-4.2-Lys-IFNa-2B Vector polynucleotide

<400> SEQUENCE: 1

```
gatcccccgt gctgcagaac cgagcggcta ttgacttctt gctcctagct cacggccatg      60
gctgtgagga cattgcggga atgtgttgtt tcaatctgag tgatcacagt gagtctatac     120
agaagaagtt ccagctaatg aaggaacatg tcaataagat cggcgtgaac aacgacccaa     180
tcggaagttg gctgcgagga ttattcggag gaataggaga atgggccgta cacttgctga     240
aaggactgct tttgggggctt gtagttatct tgttgctagt agtatgcttg ccttgccttt     300
tgcaatgtgt atctagtagt attcgaaaga tgattgataa ttcactcggc tatcgcgagg     360
aatataaaaa aattacagga ggcttataag cagcccgaaa gaagagcgta ggcgagttct     420
tgtattccgt gtgatagctg gttggattgg taattgatcg gctggcacgc ggaatatagg     480
aggtcgctga atagtaaact tgtagacttg gctacagcat agagtatctt ctgtagctct     540
gatgactgct aggaaataat gctacggata atgtggggag ggcaaggctt gcgaatcggg     600
ttgtaacggg caaggcttga ctgaggggac aatagcatgt ttaggcgaaa agcggggctt     660
cggttgtacg cggttaggag tcccctcagg atatagtagt ttcgcttttg catagggagg     720
gggacggatt ggacgaacca ctgaattccg cattgcagag atattgtatt taagtgccta     780
gctcgataca ataaacgcca tttgaccatt caccacattg gtgtgcacct gggttgatgg     840
ccggaccgtt gattccctgr cgactacgag cacatgcatg aagcagaagg cttcatttgg     900
tgaccccgac gtgatcgtta gggaatacgc gctcactggc cgtcgtttta caacgtcgtg     960
actgggaaaa ccctggcgtt acccaactta atcgccttgc agcacatccc cctttcgcca    1020
gctggcgtaa tagcgaagag gcccgcaccg atcgcccttc ccaacagttg cgcagcctga    1080
atggcgaatg gaaattgtaa gcgttaatat tttgttaaaa ttcgcgttaa attttttgtta    1140 aatcagctca ttttttaacc aataggccga aatcggcaaa atcccttata aatcaaaaga    1200
atagaccgag atagggttga gtgttgttcc agtttggaac aagagtccac tattaaagaa    1260
cgtggactcc aacgtcaaag ggcgaaaaac cgtctatcag ggcgatggcc cactacgtga    1320
accatcaccc taatcaagtt ttttggggtc gaggtgccgt aaagcactaa atcggaaccc    1380 taagggagc ccccgattta gagcttgacg gggaaagccg gcgaacgtgg cgagaaagga    1440
```

```
agggaagaaa gcgaaaggag cgggcgctag ggcgctggca agtgtagcgg tcacgctgcg    1500
cgtaaccacc acacccgccg cgcttaatgc gccgctacag ggcgcgtcag gtggcacttt    1560
tcggggaaat gtgcgcggaa cccctatttg tttattttc taaatacatt caaatatgta    1620
tccgctcatg agacaataac cctgataaat gcttcaataa tattgaaaaa ggaagagtat    1680
gagtattcaa catttccgtg tcgcccttat ccctttttt gcggcatttt gccttcctgt    1740
ttttgctcac ccagaaacgc tggtgaaagt aaaagatgct gaagatcagt tgggtgcacg    1800
agtgggttac atcgaactgg atctcaacag cggtaagatc cttgagagtt ttcgccccga    1860
agaacgtttt ccaatgatga gcactttaa agttctgcta tgtggcgcgg tattatcccg    1920
tattgacgcc gggcaagagc aactcggtcg ccgcatacac tattctcaga atgacttggt    1980
tgagtactca ccagtcacag aaaagcatct tacggatggc atgacagtaa gagaattatg    2040
cagtgctgcc ataaccatga gtgataacac tgcggccaac ttacttctga caacgatcgg    2100
aggaccgaag gagctaaccg cttttttgca caacatgggg gatcatgtaa ctcgccttga    2160
tcgttgggaa ccggagctga atgaagccat accaaacgac gagcgtgaca ccacgatgcc    2220
tgtagcaatg gcaacaacgt tgcgcaaact attaactggc gaactactta ctctagcttc    2280
ccggcaacaa ttaatagact ggatggaggc ggataaagtt gcaggaccac ttctgcgctc    2340
ggcccttccg gctggctggt ttattgctga taaatctgga gccggtgagc gtgggtctcg    2400
cggtatcatt gcagcactgg ggccagatgg taagccctcc cgtatcgtag ttatctacac    2460
gacggggagt caggcaacta tggatgaacg aaatagacag atcgctgaga taggtgcctc    2520
actgattaag cattggtaac tgtcagacca agtttactca tatatacttt agattgattt    2580
aaaacttcat ttttaattta aaaggatcta ggtgaagatc ctttttgata atctcatgac    2640
caaaatccct taacgtgagt tttcgttcca ctgagcgtca gaccccgtag aaaagatcaa    2700
aggatcttct tgagatcctt ttttttctgcg cgtaatctgc tgcttgcaaa caaaaaaacc    2760
accgctacca gcggtggttt gtttgccgga tcaagagcta ccaactcttt ttccgaaggt    2820
aactggcttc agcagagcgc agataccaaa tactgtcctt ctagtgtagc cgtagttagg    2880
ccaccacttc aagaactctg tagcaccgcc tacatacctc gctctgctaa tcctgttacc    2940
agtggctgct gccagtggcg ataagtcgtg tcttaccggg ttggactcaa gacgatagtt    3000
accggataag gcgcagcggt cgggctgaac ggggggttcg tgcacacagc ccagcttgga    3060
gcgaacgacc tacaccgaac tgagatacct acagcgtgag ctatgagaaa gcgccacgct    3120
tcccgaaggg agaaaggcgg acaggtatcc ggtaagcggc agggtcggaa caggagagcg    3180
cacgagggag cttccagggg gaaacgcctg gtatctttat agtcctgtcg ggtttcgcca    3240
cctctgactt gagcgtcgat ttttgtgatg ctcgtcaggg gggcggagcc tatgaaaaa    3300 cgccagcaac gcggcctttt tacggttcct ggccttttgc tggccttttg ctcacatgtt    3360
ctttcctgcg ttatcccctg attctgtgga taaccgtatt accgcctttg agtgagctga    3420
taccgctcgc cgcagccgaa cgaccgagcg cagcgagtca gtgagcgagg aagcggaaga    3480
gcgcccaata cgcaaaccgc ctctccccgc gcgttggccg attcattaat gcagctggca    3540
cgacaggttt cccgactgga aagcgggcag tgagcgcaac gcaattaatg tgagttagct    3600
cactcattag gcaccccagg ctttacactt tatgcttccg gctcgtatgt tgtgtggaat    3660
tgtgagcgga taacaatttc acacaggaaa cagctatgac catgattacg ccaagcgcgc    3720
attggtaatt gatcggctgg cacgcggaat ataggaggtc gctgaatagt aaacttgtag    3780
acttggctac agcatagagt atcttctgta gctctgatga ctgctaggaa ataatgctac    3840
```

```
ggataatgtg gggagggcaa ggcttgcgaa tcgggttgta acgggcaagg cttgactgag   3900
gggacaatag catgtttagg cgaaaagcgg ggcttcggtt gtacgcggtt aggagtcccc   3960
tcaggatata gtagtttcgc ttttgcatag ggaggggaa atgtagtctt atgcaatact    4020
cttgtagtct tgcaacatgc ttatgtaacg atgagttagc aacatgcctt ataaggagag   4080
aaaaagcacc gtgcatgccg attggtggga gtaaggtggt atgatcgtgg tatgatcgtg   4140
ccttgttagg aaggcaacag acgggtctaa cacggattgg acgaaccact gaattccgca   4200
ttgcagagat attgtattta agtgcctagc tcgatacaat aaacgccatt tgaccattca   4260
ccacattggt gtgcacctgg gttgatggcc ggaccgttga ttccctgrcg actacgagca   4320
catgcatgaa gcagaaggct tcatttggtg accccgacgt gatcgttagg gaatagtggt   4380
cggccacagg cggcgtggcg atcctgtcct catccgtctc gcttattcgg ggagcggacg   4440
atgaccctag tagagggggc tgcggcttag gagggcagaa gctgagtggc gtcggaggga   4500
gccctactgc aggggccaa catacctac cgagaactca gagagtcgtt ggaagacggg     4560
aaggaagccc gacgactgag cggtccaccc caggcgtgat tccggttgct ctgcgtgatt   4620
ccggtcgccc ggtggatcaa gcatggaagc cgtcataaag gtgatttcgt ccgcgtgtaa   4680
gacctattgc gggaaaacct ctccttctaa gaaggaaata ggggctatgt tgtccctgtt   4740
acaaaaggaa gggttgctta cgtcccctc agacttatat tccccggggt cctgggatcc    4800
gataccgtcc ctattttgt gtttgcttca gcagccattt aattcttcag tgtcatcttg    4860
ttctgttgat gccactggaa caggattttc agcagtcttg caagaacat ctagctgaaa    4920 actttctgcc attcaatatt cttaccagtt cttcttgttt gaggtgagcc ataaattact   4980
agaacttcgt cactgacaag tttatgcatt ttattacttc tattatgtac ttactttgac   5040
ataacacaga cacgcacata ttttgctggg atttccacag tgtctctgtg tccttcacat   5100
ggttttactg tcatacttcc gttataacct tggcaatctg cccagctgcc catcacaaga   5160
aaagagattc cttttttatt acttctcttc agccaataaa caaaatgtga aagcccaaa    5220 caagaacttg tggggcaggc tgccatcaag ggagagacag ctgaagggtt gtgtagctca   5280
atagaattaa gaaataataa agctgtgtca gacagttttg cctgatttat acaggcacgc   5340
cccaagccag agaggctgtc tgccaaggcc accttgcagt ccttggtttg taagataagt   5400
cataggtaac ttttctggtg aattgcgtgg agaatcatga tggcagttct tgctgtttac   5460
tatggtaaga tgctaaaata ggagacagca agtaacact tgctgctgta ggtgctctgc    5520
tatccagaca gcgatggcac tcgcacacca agatgaggga tgctcccagc tgacggatgc   5580
tggggcagta acagtgggtc ccatgctgcc tgctcattag catcacctca gccctcacca   5640
gcccatcaga aggatcatcc caagctgagg aaagttgctc atcttcttca catcatcaaa   5700
cctttggcct gactgatgcc tcccggatgc ttaaatgtgg tcactgacat ctttattttt   5760
ctatgatttc aagtcagaac ctccggatca ggagggaaca catagtggga atgtaccctc   5820
agctccaagg ccagatcttc cttcaatgat catgcatgct acttaggaag gtgtgtgtgt   5880
gtgaatgtag aattgccttt gttattttt cttcctgctg tcaggaacat tttgaatacc    5940
agagaaaaag aaaagtgctc ttcttggcat gggaggagtt gtcacacttg caaaataaag   6000
gatgcagtcc caaatgttca taatctcagg gtctgaagga ggatcagaaa ctgtgtatac   6060
aatttcaggc ttctctgaat gcagcttttg aaagctgttc ctggccgagg cagtactagt   6120
cagaaccctc ggaaacagga acaaatgtct tcaaggtgca gcaggaggaa acaccttgcc   6180
```

```
catcatgaaa gtgaataacc actgccgctg aaggaatcca gctcctgttt gagcaggtgc   6240
tgcacactcc cacactgaaa caacagttca tttttatagg acttccagga aggatcttct   6300
tcttaagctt cttaattatg gtacatctcc agttggcaga tgactatgac tactgacagg   6360
agaatgagga actagctggg aatatttctg tttgaccacc atggagtcac ccatttcttt   6420
actggtattt ggaaataata attctgaatt gcaaagcagg agttagcgaa gatcttcatt   6480
tcttccatgt tggtgacagc acagttctgg ctatgaaagt ctgcttacaa ggaagaggat   6540
aaaaatcata gggataataa atctaagttt gaagacaatg aggttttagc tgcatttgac   6600
atgaagaaat tgagacctct actggatagc tatggtattt acgtgtcttt ttgcttagtt   6660
acttattgac cccagctgag gtcaagtatg aactcaggtc tctcgggcta ctggcatgga   6720
ttgattacat acaactgtaa ttttagcagt gatttagggt ttatgagtac ttttgcagta   6780
aatcataggg ttagtaatgt taatctcagg gaaaaaaaaa aaaagccaac cctgacagac   6840
atcccagctc aggtggaaat caaggatcac agctcagtgc ggtcccagag aacacaggga   6900
ctcttctctt aggacctta tgtacagggc ctcaagataa ctgatgttag tcagaagact    6960
ttccattctg gccacagttc agctgaggca atcctggaat tttctctccg ctgcacagtt   7020
ccagtcatcc cagtttgtac agttctggca ctttttgggt caggccgtga tccaaggagc   7080
agaagttcca gctatggtca gggagtgcct gaccgtccca actcactgca ctcaaacaaa   7140
ggcgaaacca caagagtggc ttttgttgaa attgcagtgt ggcccagagg ggctgcacca   7200
gtactggatt gaccacgagg caacattaat cctcagcaag tgcaatttgc agccattaaa   7260
ttgaactaac tgatactaca atgcaatcag tatcaacaag tggtttggct tggaagatgg   7320
agtctagggg ctctacagga gtagctactc tctaatggag ttgcattttg aagcaggaca   7380
ctgtgaaaag ctggcctcct aaagaggctg ctaaacatta gggtcaattt tccagtgcac   7440
tttctgaagt gtctgcagtt ccccatgcaa agctgcccaa acatagcact tccaattgaa   7500
tacaattata tgcaggcgta ctgcttcttg ccagcactgt ccttctcaaa tgaactcaac   7560
aaacaatttc aaagtctagt agaaagtaac aagctttgaa tgtcattaaa aagtatatct   7620
gctttcagta gttcagctta tttatgccca ctagaaacat cttgtacaag ctgaacactg   7680
gggctccaga ttagtggtaa aacctacttt atacaatcat agaatcatag aatggcctgg   7740
gttggaaggg accccaagga tcatgaagat ccaacacccc cgccacaggc agggccacca   7800
acctccagat ctggtactag accaggcagc ccagggctcc atccaacctg gccatgaaca   7860
cctcagggga tggagcatcc acaacctctc tgggcagcct gtgccagcac ctcaccaccc   7920
tctctgtgaa gaacttttcc ctgacatcca atctaagcct tccctccttg aggttagatc   7980 cactcccccct tgtgctatca ctgtctactc ttgtaaaaag ttgattctcc tccttttttgg  8040 aaggttgcaa tgaggtctcc ttgcagcctt cttctcttct gcaggatgaa caagcccagc   8100
tccctcagcc tgtctttata ggagaggtgc tccagccctc tgatcatctt tgtggccctc   8160
ctctggaccc gctccaagag ctccacatct ttcctgtact gggggcccca ggcctgaatg   8220
cagtactcca gatggggcct caaaagagca gagtaaagag ggacaatcac cttcctcacc   8280
ctgctggcca gccctcttct gatggagccc tggatacaac tggctttctg agctgcaact   8340
tctccttatc agttccacta ttaaaacagg aacaatacaa caggtgctga tggccagtgc   8400
agagtttttc acacttcttc atttcggtag atcttagatg aggaacgttg aagttgtgct   8460
tctgcgtgtg cttcttcctc ctcaaatact cctgcctgat acctcacccc acctgccact   8520
gaatggctcc atgcccccct gcagccaggg ccctgatgaa cccggcactg cttcagatgc   8580
```

```
tgtttaatag cacagtatga ccaagttgca cctatgaata cacaaacaat gtgttgcatc    8640
cttcagcact tgagaagaag agccaaattt gcattgtcag gaaatggttt agtaattctg    8700
ccaattaaaa cttgtttatc taccatggct gtttttatgg ctgttagtag tggtacactg    8760
atgatgaaca atggctatgc agtaaaatca agactgtaga tattgcaaca gactataaaa    8820
ttcctctgtg gcttagccaa tgtggtactt cccacattgt ataagaaatt tggcaagttt    8880
agagcaatgt ttgaagtgtt gggaaatttc tgtatactca agagggcgtt tttgacaact    8940
gtagaacaga ggaatcaaaa gggggtggga ggaagttaaa agaagaggca ggtgcaagag    9000
agcttgcagt cccgctgtgt gtacgacact ggcaacatga ggtctttgct aatcttggtg    9060
ctttgcttcc tgcccctggc tgccttaggg tgcgatctgc ctcagaccca cagcctgggc    9120
agcaggagga ccctgatgct gctggctcag atgaggagaa tcagcctgtt tagctgcctg    9180
aaggataggc acgattttgg ctttcctcaa gaggagtttg gcaaccagtt tcagaaggct    9240
gagaccatcc ctgtgctgca cgagatgatc cagcagatct ttaacctgtt tagcaccaag    9300
gatagcagcg ctgcttggga tgagaccctg ctggataagt tttacaccga gctgtaccag    9360
cagctgaacg atctggaggc ttgcgtgatc caggcgtgg gcgtgaccga gacccctctg    9420
atgaaggagg atagcatcct ggctgtgagg aagtactttc agaggatcac cctgtacctg    9480
aaggagaaga agtacagccc ctgcgcttgg gaagtcgtga gggctgagat catgaggagc    9540
tttagcctga gcaccaacct gcaagagagc ttgaggtcta aggagtaaaa agtctag      9597

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer ALV-SIN-1

<400> SEQUENCE: 2
atgcgcgcat tggtaattga tcggctgg                                       28

<210> SEQ ID NO 3
<211> LENGTH: 80
<212> TYPE: DNA
<213> ORGANISM: Artificial Sequence
<220> FEATURE:
<223> OTHER INFORMATION: Description of Artificial Sequence: Synthetic
      primer ALV-SIN-2

<400> SEQUENCE: 3
atatgcggcc gcggtaccgc ccgggcatcg atatcaagct tacggttcac taaacgagct    60
ctgcttatat agacctccca                                                80

<210> SEQ ID NO 4
<211> LENGTH: 59
<212> TYPE: DNA
<213> ORGANISM: Artificial Sequence
<220> FEATURE:
<223> OTHER INFORMATION: Description of Artificial Sequence: Synthetic
      primer ALV-SIN-3

<400> SEQUENCE: 4
atatgcggcc gcgtcgacgg ccggccagat ctgctgagcc ggtcgctacc attaccagt     59

<210> SEQ ID NO 5
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      primer ALV-SIN-4

<400> SEQUENCE: 5
atacgcgtat tccctaacga tcacgtcg                                          28

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer ALV-SIN-5

<400> SEQUENCE: 6
ctgaagtgta aggaatgtaa g                                                 21

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer ALV-SIN-6

<400> SEQUENCE: 7
gcgcgtctca tccccctccc tatgcaaaag                                        30

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Synthetic
      primer ALV-SIN-7

<400> SEQUENCE: 8
gggcgtctca gggacggatt ggacgaacca ctgaatt                                37

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer ALV-SIN-8

<400> SEQUENCE: 9
ttagtgcttt acggcacctc                                                   20

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Synthetic
      primer ALV-SIN-9

<400> SEQUENCE: 10
gacggatccg ataccgtccc tatttttgtg tttgcttc                               38

<210> SEQ ID NO 11
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      primer ALV-SIN-10

<400> SEQUENCE: 11
taacggatcc tagactttttt actccttaga                                      30

<210> SEQ ID NO 12
<211> LENGTH: 11945
<212> TYPE: DNA
<213> ORGANISM: Artificial Sequence
<220> FEATURE:
<223> OTHER INFORMATION: Description of Artificial Sequence: Synthetic
      proximal promoter and lysozyme signal polynucleotide

<400> SEQUENCE: 12
tgccgccttc tttgatattc actctgttgt atttcatctc ttcttgccga tgaaaggata      60
taacagtctg tataacagtc tgtgaggaaa tacttggtat ttcttctgat cagtgttttt     120
ataagtaatg ttgaatattg gataaggctg tgtgtccttt gtcttgggag acaaagccca     180
cagcaggtgg tggttggggt ggtggcagct cagtgacagg agaggttttt ttgcctgttt     240
tttttttttt ttttttttttt aagtaaggtg ttctttttttc ttagtaaatt ttctactgga   300
ctgtatgttt tgacaggtca gaaacatttc ttcaaaagaa gaaccttttg gaaactgtac     360
agcccttttc tttcattccc ttttgctttt ctgtgccaat gcctttggtt ctgattgcat     420
tatggaaaac gttgatcgga acttgaggtt tttatttata gtgtggcttg aaagcttgga     480
tagctgttgt tacacgagat accttattaa gtttaggcca gcttgatgct ttattttttc     540
cctttgaagt agtgagcgtt ctctggtttt tttcctttga aactggtgag cttagatttt     600
ttctaatggg atttttttacc tgatgatcta gttgcatacc caaatgcttg taaatgtttt    660
cctagttaac atgttgataa cttcggattt acatgttgta tatacttgtc atctgtgttt    720
ctagtaaaaa tatatggcat ttatagaaat acgtaattcc tgatttcctt tttttttatc    780
tctatgctct gtgtgtacag gtcaaacaga cttcactcct attttttattt atagaattttt 840 atatgcagtc tgtcgttggt tcttgtgttg taaggataca gccttaaatt tcctagagcg    900
atgctcagta aggcgggttg tcacatgggt tcaaatgtaa acgggcacg tttggctgct     960 gccttcccga gatccaggac actaaactgc ttctgcactg aggtataaat cgcttcagat   1020
cccagggaag tgcagatcca cgtgcatatt cttaaagaag aatgaatact ttctaaaata   1080
ttttggcata ggaagcaagc tgcatggatt tgtttgggac ttaaattatt ttggtaacgg   1140
agtgcatagg ttttaaacac agttgcagca tgctaacgag tcacagcgtt tatgcagaag   1200
tgatgcctgg atgcctgttg cagctgttta cggcactgcc ttgcagtgag cattgcagat   1260
aggggtgggg tgctttgtgt cgtgttccca cacgctgcca cacagccacc tcccggaaca   1320
catctcacct gctgggtact tttcaaacca tcttagcagt agtagatgag ttactatgaa   1380
acagagaagt tcctcagttg gatattctca tgggatgtct tttttcccat gttgggcaaa   1440
gtatgataaa gcatctctat ttgtaaatta tgcacttgtt agttcctgaa tcctttctat   1500
agcaccactt attgcagcag gtgtaggctc tggtgtggcc tgtgtctgtg cttcaatctt   1560
ttaaagcttc tttggaaata cactgacttg attgaagtct cttgaagata gtaaacagta   1620
cttacctttg atcccaatga aatcgagcat ttcagttgta aaagaattcc gcctattcat   1680
accatgtaat gtaattttac accccccagtg ctgacacttt ggaatatatt caagtaatag   1740
actttggcct caccctcttg tgtactgtat tttgtaatag aaaatatttt aaactgtgca   1800
```

```
tatgattatt acattatgaa agagacattc tgctgatctt caaatgtaag aaaatgagga    1860
gtgcgtgtgc ttttataaat acaagtgatt gcaaattagt gcaggtgtcc ttaaaaaaaa    1920
aaaaaaaaag taatataaaa aggaccaggt gttttacaag tgaaatacat tcctatttgg    1980
taaacagtta cattttatg aagattacca gcgctgctga ctttctaaac ataaggctgt     2040
attgtcttcc tgtaccattg catttcctca ttcccaattt gcacaaggat gtctgggtaa    2100
actattcaag aaatggcttt gaaatacagc atgggagctt gtctgagttg gaatgcagag    2160
ttgcactgca aaatgtcagg aaatggatgt ctctcagaat gcccaactcc aaaggatttt    2220
atatgtgtat atagtaagca gtttcctgat tccagcaggc caaagagtct gctgaatgtt    2280
gtgttgccgg agacctgtat ttctcaacaa ggtaagatgg tatcctagca actgcggatt    2340
ttaatacatt ttcagcagaa gtacttagtt aatctctacc tttagggatc gtttcatcat    2400
ttttagatgt tatacttgaa atactgcata acttttagct ttcatgggtt cctttttttc    2460
agcctttagg agactgttaa gcaatttgct gtccaacttt tgtgttggtc ttaaactgca    2520
atagtagttt accttgtatt gaagaaataa agaccatttt tatattaaaa aatacttttg    2580
tctgtcttca ttttgacttg tctgatatcc ttgcagtgcc cattatgtca gttcgtcag    2640 atattcagac atcaaaactt aacgtgagct cagtggagtt acagctgcgg ttttgatgct    2700
gttattattt ctgaaactag aaatgatgtt gtcttcatct gctcatcaaa cacttcatgc    2760
agagtgtaag gctagtgaga aatgcataca tttattgata cttttttaaa gtcaacttt    2820 tatcagattt ttttttcatt tggaaatata ttgttttcta gactgcatag cttctgaatc    2880
tgaaatgcag tctgattggc atgaagaagc acagcactct tcatcttact taaacttcat    2940
tttggaatga aggaagttaa gcaagggcac aggtccatga aatagagaca gtgcgctcag    3000
gagaaagtga acctggattt ctttggctag tgttctaaat ctgtagtgag gaaagtaaca    3060
cccgattcct tgaaagggct ccagctttaa tgcttccaaa ttgaaggtgg caggcaactt    3120
ggccactggt tatttactgc attatgtctc agtttcgcag ctaacctggc ttctccacta    3180
ttgagcatgg actatagcct ggcttcagag gccaggtgaa ggttgggatg ggtggaagga    3240
gtgctgggct gtggctgggg ggactgtggg gactccaagc tgagcttggg gtgggcagca    3300
cagggaaaag tgtgggtaac tatttttaag tactgtgttg caaacgtctc atctgcaaat    3360
acgtagggtg tgtactctcg aagattaaca gtgtgggttc agtaatatat ggatgaattc    3420
acagtggaag cattcaaggg tagatcatct aacgacacca gatcatcaag ctatgattgg    3480
aagcggtatc agaagagcga ggaaggtaag cagtcttcat atgttttccc tccacgtaaa    3540
gcagtctggg aaagtagcac cccttgagca gagacaagga ataattcag gagcatgtgc     3600 taggagaact tccttgctga attctacttg caagagcttt gatgcctggc ttctggtgcc    3660
ttctgcagca cctgcaaggc ccagagcctg tggtgagctg gagggaaaga ttctgctcaa    3720
gtccaagctt cagcaggtca ttgtctttgc ttcttccccc agcactgtgc agcagagtgg    3780
aactgatgtc gaagcctcct gtccactacc tgttgctgca ggcagactgc tctcagaaaa    3840
agagagctaa ctctatgcca tagtctgaag gtaaaatggg ttttaaaaaa gaaaacacaa    3900
aggcaaaacc ggctgcccca tgagaagaaa gcagtggtaa acatggtaga aaaggtgcag    3960
aagcccccag gcagtgtgac aggcccctcc tgccacctag aggcgggaac aagcttccct    4020
gcctagggct ctgcccgcga agtgcgtgtt tctttggtgg gttttgtttg gcgtttggtt    4080
ttgagattta gacacaaggg aagcctgaaa ggaggtgttg ggcactattt tggtttgtaa    4140
```

-continued

```
agcctgtact tcaaatatat attttgtgag ggagtgtagc gaattggcca atttaaaata    4200
aagttgcaag agattgaagg ctgagtagtt gagagggtaa cacgtttaat gagatcttct    4260
gaaactactg cttctaaaca cttgtttgag tggtgagacc ttggataggt gagtgctctt    4320
gttacatgtc tgatgcactt gcttgtcctt ttccatccac atccatgcat tccacatcca    4380
cgcatttgtc acttatccca tatctgtcat atctgacata cctgtctctt cgtcacttgg    4440
tcagaagaaa cagatgtgat aatccccagc cgccccaagt tgagaagat ggcagttgct    4500
tctttcccctt tttcctgcta agtaaggatt ttctcctggc tttgacacct cacgaaatag    4560
tcttcctgcc ttacattctg gcattatttt caaatatctt tggagtgcgc tgctctcaag    4620
tttgtgtctt cctactctta gagtgaatgc tcttagagtg aaagagaagg aagagaagat    4680
gttggccgca gttctctgat gaacacacct ctgaataatg ccaaaggtg ggtgggtttc    4740
tctgaggaac gggcagcgtt tgcctctgaa agcaaggagc tctgcggagt tgcagttatt    4800
ttgcaactga tggtggaact ggtgcttaaa gcagattccc taggttccct gctacttctt    4860
ttccttcttg gcagtcagtt tatttctgac agacaaacag ccaccccac tgcaggctta    4920
gaaagtatgt ggctctgcct gggtgtgtta cagctctgcc ctggtgaaag gggattaaaa    4980
cgggcaccat tcatcccaaa caggatcctc attcatggat caagctgtaa ggaacttggg    5040
ctccaacctc aaaacattaa ttggagtacg aatgtaatta aaactgcatt ctcgcattcc    5100
taagtcattt agtctggact ctgcagcatg taggtcggca gctcccactt tctcaaagac    5160
cactgatgga ggagtagtaa aaatggagac cgattcagaa caaccaacgg agtgttgccg    5220
aagaaactga tggaaataat gcatgaattg tgtggtggac attttttta aatacataaa    5280
ctacttcaaa tgaggtcgga aaggtcagt gttttattag cagccataaa accaggtgag    5340
cgagtaccat ttttctctac aagaaaaacg attctgagct ctgcgtaagt ataagttctc    5400
catagcggct gaagctcccc cctggctgcc tgccatctca gctggagtgc agtgccattt    5460
ccttggggtt tctctcacag cagtaatggg acaatacttc acaaaaattc tttcttttcc    5520
tgtcatgtgg gatccctact gtgccctcct ggttttacgt tacccctga ctgttccatt    5580
cagcggtttg gaaagagaaa aagaatttgg aaataaaaca tgtctacgtt atcacctcct    5640
ccagcatttt ggttttaat tatgtcaata actggcttag atttggaaat gagaggggt    5700
tgggtgtatt accgaggaac aaaggaaggc ttatataaac tcaagtcttt tatttagaga    5760
actggcaagc tgtcaaaaac aaaaaggcct taccaccaaa ttaagtgaat agccgctata    5820
gccagcaggg ccagcacgag ggatggtgca ctgctggcac tatgccacgg cctgcttgtg    5880
actctgagag caactgcttt ggaaatgaca gcacttggtg caatttcctt tgtttcagaa    5940
tgcgtagagc gtgtgcttgg cgacagtttt tctagttagg ccacttcttt tttccttctc    6000
tcctcattct cctaagcatg tctccatgct ggtaatccca gtcaagtgaa cgttcaaaca    6060
atgaatccat cactgtagga ttctcgtggt gatcaaatct ttgtgtgagg tctataaaat    6120
atggaagctt atttatttt cgttcttcca tatcagtctt ctctatgaca attcacatcc    6180
accacagcaa attaaaggtg aaggaggctg gtgggatgaa gagggtcttc tagctttacg    6240
ttcttccttg caaggccaca ggaaaatgct gagagctgta gaatacagcc tggggtaaga    6300
agttcagtct cctgctggga cagctaaccg catcttataa cccccttctga gactcatctt    6360
aggaccaaat agggtctatc tggggttttt gttcctgctg ttcctcctgg aaggctatct    6420
cactatttca ctgctcccac ggttacaaac caaagataca gcctgaattt tttctaggcc    6480
acattacata aatttgacct ggtaccaata ttgttctcta tatagttatt tccttcccca    6540
```

```
ctgtgtttaa cccctaagg cattcagaac aactagaatc atagaatggt ttggattgga      6600 agggcctta aacatcatcc atttccaacc ctctgccatg ggctgcttgc cacccactgg      6660
ctcaggctgc ccagggcccc atccagcctg gccttgagca cctccaggga tggggcaccc      6720
acagcttctc tgggcagcct gtgccaacac ctcaccactc tctgggtaaa gaattctctt      6780
ttaacatcta atctaaatct cttctctttt agtttaaagc cattcctctt tttcccgttg      6840
ctatctgtcc aagaaatgtg tattggtctc cctcctgctt ataagcagga agtactggaa      6900
ggctgcagtg aggtctcccc acagccttct cttctccagg ctgaacaagc ccagctcctt      6960
cagcctgtct tcgtaggaga tcatcttagt ggccctcctc tggacccatt ccaacagttc      7020
cacggctttc ttgtggagcc ccaggtctgg atgcagtact tcagatgggg ccttacaaag      7080
gcagagcaga tggggacaat cgcttacccc tccctgctgg ctgcccctgt tttgatgcag      7140
cccagggtac tgttggcctt tcaggctccc agaccccttg ctgatttgtg tcaagctttt      7200
catccaccag aacccacgct tcctggttaa tacttctgcc ctcacttctg taagcttgtt      7260
tcaggagact tccattcttt aggacagact gtgttacacc tacctgccct attcttgcat      7320
atatacattt cagttcatgt ttcctgtaac aggacagaat atgtattcct ctaacaaaaa      7380
tacatgcaga attcctagtg ccatctcagt agggttttca tggcagtatt agcacatagt      7440
caatttgctg caagtacctt ccaagctgcg gcctcccata aatcctgtat ttgggatcag      7500 ttacctttg gggtaagctt ttgtatctgc agagaccctg ggggttctga tgtgcttcag      7560
ctctgctctg ttctgactgc accatttct agatcaccca gttgttcctg tacaacttcc      7620
ttgtcctcca tcctttccca gcttgtatct ttgacaaata caggcctatt tttgtgtttg      7680
cttcagcagc catttaattc ttcagtgtca tcttgttctg ttgatgccac tggaacagga      7740
ttttcagcag tcttgcaaag aacatctagc tgaaaacttt ctgccattca atattcttac      7800
cagttcttct tgtttgaggt gagccataaa ttactagaac ttcgtcactg acaagtttat      7860
gcattttatt acttctatta tgtacttact ttgacataac acagacacgc acatattttg      7920
ctgggatttc cacagtgtct ctgtgtcctt cacatggttt tactgtcata cttccgttat      7980
aaccttggca atctgcccag ctgcccatca caagaaaaga gattccttt ttattacttc      8040 tcttcagcca ataaacaaaa tgtgagaagc ccaaacaaga acttgtgggg caggctgcca      8100
tcaagggaga gacagctgaa gggttgtgta gctcaataga attaagaaat aataaagctg      8160
tgtcagacag ttttgcctga tttatacagg cacgccccaa gccagagagg ctgtctgcca      8220
aggccacctt gcagtccttg gtttgtaaga taagtcatag gtaactttc tggtgaattg      8280 cgtggagaat catgatggca gttcttgctg tttactatgg taagatgcta aaataggaga      8340
cagcaaagta acacttgctg ctgtaggtgc tctgctatcc agacagcgat ggcactcgca      8400
caccaagatg agggatgctc ccagctgacg gatgctgggg cagtaacagt gggtcccatg      8460
ctgcctgctc attagcatca cctcagccct caccagccca tcagaaggat catcccaagc      8520
tgaggaaagt tgctcatctt cttcacatca tcaaaccttt ggcctgactg atgcctcccg      8580
gatgcttaaa tgtggtcact gacatcttta tttttctatg atttcaagtc agaacctccg      8640
gatcaggagg gaacacatag tgggaatgta ccctcagctc caaggccaga tcttccttca      8700
atgatcatgc atgctactta ggaaggtgtg tgtgtgtgaa tgtagaattg cctttgttat      8760 ttttctcttcc tgctgtcagg aacattttga ataccagaga aaaagaaaag tgctcttctt      8820
ggcatgggag gagttgtcac acttgcaaaa taaaggatgc agtcccaaat gttcataatc      8880
```

```
tcagggtctg aaggaggatc agaaactgtg tatacaattt caggcttctc tgaatgcagc   8940
ttttgaaagc tgttcctggc cgaggcagta ctagtcagaa ccctcggaaa caggaacaaa   9000
tgtcttcaag gtgcagcagg aggaaacacc ttgcccatca tgaaagtgaa taaccactgc   9060
cgctgaagga atccagctcc tgtttgagca ggtgctgcac actcccacac tgaaacaaca   9120
gttcattttt ataggacttc caggaaggat cttcttctta agcttcttaa ttatggtaca   9180
tctccagttg gcagatgact atgactactg acaggagaat gaggaactag ctgggaatat   9240
ttctgtttga ccaccatgga gtcacccatt tctttactgg tatttggaaa taataattct   9300
gaattgcaaa gcaggagtta gcgaagatct tcatttcttc catgttggtg acagcacagt   9360
tctggctatg aaagtctgct tacaaggaag aggataaaaa tcatagggat aataaatcta   9420
agtttgaaga caatgaggtt ttagctgcat ttgacatgaa gaaattgaga cctctactgg   9480
atagctatgg tatttacgtg tcttttttgct tagttactta ttgaccccag ctgaggtcaa   9540
gtatgaactc aggtctctcg ggctactggc atggattgat tacatacaac tgtaatttta   9600
gcagtgattt agggtttatg agtacttttg cagtaaatca tagggttagt aatgttaatc   9660
tcagggaaaa aaaaaaaaag ccaaccctga cagacatccc agctcaggtg gaaatcaagg   9720
atcacagctc agtgcggtcc cagagaacac agggactctt ctcttaggac ctttatgtac   9780
agggcctcaa gataactgat gttagtcaga agactttcca ttctggccac agttcagctg   9840
aggcaatcct ggaattttct ctccgctgca cagttccagt catcccagtt tgtacagttc   9900
tggcactttt tgggtcaggc cgtgatccaa ggagcagaag ttccagctat ggtcagggag   9960
tgcctgaccg tcccaactca ctgcactcaa acaaaggcga aaccacaaga gtggcttttg  10020
ttgaaattgc agtgtggccc agaggggctg caccagtact ggattgacca cgaggcaaca  10080
ttaatcctca gcaagtgcaa tttgcagcca ttaaattgaa ctaactgata ctacaatgca  10140
atcagtatca acaagtggtt tggcttggaa gatggagtct aggggctcta caggagtagc  10200
tactctctaa tggagttgca ttttgaagca ggacactgtg aaaagctggc ctcctaaaga  10260
ggctgctaaa cattagggtc aattttccag tgcactttct gaagtgtctg cagttcccca  10320
tgcaaagctg cccaaacata gcacttccaa ttgaatacaa ttatatgcag gcgtactgct  10380
tcttgccagc actgtccttc tcaaatgaac tcaacaaaca atttcaaagt ctagtagaaa  10440
gtaacaagct ttgaatgtca ttaaaaagta tatctgcttt cagtagttca gcttatttat  10500
gcccactaga aacatcttgt acaagctgaa cactggggct ccagattagt ggtaaaacct  10560
actttataca atcatagaat catagaatgg cctgggttgg aagggacccc aaggatcatg  10620
aagatccaac accccgccca caggcagggc caccaacctc cagatctggt actagaccag  10680
gcagcccagg gctccatcca acctggccat gaacacctcc agggatggag catccacaac  10740
ctctctgggc agcctgtgcc agcacctcac caccctctct gtgaagaact tttccctgac  10800
atccaatcta agccttccct ccttgaggtt agatccactc cccttgtgc tatcactgtc  10860
tactcttgta aaaagttgat tctcctcctt ttggaaggt tgcaatgagg tctccttgca  10920
gccttcttct cttctgcagg atgaacaagc ccagctccct cagcctgtct ttataggaga  10980
ggtgctccag ccctctgatc atctttgtgg ccctcctctg gacccgctcc aagagctcca  11040
catctttcct gtactggggg ccccaggcct gaatgcagta ctccagatgg ggcctcaaaa  11100
gagcagagta aagagggaca atcaccttcc tcaccctgct ggccagccct cttctgatgg  11160
agccctggat acaactggct ttctgagctg caacttctcc ttatcagttc cactattaaa  11220
acaggaacaa tacaacaggt gctgatggcc agtgcagagt ttttcacact tcttcatttc  11280
```

```
ggtagatctt agatgaggaa cgttgaagtt gtgcttctgc gtgtgcttct tcctcctcaa    11340
atactcctgc ctgatacctc accccacctg ccactgaatg gctccatggc ccctgcagc     11400 cagggccctg atgaacccgg cactgcttca gatgctgttt aatagcacag tatgaccaag   11460
ttgcacctat gaatacacaa acaatgtgtt gcatccttca gcacttgaga agaagagcca   11520
aatttgcatt gtcaggaaat ggtttagtaa ttctgccaat taaaacttgt ttatctacca   11580
tggctgtttt tatggctgtt agtagtggta cactgatgat gaacaatggc tatgcagtaa   11640
aatcaagact gtagatattg caacagacta taaaattcct ctgtggctta gccaatgtgg   11700
tacttcccac attgtataag aaatttggca agtttagagc aatgtttgaa gtgttgggaa   11760
atttctgtat actcaagagg gcgttttga  caactgtaga acagaggaat caaaaggggg   11820
tgggaggaag ttaaaagaag aggcaggtgc aagagagctt gcagtcccgc tgtgtgtacg   11880
acactggcaa catgaggtct ttgctaatct tggtgctttg cttcctgccc ctggctgcct   11940
taggg                                                                11945
```

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      BAC 26 primer-1

<400> SEQUENCE: 13
gcggaattca aagaagaaag ctgaaaaac                                        29

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      BAC 26 primer-2

<400> SEQUENCE: 14
gcgggtacct tcaaatacta caagtgaaa                                        29

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      BAC 26-OV primer 1

<400> SEQUENCE: 15
ggcctcgagt caagttctga gtaggtttta gtg                                   33

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      BAC 26-OV primer 2

<400> SEQUENCE: 16
gcgcgtctct gtctagagca aacagcagaa cagtgaaaat g                          41

<210> SEQ ID NO 17

```
<211> LENGTH: 50
<212> TYPE: DNA
<213> ORGANISM: Artificial Sequence
<220> FEATURE:
<223> OTHER INFORMATION: Description of Artificial Sequence: Synthetic
      CTLA-4-Fc primer 1

<400> SEQUENCE: 17
gcgcgtctca agacaactca gagttcacca tgggtgtact gctcacacag                 50

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
      CTLA-4-Fc primer 2

<400> SEQUENCE: 18
ggcccgggag ttttgtcaga agatttggg                                        29

<210> SEQ ID NO 19
<211> LENGTH: 11868
<212> TYPE: DNA
<213> ORGANISM: Artificial Sequence
<220> FEATURE:
<223> OTHER INFORMATION: Description of Artificial Sequence: Synthetic
      pSIN-OV-3.5-I-CTLA4-inv vector polynucleotide

<400> SEQUENCE: 19
aattgctaga ctaggatccc ccgtgctgca gaaccgagcg gctattgact tcttgctcct      60
agctcacggc catggctgtg aggacattgc gggaatgtgt tgtttcaatc tgagtgatca    120
cagtgagtct atacagaaga agttccagct aatgaaggaa catgtcaata agatcggcgt    180
gaacaacgac ccaatcggaa gttggctgcg aggattattc ggaggaatag agaatgggc     240 cgtacacttg ctgaaaggac tgcttttggg gcttgtagtt atcttgttgc tagtagtatg    300
cttgccttgc cttttgcaat gtgtatctag tagtattcga agatgattg ataattcact     360 cggctatcgc gaggaatata aaaaaattac aggaggctta taagcagccc gaaagaagag    420
cgtaggcgag ttcttgtatt ccgtgtgata gctggttgga ttggtaattg atcggctggc    480
acgcggaata taggaggtcg ctgaatagta aacttgtaga cttggctaca gcatagagta    540
tcttctgtag ctctgatgac tgctaggaaa taatgctacg gataatgtgg ggagggcaag    600
gcttgcgaat cgggttgtaa cgggcaaggc ttgactgagg ggacaatagc atgtttaggc    660
gaaaagcggg gcttcggttg tacgcggtta ggagtccct caggatatag tagttttcgct    720 tttgcatagg gaggggacg gattggacga accactgaat tccgcattgc agagatattg    780
tatttaagtg cctagctcga tacaataaac gccatttgac cattcaccac attggtgtgc    840
acctgggttg atggccggac cgttgattcc ctgrcgacta cgagcacatg catgaagcag    900
aaggcttcat ttggtgaccc cgacgtgatc gttagggaat acgcgctcac tggccgtcgt    960
tttacaacgt cgtgactggg aaaaccctgg cgttacccaa cttaatcgcc ttgcagcaca   1020
tccccctttc gccagctggc gtaatagcga agaggcccgc accgatcgcc cttcccaaca   1080
gttgcgcagc ctgaatggcg aatggaaatt gtaagcgtta atattttgtt aaaattcgcg   1140
ttaaattttt gttaaatcag ctcatttttt aaccaatagg ccgaaatcgg caaaatccct   1200
tataaatcaa aagaatagac cgagataggg ttgagtgttg ttccagtttg gaacaagagt   1260
ccactattaa agaacgtgga ctccaacgtc aaagggcgaa aaaccgtcta tcagggcgat   1320
```

```
ggcccactac gtgaaccatc accctaatca agttttttgg ggtcgaggtg ccgtaaagca      1380
ctaaatcgga accctaaagg gagcccccga tttagagctt gacggggaaa gccggcgaac      1440
gtggcgagaa aggaagggaa gaaagcgaaa ggagcgggcg ctagggcgct ggcaagtgta      1500
gcggtcacgc tgcgcgtaac caccacaccc gccgcgctta atgcgccgct acagggcgcg      1560
tcaggtggca cttttcgggg aaatgtgcgc ggaaccccta tttgtttatt tttctaaata      1620
cattcaaata tgtatccgct catgagacaa taaccctgat aaatgcttca ataatattga      1680
aaaaggaaga gtatgagtat tcaacatttc cgtgtcgccc ttattccctt ttttgcggca      1740
ttttgccttc ctgttttgc tcacccagaa acgctggtga agtaaaaga tgctgaagat       1800 cagttgggtg cacgagtggg ttacatcgaa ctggatctca acagcggtaa gatccttgag      1860
agttttcgcc ccgaagaacg ttttccaatg atgagcactt taaagttct gctatgtggc       1920 gcggtattat cccgtattga cgccgggcaa gagcaactcg gtcgccgcat acactattct      1980
cagaatgact tggttgagta ctcaccagtc acagaaaagc atcttacgga tggcatgaca      2040
gtaagagaat tatgcagtgc tgccataacc atgagtgata acactgcggc caacttactt      2100
ctgacaacga tcggaggacc gaaggagcta accgcttttt tgcacaacat ggggatcat       2160 gtaactcgcc ttgatcgttg ggaaccggag ctgaatgaag ccataccaaa cgacgagcgt      2220
gacaccacga tgcctgtagc aatggcaaca acgttgcgca aactattaac tggcgaacta      2280
cttactctag cttcccggca acaattaata gactggatgg aggcggataa agttgcagga      2340
ccacttctgc gctcggccct tccggctggc tggtttattg ctgataaatc tggagccggt      2400
gagcgtgggt ctcgcggtat cattgcagca ctggggccag atggtaagcc ctcccgtatc      2460
gtagttatct acacgacggg gagtcaggca actatggatg aacgaaatag acagatcgct      2520
gagataggtg cctcactgat taagcattgg taactgtcag accaagttta ctcatatata      2580
ctttagattg atttaaaact tcatttttaa tttaaaagga tctaggtgaa gatccttttt      2640
gataatctca tgaccaaaat cccttaacgt gagttttcgt tccactgagc gtcagacccc      2700
gtagaaaaga tcaaaggatc ttcttgagat cctttttttc tgcgcgtaat ctgctgcttg      2760
caaacaaaaa aaccaccgct accagcggtg gtttgtttgc cggatcaaga gctaccaact      2820 cttttttccga aggtaactgg cttcagcaga gcgcagatac caaatactgt ccttctagtg      2880
tagccgtagt taggccacca cttcaagaac tctgtagcac cgcctacata cctcgctctg      2940
ctaatcctgt taccagtggc tgctgccagt ggcgataagt cgtgtcttac cgggttggac      3000
tcaagacgat agttaccgga taaggcgcag cggtcgggct gaacggggggg ttcgtgcaca      3060 cagcccagct tggagcgaac gacctacacc gaactgagat acctacagcg tgagctatga      3120
gaaagcgcca cgcttcccga agggagaaag gcggacaggt atccggtaag cggcagggtc      3180
ggaacaggag agcgcacgag ggagcttcca gggggaaacg cctggtatct ttatagtcct      3240
gtcgggtttc gccacctctg acttgagcgt cgatttttgt gatgctcgtc agggggggcgg      3300 agcctatgga aaaacgccag caacgcggcc ttttacggt tcctggcctt ttgctggcct       3360
tttgctcaca tgttctttcc tgcgttatcc cctgattctg tggataaccg tattaccgcc      3420
tttgagtgag ctgataccgc tcgccgcagc cgaacgaccg agcgcagcga gtcagtgagc      3480
gaggaagcgg aagagcgccc aatacgcaaa ccgcctctcc ccgcgcgttg gccgattcat      3540
taatgcagct ggcacgacag gtttcccgac tggaaagcgg gcagtgagcg caacgcaatt      3600
aatgtgagtt agctcactca ttaggcaccc caggctttac actttatgct tccggctcgt      3660
atgttgtgtg gaattgtgag cggataacaa tttcacacag gaaacagcta tgaccatgat      3720
```

```
tacgccaagc gcgcattggt aattgatcgg ctggcacgcg aatataggag ggtcgctgaa    3780
tagtaaactt gtagacttgg ctacagcata gagtatcttc tgtagctctg atgactgcta    3840
ggaaataatg ctacggataa tgtggggagg gcaaggcttg cgaatcgggt tgtaacgggc    3900
aaggcttgac tgaggggaca atagcatgtt taggcgaaaa gcggggcttc ggttgtacgc    3960
ggttaggagt cccctcagga tatagtagtt tcgcttttgc atagggaggg ggaaatgtag    4020
tcttatgcaa tactcttgta gtcttgcaac atgcttatgt aacgatgagt tagcaacatg    4080
ccttataagg agagaaaaag caccgtgcat gccgattggt gggagtaagg tggtatgatc    4140
gtggtatgat cgtgccttgt taggaaggca acagacgggc taacacggga ttggacgaac    4200
cactgaattc cgcattgcag agatattgta tttaagtgcc tagctcgata caataaacgc    4260
catttgacca ttcaccacat tggtgtgcac ctgggttgat ggccggaccg ttgattccct    4320
grcgactacg agcacatgca tgaagcagaa ggcttcattt ggtgaccccg acgtgatcgt    4380
tagggaatag tggtcggcca caggcggcgt ggcgatcctg tcctcatccg tctcgcttat    4440
tcggggagcg gacgatgacc ctagtagagg gggctgcggc ttaggagggc agaagctgag    4500
tggcgtcgga gggagcccta ctgcaggggg ccaacatacc ctaccgagaa ctcagagagt    4560
cgttggaaga cgggaaggaa gcccgacgac tgagcggtcc accccaggcg tgattccggt    4620
tgctctgcgt gattccggtc gccggtggta tcaagcatgg aagccgtcat aaaggtgatt    4680
tcgtccgcgt gtaagaccta ttgcgggaaa acctctcctt ctaagaagga aataggggct    4740
atgttgtccc tgttacaaaa ggaagggttg cttacgtccc cctcagactt atattccccg    4800
gggtcctggg atcccattac cgcggcgctc tctcagcggg ctatggtact tggaaaatcg    4860
ggagagttaa aaacctgggg attggttttg ggggcattga aggcggctcg agatccggta    4920
ccttcaaata ctacaagtga aaagtgtttg cttaaacatg ttttattatt gattaaagga    4980
acaaaagagc acattcacaa gacccattac atatgggtac aaggaaaaca atttgaatag    5040
taatatacca tatttgccaa cataccatga ttgagtcaaa gtttagggag aaatgtgaat    5100
tataagattt ttataatgca tctttaggaa gtcaggaaga gccttgtagt atcaggaaca    5160
cagagaacaa gcaattgcct tgtcagcata ggaatggttg gtgacagttg ataatttaat    5220
ctgagagatt ttgagtgact aattctggag cagcttggtc atacagatat ctggcttaat    5280
tggaaggctg catttttccc ccataaacct tctgctgatg tatcaggttg catttttcag    5340
tgtgatgact cagtactgtg agtccaattt cattcccttt agccttcatc catgagttac    5400
cagtattact ctgtgtaaag gaaaagtgaa ttgcacctgt tctcacagtg taatttcttt    5460 ctgattttt ttctagatta agctccagct tttatgaagt ctggatgcag cagataacat    5520
acttttcatt ttaccccctga tactacagtg ctctgggtct tgttggaagg gacagagttt    5580
ttcagctttc ttctttgaat tcctcattta cccggagaca gggagaggct cttctgcgtg    5640
tagtggttgt gcagagcctc atgcatcacg gagcatgaga agacgttccc ctgctgccac    5700
ctgctcttgt ccacggtgag cttgctgtag aggaagaagg agccgtcgga gtccagcacg    5760
ggaggcgtgg tcttgtagtt gttctccggc tgcccattgc tctcccactc cacggcgatg    5820
tcgctgggat agaagccttt gaccaggcag gtcaggctga cctggttctt ggtcagctca    5880
tcccgggatg ggggcagggt gtacacctgt ggttctcggg gctgcccttt ggctttggag    5940
atggttttct cgatggggc tgggagggct tgttggaga ccttgcactt gtactccttg    6000
ccattcagcc agtcctggtg caggacggtg aggacgctga ccaccggta cgtgctgttg    6060
```

```
tactgctcct cccgcggctt tgtcttggca ttatgcacct ccacgccgtc cacgtaccag   6120
ttgaacttga cctcagggtc ttcgtggctc acgtccacca ccacgcatgt gacctcaggg   6180
gtccgggaga tcatgagggt gtccttgggt tttgggggga agaggaagac tgacgatccc   6240
cccaggagtt caggtgctgg ggacggtggg gatgtgtgag ttttgtcaga agatttgggc   6300
tcctgatcag aatctgggca cggttctgga tcaattacat aaatctgggt tccgttgcct   6360
atgcccaggt agtatggcgg tgggtacatg agctccacct tgcagatgta gagtcccgtg   6420
tccatggccc tcagtccttg gatagtgagg ttcacttgat ttccactgga ggtgcccgtg   6480
cagatggaat catctaggaa ggtcaactca ttccccatca tgtaggttgc cgcacagact   6540
tcagtcacct ggctgtcagc ctgccgaagc actgtcaccc ggacctcagt ggctttgcct   6600
ggagatgcat actcacacac aaagctrgcg atgcctcggc tgctggccag taccacagca   6660
ggctgggcca cgtgcattgc catgctcgcc atgcttggaa acaggagtgc aaggaccaga   6720
ctgagcagcg tcctctgtgt gagcagtaca cccatggtga actctgagtt gtctagagca   6780
aacagcagaa cagtgaaaat gtaaggatgg aatgctgtac atagtaccat gcagggtact   6840
ctatggtagg ctacaacagt aaattacgag cagtttttag gcaattaaat gttaacaagt   6900
agttttaaag taattctgtg gtaatgtgtc tgttgctata tccacctctc atgtgcatgt   6960
tcaaaaccat attcataaat ctatttatgt atttgcattc agttgtcttt tgggtagcaa   7020
actgtcccag aagccagttg cctctacata tttttgttca gtgaaagcta gaattcattg   7080
atacttttca gtacctctga ttaaaacaca atctgatagg cttgcaaaac tggaaattca   7140
aagagcaaat ttcagtaaac tttaggtttg gacagatata tgagaaagca gaggcttgct   7200
gactatttta tttcttattt ttattcccta aaaataaatg tagagaaata tctgtttgtt   7260
gcacactact tgctatgagt agatcttcaa aagtattttt acctttgttt tggtgatggc   7320
agaatagata aggaatgtaa tttatatggg gtcatgtagt ctaggagaaa gacacgcatg   7380
taattcatat tctgctctat tgcactttca ggtatggttt gctttgctca aagatatgca   7440
tgtgtactgt agtataaaact ttctgtggag ttaaatttta gtggtgacat tcagacagaa   7500
gagaaatgca gacatgataa aatagcaatg tttactataa aacagagcca ctgaatgaat   7560
tcttgttcat gacatagacc aatagaagat ttatacttgt tctgtctgtt tctattataa   7620
agagctgaac tgtacaacta ttgtatagcc agtgtgctta tataaagcac agcttttgga   7680
gccagcatga atctagttgc tttcctgaga tttatataat ctgtgaaagt cagaagtcct   7740
tcagagccca gcccttttata tgcgtactga gtgctgggc ctcaggattg gattttctgt   7800
attaaacccc tcaaaagttt ttactgacca cgtgtgtgag tatacacaca cacattttttc   7860
tcattttctt ttctgtatat aagttcacat gtatctatta ttgtaagaat atacgtttat   7920
gcaccccca cattttatc ttgtgtagtg atcagcagct gcactttgca ggaattaaac   7980
ttctagagaa ttttcacatt aaaataactc cccagaattc actgaacacc atgattttgc   8040
tctctgtgca ctctgtaggg ctagaagtta atcaagcaaa ctgcaaagca tatcagatag   8100
tgaacgacag gataagatgt tctgaaatta aaaacatatt ttaagcacaa agaataagcc   8160
tcctgaaaac aaaacacaaag cttttacaca taataaaata gtgcagaatg catacacagg   8220
tgagaagttt ttataggggg tatcacgcag gtacttcacc cttaaagata caacacatag   8280
cacaataatt gttaattttt taaagtttag gtgcaagtaa gagctaatat agagagaagg   8340
taattccaga gagttgctta cctttcgagc ttgactgcta aaggcaatac agcttttctag   8400
ctgtatgtac agacactggc tgagccctgg ggaatatata gtctgaattg tgacccaccc   8460
```

```
acaggttccc ttcagaagtt tgacctttga caccatagaa atcatttaat gggattgggt    8520
tagatttag tttcaatagg tccattttgg attgaatgga gagcaaatat tagtttttaa    8580
ttctgggtaa caatgtgttt tctgcctgtt ctgctaatcc atcaggactg ttggatggga    8640
gagaagactg ggaaatattg ctcatgttcc attgagcttc agttacaacc agataatggg    8700
atctttaaga aaacagaaaa atgtgggaac cttggagatg gaaaacataa ttagcaatta    8760
ttagttagtg tgcttattac tatggttgta gtaacagacc agaagtctgt ttcatttgat    8820
ccttcttgta tgtacaatgt gcatctgagc cacgctagac aggacataaa tgagaacaag    8880
acttgaccta ttattttctt gacaaaatag gagaaataaa gaagcgtgca tgtgaaggag    8940
ccaactgaga ctagagtgaa gagcagacac actttctttc ctatagttgg aatatttaaa    9000
tctatctttt tatgggtgtg aatgctttat aacaaacttt tattctgagg atacagcaaa    9060
acatagctcc atacaatgca aaacaatact caatttcaaa tgtgtttatg atatgaactt    9120
gcagtgttcc tcaaagatct tccatgaata acttaatggc ctggcagatg acagaggaat    9180
tgtgaaattc agctggagga gtgttcatgg ttcgagggac aatcataata tacaatagca    9240
aatatatttc agttatagaa gctattgttc tgtattgaaa taatagaatt gacaaacagt    9300
aaagaaacca ttctgacctc tgtaaagcac tgtttgattt aaaaatgggg gaaaaaagta    9360
caacataatt cttcaggaca tacatagaga tcactgcaat ctctgttaag cagaattact    9420
ttcctatacc actagctgaa gtttagtcag tgccatttc ttttgtttct ctccttcctt    9480
ttgtgaaaac atatatactg tggaaatcta cattctcctt gccaagtctg aggacttaag    9540
acaagatggt agtgcaaata atattttttt gctggatgtc tacaccacag gtatcaactg    9600
attttttttg tttcattttg tttttaatca cgtcttttgc ttctatttca gccactaaga    9660
aagtctgaaa atcttgcctg cttttttgtga tgatagatgt gcttcccagt aaatgttatc    9720
tctacctatg aaatgcatgt cagtctgcag aaagagaaag gagattggga ataggttttc    9780
tcagatgcac ttctctgtca tctggtgtca atcaaacact aataatttgt gtatagatat    9840
cttatatata tatatatatt tggaatttgc aggttggcat agttcagata gtcctgtcac    9900
attgtaatat cctggtgaga taacaaggaa aagagagacc gtttcggctc ttactaaggc    9960
agggaactgc ttaccagaca gggaggttct ggagatgaca tccagcatga aaagcacact    10020
tccaaatact taaggtatc aagtctaact tgtcagacag gctccagaat aacttctgtc    10080
ctaatgctac agaaaagggg gaaggtatcc accatggcca aaattgtcag ccattttgtc    10140
tcagcaaaca gcagatctgg tcagtaagga caagattctt ccaaagcaac catgccatat    10200
ataattaagc atgtgtaatt aattaataaa aatataatt tagtgtattt cctcctttgg    10260
atgttatgaa gaaatgcttt tattaacaat tcaccataat ctgtcctaag agtagtgaat    10320
aacaacaggc tgcttctcac cctgtggttg ggtgtaccag tgagccagag ctaaacgcca    10380
cgttcctct tttgtatccc atagcagaga gggtctccat ttcatttctg tagctcgaaa    10440
agttgtagtg gatttacact acaagttgtg gtagtggagg tctgccggag tggcctctgt    10500
gaacagagcc cagcagctgt cccgtgtcct caaagggag ctgccactgg ccagagctga    10560
gccagtgatc gatgctagat gtacctcagg aggagcaata tgtaagaaca actgctgtac    10620
aatggtagtt gggagaggtg agtgagaaaa tgtgagagaa acagccctga tgacactgag    10680
gtcagtgcgg aggagggcag gaggtgttcc aggtgtagaa cagaagttcc ctgcagccca    10740
agagaggccc atggtggagc actctgaccc tctgcagccc atggtatatc atataaacct    10800
```

```
cagttctgtg acattatttt aactccatat ccctttctg ttcagggtca ctttgagttc       10860
acagccattt ctttatattt ctccaatatc agccttccat tgctacatat gagacttgga       10920
cagtacatct gattcagtca aatctgcctt cagaacgtcc ctgaagccct tcttagacag       10980
tctcaattct ccttcccttc atctcttta tcatacatgg accacggacc tgtccagacc       11040
tgagtcatat gtccatcttt acgtccatct ctatgtcttg tactttaaga caaataaaat       11100
atcaaggaaa ttgatgcagt tatgtcagtt atcactgtca tagtatcgtg ctgcaaatat       11160
aagatgagaa tgatcccaaa ggcttttaa agctgctcta tttgacttcc acatagtgtc       11220
ctgattccag acctacagaa cagttttgta tgcatttgac ttgcagagct ttgttttgtg       11280
agtcttataa aagccatttt tcctctccaa gaagtagccg gtggtttaaa acaatgtaga       11340
ttaagtgtgg agcatgagaa tttctgcttt tctgtcagat gagaaggata tactacactc       11400
tttcccaatg gaagaccagc tgcaagcaac aaaaattgtc catgaacaaa tgagatcttg       11460
atcagaacag gctgtcatca tagtgttgtc agcatacctg catagttggt ttgacttggg       11520
ggtctagaga gagtaagcaa caatcttctt gcagttggaa ggttacctgg ataggtggc       11580 aatggattgc cctgcccagc acagctgtgc aaagcagtac aaatagtttt gtcacacatt       11640
gtttgacaat gcttgtccca agaaaaggtc agctaaggct ctgctgccct ttcctatgcc       11700
aggcatttca ttgtgggtct gtccctaaac caacagtctc atgaataaag actcggagac       11760
ctgaaagtta taaagcact ttttatccaa aaggatatga agtccaggtg agctcacagg       11820
tcaaagcctc ttatccaatc actaaaacct actcagaact tgactcga                   11868
```

<210> SEQ ID NO 20
<211> LENGTH: 10021
<212> TYPE: DNA
<213> ORGANISM: Artificial Sequence
<220> FEATURE:
<223> OTHER INFORMATION: Description of Artificial Sequence: Synthetic
      pSIN-3.9-OM-CTLA4-Fc vector polynucleotide

<400> SEQUENCE: 20

```
ctagactagg atccccgtg ctgcagaacc gagcggctat tgacttcttg ctcctagctc        60
acggccatgg ctgtgaggac attgcgggaa tgtgttgttt caatctgagt gatcacagtg       120
agtctataca gaagaagttc cagctaatga aggaacatgt caataagatc ggcgtgaaca       180
acgacccaat cggaagttgg ctgcgaggat tattcggagg aataggagaa tgggccgtac       240
acttgctgaa aggactgctt tggggcttg tagttatctt gttgctagta gtatgcttgc       300
cttgcctttt gcaatgtgta tctagtagta ttcgaaagat gattgataat tcactcggct       360
atcgcgagga atataaaaaa attacaggag gcttataagc agcccgaaag aagagcgtag       420
gcgagttctt gtattccgtg tgatagctgg ttggattggt aattgatcgg ctggcacgcg       480
gaatatagga ggtcgctgaa tagtaaactt gtagacttgg ctacagcata gagtatcttc       540
tgtagctctg atgactgcta ggaaataatg ctacggataa tgtggggagg caaggcttg       600 cgaatcgggt tgtaacgggc aaggcttgac tgaggggaca atagcatgtt taggcgaaaa       660
gcggggcttc ggttgtacgc ggttaggagt cccctcagga tatagtagtt tcgcttttgc       720
ataggggagg gacggattg gacgaaccac tgaattccgc attgcagaga tattgtattt       780
aagtgcctag ctcgatacaa taaacgccat tgaccattc accacattgg tgtgcacctg       840
ggttgatggc cggaccgttg attccctgrc gactacgagc acatgcatga agcagaaggc       900
ttcatttggt gaccccgacg tgatcgttag ggaatacgcg ctcactggcc gtcgttttac       960
```

```
aacgtcgtga ctgggaaaac cctggcgtta cccaacttaa tcgccttgca gcacatcccc    1020
ctttcgccag ctggcgtaat agcgaagagg cccgcaccga tcgcccttcc caacagttgc    1080
gcagcctgaa tggcgaatgg aaattgtaag cgttaatatt ttgttaaaat tcgcgttaaa    1140
tttttgttaa atcagctcat tttttaacca ataggccgaa atcggcaaaa tcccttataa    1200
atcaaaagaa tagaccgaga tagggttgag tgttgttcca gtttggaaca agagtccact    1260
attaaagaac gtggactcca acgtcaaagg gcgaaaaacc gtctatcagg gcgatggccc    1320
actacgtgaa ccatcaccct aatcaagttt ttggggtcg aggtgccgta aagcactaaa     1380
tcggaaccct aaagggagcc cccgatttag agcttgacgg ggaaagccgg cgaacgtggc    1440
gagaaaggaa gggaagaaag cgaaaggagc gggcgctagg gcgctggcaa gtgtagcggt    1500
cacgctgcgc gtaaccacca cacccgccgc gcttaatgcg ccgctacagg gcgcgtcagg    1560
tggcactttt cggggaaatg tgcgcggaac ccctatttgt ttattttttct aaatacattc   1620 aaatatgtat ccgctcatga gacaataacc ctgataaatg cttcaataat attgaaaaag    1680
gaagagtatg agtattcaac atttccgtgt cgcccttatt ccctttttg cggcattttg     1740 ccttcctgtt tttgctcacc cagaaacgct ggtgaaagta aaagatgctg aagatcagtt    1800
gggtgcacga gtgggttaca tcgaactgga tctcaacagc ggtaagatcc ttgagagttt    1860
tcgccccgaa gaacgttttc caatgatgag cactttttaaa gttctgctat gtggcgcggt   1920
attatcccgt attgacgccg ggcaagagca actcggtcgc cgcatacact attctcagaa    1980
tgacttggtt gagtactcac cagtcacaga aaagcatctt acggatggca tgacagtaag    2040
agaattatgc agtgctgcca taaccatgag tgataacact gcggccaact tacttctgac    2100
aacgatcgga ggaccgaagg agctaaccgc ttttttgcac aacatggggg atcatgtaac    2160
tcgccttgat cgttgggaac cggagctgaa tgaagccata ccaaacgacg agcgtgacac    2220
cacgatgcct gtagcaatgg caacaacgtt gcgcaaacta ttaactggcg aactacttac    2280
tctagcttcc cggcaacaat taatagactg gatggaggcg gataaagttg caggaccact    2340
tctgcgctcg gcccttccgg ctggctggtt tattgctgat aaatctggag ccggtgagcg    2400
tgggtctcgc ggtatcattg cagcactggg gccagatggt aagccctccc gtatcgtagt    2460
tatctacacg acggggagtc aggcaactat ggatgaacga atagacaga tcgctgagat     2520 aggtgcctca ctgattaagc attggtaact gtcagaccaa gtttactcat atatacttta    2580
gattgattta aaacttcatt tttaatttaa aaggatctag gtgaagatcc ttttttgataa    2640 tctcatgacc aaaatccctt aacgtgagtt ttcgttccac tgagcgtcag accccgtaga    2700
aaagatcaaa ggatcttctt gagatccttt ttttctgcgc gtaatctgct gcttgcaaac    2760
aaaaaaacca ccgctaccag cggtggtttg tttgccggat caagagctac caactctttt    2820
tccgaaggta actggcttca gcagagcgca gataccaaat actgtccttc tagtgtagcc    2880
gtagttaggc caccacttca agaactctgt agcaccgcct acatacctcg ctctgctaat    2940
cctgttacca gtggctgctg ccagtggcga taagtcgtgt cttaccgggt tggactcaag    3000
acgatagtta ccggataagg cgcagcggtc gggctgaacg gggggttcgt gcacacagcc    3060
cagcttggag cgaacgacct acaccgaact gagataccta cagcgtgagc tatgagaaag    3120
cgccacgctt cccgaaggga gaaaggcgga caggtatccg gtaagcggca gggtcggaac    3180
aggagagcgc acgagggagc ttccaggggg aaacgcctgg tatctttata gtcctgtcgg    3240
gtttcgccac ctctgacttg agcgtcgatt tttgtgatgc tcgtcagggg gcggagccta    3300
atggaaaaac gccagcaacg cggccttttt acggttcctg gccttttgct ggccttttgc    3360
```

```
tcacatgttc tttcctgcgt tatcccctga ttctgtggat aaccgtatta ccgcctttga   3420
gtgagctgat accgctcgcc gcagccgaac gaccgagcgc agcgagtcag tgagcgagga   3480
agcggaagag cgcccaatac gcaaaccgcc tctccccgcg cgttggccga ttcattaatg   3540
cagctggcac gacaggtttc ccgactggaa agcgggcagt gagcgcaacg caattaatgt   3600
gagttagctc actcattagg caccccaggc tttacacttt atgcttccgg ctcgtatgtt   3660
gtgtggaatt gtgagcggat aacaatttca cacaggaaac agctatgacc atgattacgc   3720
caagcgcgca ttggtaattg atcggctggc acgcggaata taggaggtcg ctgaatagta   3780
aacttgtaga cttggctaca gcatagagta tcttctgtag ctctgatgac tgctaggaaa   3840
taatgctacg gataatgtgg ggagggcaag gcttgcgaat cgggttgtaa cgggcaaggc   3900
ttgactgagg ggacaatagc atgtttaggc gaaaagcggg gcttcggttg tacgcggtta   3960
ggagtcccct caggatatag tagtttcgct tttgcatagg gagggggaaa tgtagtctta   4020
tgcaatactc ttgtagtctt gcaacatgct tatgtaacga tgagttagca acatgcctta   4080
taaggagaga aaaagcaccg tgcatgccga ttggtgggag taaggtggta tgatcgtggt   4140
atgatcgtgc cttgttagga aggcaacaga cgggtctaac acggattgga cgaaccactg   4200
aattccgcat tgcagagata ttgtatttaa gtgcctagct cgatacaata aacgccattt   4260
gaccattcac cacattggtg tgcacctggg ttgatggccg gaccgttgat tccctgrcga   4320
ctacgagcac atgcatgaag cagaaggctt catttggtga ccccgacgtg atcgttaggg   4380
aatagtggtc ggccacaggc ggcgtggcga tcctgtcctc atccgtctcg cttattcggg   4440
gagcggacga tgaccctagt agaggggct gcggcttagg agggcagaag ctgagtggcg   4500
tcggagggag ccctactgca gggggccaac ataccctacc gagaactcag agagtcgttg   4560
gaagacggga aggaagcccg acgactgagc ggtccacccc aggcgtgatt ccggttgctc   4620
tgcgtgattc cggtcgcccg gtggatcaag catggaagcc gtcataaagg tgatttcgtc   4680
cgcgtgtaag acctattgcg ggaaaacctc tccttctaag aaggaaatag gggctatgtt   4740
gtccctgtta caaaggaag ggttgcttac gtcccctca gacttatatt ccccggggtc   4800
ctgggatccc attaccgcgg cgctctctca gcgggctatg gtacttggaa atcgggaga   4860
gttaaaaacc tggggattgg ttttgggggc attgaaggcg gctcgaggtc gacggtatcg   4920
ataagcttgc agtccaaggc tttgtctgtg tacccagtga aatccttcct ctgttacata   4980
aagcccagat aggactcaga aatgtagtca ttccagcccc cctcttcctc agatctggag   5040
cagcacttgt ttgcagccag tcctccccaa aatgcacaga cctcgccgag tggagggaga   5100
tgtaaacagc gaaggttaat tacctccttg tcaaaaacac tttgtggtcc atagatgttt   5160
ctgtcaatct tacaaaacag aaccgagagg cagcgagcac tgaagagcgt gttcccatgc   5220
tgagttaatg agacttggca gctcgctgtg cagagatgat ccctgtgctt catgggaggc   5280
tgtaacctgt ctccccatcg ccttcacacc gcagtgctgt cctggacacc tcaccctcca   5340
taagctgtag gatgcagctg cccagggatc aagagacttt tcctaaggct cttaggactc   5400
atctttgccg ctcagtagcg tgcagcaatt actcatccca actatactga atgggtttct   5460
gccagctctg cttgtttgtc aataagcatt tcttcatttt gcctctaagt ttctctcagc   5520
agcaccgctc tggtgacct gagtggccac ctggaacccg aggggcacag ccaccacctc   5580
cctgttgctg ctgctccagg gactcatgtg ctgctggatg gggggaagca tgaagttcct   5640
cacccagaca cctgggttgc aatggctgca gcgtgctctt cttggtatgc agattgtttc   5700
```

```
cagccattac ttgtagaaat gtgctgtgga agcccttttgt atctcttttct gtggcccttc   5760 agcaaaagct gtgggaaagc tctgaggctg cttttcttggg tcgtggagga attgtatgtt   5820
ccttctttaa caaaaattat ccttaggaga gagcactgtg caagcattgt gcacataaaa   5880
caattcaggt tgaaagggct ctctggaggt ttccagcctg actactgctc gaagcaaggc   5940
caggttcaaa gatggctcag gatgctgtgt gccttcctga ttatctgtgc caccaatgga   6000
ggagattcac agccactctg cttcccgtgc cactcatgga gaggaatatt cccttatatt   6060
cagatagaat gttatccttt agctcagcct tccctataac cccatgaggg agctgcagat   6120
ccccatactc tcccccttctc tggggtgaag gccgtgtccc ccagcccccc ttcccaccct   6180
gtgccctaag cagcccgctg gcctctgctg gatgtgtgcc tatatgtcaa tgcctgtcct   6240
tgcagtccag cctgggacat ttaattcatc accagggtaa tgtggaactg tgtcatcttc   6300
ccctgcaggg tacaaagttc tgcacggggt cctttcggtt caggaaaacc ttcactggtg   6360
ctacctgaat caagctctat ttaataagtt cataagcaca tggatgtgtt ttcctagaga   6420
tacgttttaa tggtatcagt gatttttatt tgctttgttg cttacttcaa acagtgcctt   6480
tgggcaggag gtgagggacg ggtctgccgt tggctctgca gtgatttctc caggcgtgtg   6540
gctcaggtca gatagtggtc actctgtggc cagaagaagg acaaagatgg aaattgcaga   6600
ttgagtcacg ttaagcaggc atcttggagt gatttgaggc agtttcatga agagctacg   6660 accacttatt gttgttttcc ccttttacaa cagaagtttt catcaaaata acgtggcaaa   6720
gcccaggaat gtttgggaaa agtgtagtta aatgttttgt aattcatttg tcggagtgct   6780
accagctaag aaaaaagtcc tacctttggt atggtagtcc tgcagagaat acaacatcaa   6840
tattagtttg gaaaaaaaca ccaccaccac cagaaactgt aatggaaaat gtaaaccaag   6900
aaattccttg ggtaagagag aaaggatgtc gtatactggc caagtcctgc ccagctgtca   6960
gcctgctgac cctctgcagt tcaggaccat gaaacgtggc actgtaagac gtgtcccctg   7020
cctttgcttg cccacagatc tctgcccttg tgctgactcc tgcacacaag agcattctccc   7080 tgtagccaaa cagcgattag ccataagctg cacctgactt tgaggattaa gagtttgcaa   7140
ttaagtggat tgcagcagga gatcagtggc agggttgcag atgaaatcct ttctagggg   7200 tagctaaggg ctgagcaacc tgtcctacag cacaagccaa accagccaag ggttttcctg   7260
tgctgttcac agaggcaggg ccagctggag ctggaggagg ttgtgctggg acccttctcc   7320
ctgtgctgag aatggagtga tttctgggtg ctgttcctgt ggcttgcact gagcagctca   7380
agggagatcg gtgctcctca tgcagtgcca aaactcgtgt ttgatgcaga agatggatg   7440 tgcacctccc tcctgctaat gcagccgtga gcttatgaag gcaatgagcc ctcagtgcag   7500
caggagctgt agtgcactcc tgtaggtgct agggaaaatc tctggttccc agggatgcat   7560
tcataagggc aatatatctt gaggctgcgc caaatctttc tgaaatattc atgcgtgttc   7620
ccttaattta tagaaacaaa cacagcagaa taattattcc aatgcctccc ctcgaaggaa   7680
acccatattt ccatgtagaa atgtaaccta tatacacaca gccatgctgc atccttcaga   7740
acgtgccagt gctcatctcc catggcaaaa tactacaggt attctcacta tgttggacct   7800
gtgaaaggaa ccatggtaag aaacttcggt taaaggtatg gctgcaaaac tactcatacc   7860
aaaacagcag agctccagac ctcctcttag gaaagagcca cttggagagg gatggtgtga   7920
aggctggagg tgagagacag agcctgtccc agttttcctg tctctatttt ctgaaacgtt   7980
tgcaggagga aaggacaact gtactttcag gcatagctgg tgccctcacg taaataagtt   8040
ccccgaactt ctgtgtcatt tgttcttaag atgctttggc agaacacttt gagtcaattc   8100
```

```
gcttaactgt gactaggtct gtaaataagt gctccctgct gataaggttc aagtgacatt    8160
tttagtggta tttgacagca tttaccttgc tttcaagtct tctaccaagc tcttctatac    8220
ttaagcagtg aaaccgccaa gaaacccttc cttttatcaa gctagtgcta ataccatta     8280 acttcatagg ttagatacgg tgctgccagc ttcacctggc agtggttggt cagttctgct    8340
ggtgacaaag cctccctggc ctgtgctttt acctagaggt gaatatccaa gaatgcagaa    8400
ctgcatggaa agcagagctg caggcacgat ggtgctgagc cttagctgct tcctgctggg    8460
agatgtggat gcagagacga atgaaggacc tgtcccttac tcccctcagc attctgtgct    8520
atttagggtt ctaccagagt ccttaagagg tttttttttt ttttggtcca aaagtctgtt    8580
tgtttggttt tgaccactga gagcatgtga cacttgtctc aagctattaa ccaagtgtcc    8640
agccaaaatc aattgcctgg gagacgcaga ccattacctg gaggtcagga cctcaataaa    8700
tattaccagc ctcattgtgc cgctgacaga ttcagctggc tgctccgtgt tccagtccaa    8760
cagttcggac gccacgtttg tatatatttg caggcagcct cggggggacc atctcaggag    8820
cagagcaccg gcagccgcct gcagagccgg gcagtacctc aacatgggtg tactgctcac    8880
acagaggacg ctgctcagtc tggtccttgc actcctgttt ccaagcatgg cgagcatggc    8940
aatgcacgtg gcccagcctg ctgtggtact ggccagcagc cgaggcatcg cyagctttgt    9000
gtgtgagtat gcatctccag gcaaagccac tgaggtccgg gtgacagtgc ttcggcaggc    9060
tgacagccag gtgactgaag tctgtgcggc aacctacatg atggggaatg agttgacctt    9120
cctagatgat tccatctgca cgggcacctc cagtggaaat caagtgaacc tcactatcca    9180
aggactgagg gccatggaca cgggactcta catctgcaag gtggagctca tgtacccacc    9240
gccatactac ctgggcatag gcaacggaac ccagatttat gtaattgatc cagaaccgtg    9300
cccagattct gatcaggagc ccaaatcttc tgacaaaact cacacatccc accgtcccc    9360 agcacctgaa ctcctggggg gatcgtcagt cttcctcttc ccccaaaaac ccaaggacac    9420
cctcatgatc tcccggaccc ctgaggtcac atgcgtggtg gtggacgtga gccacgaaga    9480
ccctgaggtc aagttcaact ggtacgtgga cggcgtggag gtgcataatg ccaagacaaa    9540
gccgcgggag gagcagtaca acagcacgta ccgggtggtc agcgtcctca ccgtcctgca    9600
ccaggactgg ctgaatggca aggagtacaa gtgcaaggtc tccaacaaag ccctcccagc    9660
ccccatcgag aaaaccatct ccaaagccaa agggcagccc cgagaaccac aggtgtacac    9720
cctgccccca tcccgggatg agctgaccaa gaaccaggtc agcctgacct gcctggtcaa    9780
aggcttctat cccagcgaca tcgccgtgga gtgggagagc aatgggcagc cggagaacaa    9840
ctacaagacc acgcctcccg tgctggactc cgacggctcc ttcttcctct acagcaagct    9900
caccgtggac aagagcaggt ggcagcaggg gaacgtcttc tcatgctccg tgatgcatga    9960
ggctctgcac aaccactaca cgcagaagag cctctccctg tctccgggta aatgaggaat   10020
t                                                                   10021

<210> SEQ ID NO 21
<211> LENGTH: 7350
<212> TYPE: DNA
<213> ORGANISM: Artificial Sequence
<220> FEATURE:
<223> OTHER INFORMATION: Description of Artificial Sequence: Synthetic
      pSIN-1.8-OM-IFNa-2B vector polynucleotide

<400> SEQUENCE: 21
tcgagatcaa ttgctagact aggatccccc gtgctgcaga accgagcggc tattgacttc      60
```

```
ttgctcctag ctcacggcca tggctgtgag acattgcgg gaatgtgttg tttcaatctg      120
agtgatcaca gtgagtctat acagaagaag ttccagctaa tgaaggaaca tgtcaataag     180
atcggcgtga acaacgaccc aatcggaagt tggctgcgag gattattcgg aggaatagga     240
gaatgggccg tacacttgct gaaaggactg cttttggggc ttgtagttat cttgttgcta     300
gtagtatgct tgccttgcct tttgcaatgt gtatctagta gtattcgaaa gatgattgat     360
aattcactcg gctatcgcga ggaatataaa aaaattacag gaggcttata agcagcccga     420
aagaagagcg taggcgagtt cttgtattcc gtgtgatagc tggttggatt ggtaattgat     480
cggctggcac gcggaatata ggaggtcgct gaatagtaaa cttgtagact ggctacagc      540 atagagtatc ttctgtagct ctgatgactg ctaggaaata atgctacgga taatgtgggg     600
agggcaaggc ttgcgaatcg ggttgtaacg ggcaaggctt gactgagggg acaatagcat     660
gtttaggcga aaagcggggc ttcggttgta cgcggttagg agtcccctca ggatatagta     720
gtttcgcttt tgcataggga gggggacgga ttggacgaac cactgaattc cgcattgcag     780
agatattgta tttaagtgcc tagctcgata caataaacgc catttgacca ttcaccacat     840
tggtgtgcac ctgggttgat ggccggaccg ttgattccct grcgactacg agcacatgca     900
tgaagcagaa ggcttcatt ggtgaccccg acgtgatcgt tagggaatac gcgctcactg      960
gccgtcgttt tacaacgtcg tgactgggaa accctggcg ttaccaact taatcgcctt      1020 gcagcacatc ccccttttcgc cagctggcgt aatagcgaag aggcccgcac cgatcgccct    1080
tcccaacagt tgcgcagcct gaatggcgaa tggaaattgt aagcgttaat attttgttaa    1140
aattcgcgtt aaattttttgt taaatcagct cattttttaa ccataggcc gaaatcggca    1200 aaatccctta taaatcaaaa gaatagaccg agatagggtt gagtgttgtt ccagtttgga    1260
acaagagtcc actattaaag aacgtggact ccaacgtcaa agggcgaaaa accgtctatc    1320
agggcgatgg cccactacgt gaaccatcac cctaatcaag ttttttgggg tcgaggtgcc    1380
gtaaagcact aaatcggaac cctaaaggga gcccccgatt tagagcttga cggggaaagc    1440
cggcgaacgt ggcgagaaag gaagggaaga agcgaaagg agcgggcgct agggcgctgg     1500
caagtgtagc ggtcacgctg cgcgtaacca ccacacccgc cgcgcttaat gcgccgctac    1560
agggcgcgtc aggtgcact tttcggggaa atgtgcgcgg aaccccctatt tgtttatttt    1620 tctaaataca ttcaaatatg tatccgctca tgagacaata accctgataa atgcttcaat    1680
aatattgaaa aaggaagagt atgagtattc aacatttccg tgtcgccctt attccctttt    1740
ttgcggcatt ttgccttcct gttttttgctc acccagaaac gctggtgaaa gtaaaagatg    1800
ctgaagatca gttgggtgca cgagtgggtt acatcgaact ggatctcaac agcggtaaga    1860
tccttgagag ttttcgcccc gaagaacgtt ttccaatgat gagcactttt aaagttctgc    1920
tatgtggcgc ggtattatcc cgtattgacg ccgggcaaga gcaactcggt cgccgcatac    1980
actattctca gaatgacttg gttgagtact caccagtcac agaaaagcat cttacggatg    2040
gcatgacagt aagagaatta tgcagtgctg ccataaccat gagtgataac actgcggcca    2100
acttacttct gacaacgatc ggaggaccga aggagctaac cgcttttttg cacaacatgg    2160
gggatcatgt aactcgcctt gatcgttggg aaccggagct gaatgaagcc ataccaaacg    2220
acgagcgtga caccacgatg cctgtagcaa tggcaacaac gttgcgcaaa ctattaactg    2280
gcgaactact tactctagct tcccggcaac aattaataga ctggatggag gcggataaag    2340
ttgcaggacc acttctgcgc tcggcccttc cggctggctg gtttattgct gataaatctg    2400
```

```
gagccggtga gcgtgggtct cgcggtatca ttgcagcact ggggccagat ggtaagccct    2460
cccgtatcgt agttatctac acgacgggga gtcaggcaac tatggatgaa cgaaatagac    2520
agatcgctga gataggtgcc tcactgatta agcattggta actgtcagac caagttta ct   2580
catatatact ttagattgat ttaaaacttc atttttaatt taaaaggatc taggtgaaga    2640
tcctttttga taatctcatg accaaaatcc cttaacgtga gttttcgttc cactgagcgt    2700
cagaccccgt agaaaagatc aaaggatctt cttgagatcc ttttttttctg cgcgtaatct   2760
gctgcttgca aacaaaaaaa ccaccgctac cagcggtggt ttgtttgccg gatcaagagc    2820
taccaactct ttttccgaag gtaactggct tcagcagagc gcagatacca aatactgtcc    2880
ttctagtgta gccgtagtta ggccaccact tcaagaactc tgtagcaccg cctacatacc    2940
tcgctctgct aatcctgtta ccagtggctg ctgccagtgg cgataagtcg tgtcttaccg    3000
ggttggactc aagacgatag ttaccggata aggcgcagcg gtcgggctga acggggggtt    3060
cgtgcacaca gcccagcttg gagcgaacga cctacaccga actgagatac ctacagcgtg    3120
agctatgaga aagcgccacg cttcccgaag ggagaaaggc ggacaggtat ccggtaagcg    3180
gcagggtcgg aacaggagag cgcacgaggg agcttccagg gggaaacgcc tggtatcttt    3240
atagtcctgt cgggtttcgc cacctctgac ttgagcgtcg attttttgtga tgctcgtcag   3300
gggggcggag cctatggaaa aacgccagca acgcggcctt tttacggttc ctggccttt t   3360
gctggccttt tgctcacatg ttctttcctg cgttatcccc tgattctgtg ataaccgta    3420
ttaccgcctt tgagtgagct gataccgctc gccgcagccg aacgaccgag cgcagcgagt    3480
cagtgagcga ggaagcggaa gagcgcccaa tacgcaaacc gcctctcccc gcgcgttggc    3540
cgattcatta atgcagctgg cacgacaggt ttcccgactg gaaagcgggc agtgagcgca    3600
acgcaattaa tgtgagttag ctcactcatt aggcaccccca ggctttacac tttatgcttc   3660
cggctcgtat gttgtgtgga attgtgagcg ataacaatt tcacacagga aacagctatg     3720
accatgatta cgccaagcgc gcattggtaa ttgatcggct ggcacgcgga atataggagg    3780
tcgctgaata gtaaacttgt agacttggct acagcataga gtatcttctg tagctctgat    3840
gactgctagg aaataatgct acggataatg tggggagggc aaggcttgcg aatcgggttg    3900
taacgggcaa ggcttgactg aggggacaat agcatgttta ggcgaaaagc ggggcttcgg    3960
ttgtacgcgg ttaggagtcc cctcaggata tagtagtttc gcttttgcat agggaggggg    4020
aaatgtagtc ttatgcaata ctcttgtagt cttgcaacat gcttatgtaa cgatgagtta    4080
gcaacatgcc ttataaggag agaaaaagca ccgtgcatgc cgattggtgg gagtaaggtg    4140
gtatgatcgt ggtatgatcg tgccttgtta ggaaggcaac agacgggtct aacacggatt    4200
ggacgaacca ctgaattccg cattgcagag atattgtatt taagtgccta gctcgataca    4260
ataaacgcca tttgaccatt caccacattg gtgtgcacct gggttgatgg ccggaccgtt    4320
gattccctgr cgactacgag cacatgcatg aagcagaagg cttcatttgg tgaccccgac    4380
gtgatcgtta gggaatagtg gtcggccaca ggcggcgtgg cgatcctgtc ctcatccgtc    4440
tcgcttattc ggggagcgga cgatgaccct agtagagggg gctgcggctt aggagggcag    4500
aagctgagtg gcgtcggagg gagccctact gcaggggggcc aacatacccct accgagaact   4560
cagagagtcg ttggaagacg ggaaggaagc ccgacgactg agcggtccac cccaggcgtg    4620
attccggttg ctctgcgtga ttccggtcgc ccggtggatc aagcatggaa gccgtcataa    4680
aggtgatttc gtccgcgtgt aagacctatt gcgggaaaac ctctccttct aagaggaaa    4740
tagggggctat gttgtccctg ttacaaaagg aagggttgct tacgtccccc tcagacttat   4800
```

```
attccccggg gtcctgggat cccattaccg cggcgctctc tcagcgggct atggtacttg    4860
gaaaatcggg agagttaaaa acctggggat tggttttggg ggcattgaag gcggctcgac    4920
ggatccgtta accctagaac tagtggatct ctgcccttgt gctgactcct gcacacaaga    4980
gcatttccct gtagccaaac agcgattagc cataagctgc acctgacttt gaggattaag    5040
agtttgcaat taagtggatt gcagcaggag atcagtggca gggttgcaga tgaaatcctt    5100
ttctaggggt agctaagggc tgagcaacct gtcctacagc acaagccaaa ccagccaagg    5160
gttttcctgt gctgttcaca gaggcagggc cagctggagc tggaggaggt tgtgctggga    5220
cccttctccc tgtgctgaga atggagtgat ttctgggtgc tgttcctgtg gcttgcactg    5280
agcagctcaa gggagatcgg tgctcctcat gcagtgccaa aactcgtgtt tgatgcagaa    5340
agatggatgt gcacctccct cctgctaatg cagccgtgag cttatgaagg caatgagccc    5400
tcagtgcagc aggagctgta gtgcactcct gtaggtgcta gggaaaatct ctggttccca    5460
gggatgcatt cataagggca atatatcttg aggctgcgcc aaatcttcct gaaatattca    5520
tgcgtgttcc cttaatttat agaaacaaac acagcagaat aattattcca atgcctcccc    5580
tcgaaggaaa cccatatttc catgtagaaa tgtaacctat atacacacag ccatgctgca    5640
tccttcagaa cgtgccagtg ctcatctccc atggcaaaat actacaggta ttctcactat    5700
gttggacctg tgaaaggaac catggtaaga aacttcggtt aaaggtatgg ctgcaaaact    5760
actcatacca aaacagcaga gctccagacc tcctcttagg aaagagccac ttggagaggg    5820
atggtgtgaa ggctggaggt gagagacaga gcctgtccca gttttcctgt ctctattttc    5880
tgaaacgttt gcaggaggaa aggacaactg tactttcagg catagctggt gccctcacgt    5940
aaataagttc cccgaacttc tgtgtcattt gttcttaaga tgctttggca gaacactttg    6000
agtcaattcg cttaactgtg actaggtctg taaataagtg ctccctgctg ataaggttca    6060
agtgacattt ttagtggtat ttgacagcat ttaccttgct ttcaagtctt ctaccaagct    6120
cttctatact taagcagtga aaccgccaag aaacccttcc ttttatcaag ctagtgctaa    6180
ataccattaa cttcataggt tagatacggt gctgccagct tcacctggca gtggttggtc    6240
agttctgctg gtgacaaagc ctccctggcc tgtgctttta cctagaggtg aatatccaag    6300
aatgcagaac tgcatggaaa gcagagctgc aggcacgatg gtgctgagcc ttagctgctt    6360
cctgctggga gatgtggatg cagagacgaa tgaaggacct gtcccttact cccctcagca    6420
ttctgtgcta tttagggttc taccagagtc cttaagaggt ttttttttt tttggtccaa    6480 aagtctgttt gtttggtttt gaccactgag agcatgtgac acttgtctca agctattaac    6540
caagtgtcca gccaaaatca attgcctggg agacgcagac cattacctgg aggtcaggac    6600
ctcaataaat attaccagcc tcattgtgcc gctgacagat tcagctggct gctccgtgtt    6660
ccagtccaac agttcggacg ccacgtttgt atatatttgc aggcagcctc gggggggacca    6720 tctcaggagc agagcaccgg cagccgcctg cagagccggg cagtacctca ccatggcttt    6780
gacctttgcc ttactggtgg ctctcctggt gctgagctgc aagagcagct gctctgtggg    6840
ctgcgatctg cctcagaccc acagcctggg cagcaggagg accctgatgc tgctggctca    6900
gatgaggaga atcagcctgt ttagctgcct gaaggatagg cacgattttg ctttcctca    6960 agaggagttt ggcaaccagt ttcagaaggc tgagaccatc cctgtgctgc acgagatgat    7020
ccagcagatc tttaacctgt ttagcaccaa ggatagcagc gctgcttggg atgagaccct    7080
gctggataag ttttacaccg agctgtacca gcagctgaac gatctggagg cttgcgtgat    7140
```

-continued

```
ccagggcgtg ggcgtgaccg agacccctct gatgaaggag gatagcatcc tggctgtgag   7200
gaagtacttt cagaggatca ccctgtacct gaaggagaag aagtacagcc cctgcgcttg   7260
ggaagtcgtg agggctgaga tcatgaggag ctttagcctg agcaccaacc tgcaagagag   7320
cttgaggtct aaggagtaaa aagtctaggc                                    7350
```

<210> SEQ ID NO 22
<211> LENGTH: 16051
<212> TYPE: DNA
<213> ORGANISM: Artificial Sequence
<220> FEATURE:
<223> OTHER INFORMATION: Description of Artificial Sequence: Synthetic
      16 kbp Ovalbumin polynucleotide

<400> SEQUENCE: 22

```
ctgcagccca ggcagcacac tagagcagag aaatctagtt agcagcaacc actggcagac     60
agaaatgatt atatagatta catactgacc ctagcctctt acactgccta ctgcatcact    120
gaaaggactg ggaagaagag agtgcaataa cgaagctgaa gctaggagga aggcaaggag    180
aactgaagct gactagggaa aaggggggatt aaaggtttaa gtgtctattc catagtttgc    240
tggtttgttt tttgtcaatt cctgaatcag taattttttat gttaattagc aaaaaattac    300
aaacactccc caagtcagga ctgttaccta aacagaagc tcagatcagc tgagccttag    360
tcttttggtc cctccctagg gaatgctgta tgtgtctctc tctccaggcc tgctcaaaat    420
tgacctcaga cccaaacttt tgctgaatct ccagtaccac ctcttttgct cctaactaga    480
taacaaagcc ctgagcgctt tgcttttagc aaagctttaa gtgccattac caactgcacc    540
tggagccttt acctacccct atggacccag gctctatatt taagctctgc cctgaacctt    600
cacttctttc ctgtcctaag ttagatgtac tagtatggtg tgtactatgt ctccagttca    660
aacacagctg tgcccatacc tggccaagga ctcctagtat gacctgggct gtgccttgct    720
gctaaggacc tgctgggtga ttgctggacc tgatcctaat cctgaattaa gaaatgattt    780
cttggcttga ctggatgtgc cctgtggtat gatactgcct tatgatttgg actcttgttt    840
gcagctgtgc aaatccctaa ggagcccagt ctctggccac ctggaatctt gtcactacca    900
aacttcctga gggactggtc ttgctctggg ttctgatctc tggacagtac tcacccttta    960
ctcagcccag gctcccagtt aagcccctttt ccaccctgcc aggctctccg ctccatccct   1020
agcaggggct ctcatgacag tgtgaccccc ccttactcag gtcagggcca cttgtgccac   1080 gttccttttcc tgtcttctgt ccctgccttg gctctaaagc agtgtgctac catccacaac   1140
cactgcatct ctctaaagta agcctctcct gagcccaagt ctctgtaacg aggaaggatg   1200
cactttgctc agaaggatgc gaggctgctt ctgagctctg agggcactga cctcccatga   1260
ggtacacccc ataccagga ccacaattca gcctgctgga accatcaact cctgctggag    1320
taaggccata gcaagaccag catccacctc cctgcagccc tgccctgccc agatattggg   1380
cctgctgatc tcaggatgca gacttgcttc tcagcttgac ctaagcattg ccctgtcttt   1440
atggacccac ctggttagca agttcagtgc agaaggaggc tgttggcatc tagctaattt   1500
tccacccaca ttactgtctg ctgactcatt ctacgtctct cccatcttgt tacaataata   1560
atttgggaga tcatattgaa ggtcttaata aagtcaaggc atgtgatatt ctctgctttg   1620
cctttgtttc tagaataagc cacttcatca tagaagatga aaatgctgat cagcagagat   1680
ctgtgcttga taaatccatg ctggcttttc ctatcacctt atattccttc atatgccttg   1740
agacacccaa ggaggccttg gatcagagct gtctgtagca gtcctaactg gtatacaatt   1800
```

```
agttgtacaa caggtagtga tccgcataat agttggcgtg agaaagtggg cctgtgctgt    1860
gtcaagcata gagtttgggt tccagtcctg ttctgcatgg cacatatgcc tgagcagctg    1920
ggtaatctct gcattccaat tggaaggcag gggcctgtag gcagttccca cttggcatgg    1980
gtgattgtac cacctgtgtc ctcatctgtg aagcatcatg ttttcattca aatatccttt    2040
tgtttgacag tagaaatgaa cagaattgtt ttttttttcct aagcaaattc tgcaagagct    2100
ctgaagaaca aggtgtcagt gaacttctag ctccatagat aggacttgca tcacatgtca    2160
tgccttgatt ggaggtctat ccgatactga caacttgtg gttccctgag ggaatgtaag    2220
attactgata ctactctctc tttatgttag ctacaataaa tggtaggtta agcaatagat    2280
acagagtttg agtgcctttc ttacaagcat catagtgaac aaatccactg gtgatctacc    2340
ttttcaataa ctacagagaa ttgtaatctc ttggattctc ctccttcccc gttctgaaaa    2400
tgtgttcttt ttttccaaat cagaaacctt cctcaaccac cctgactatt ctttggacat    2460
tgttttgttc ttgctcctaa ataggcttta taattttttgt aagtgaaagg ctttgcatgc    2520
aggtgaggct acaactcatt cagtaacaat gaggaagact gtcagatttt ggggaaaatt    2580
ctcccaccca accttttgct agccagtaag atgtaatcac tgaatgtcat gccacaaaga    2640
ccataccaac atcagaccac atatctacag gaagctttaa ggaatcattg actgtacagt    2700
gaagggtaaa tcaaattaaa atgaatgtga ggtctgatac gagatatcct catgggaatc    2760
aagagcaaag acaaatagtt tttcacagtc ttgtcatgat ctgtcacaga ccaaggcagc    2820
acagcaggca acaatgttgg tctcttcaga atggcacagc accgctgcag aaaaatgcca    2880
ggtggactat gaactcacat ccaaaggagc ttgacctgat acctgatttt cttcaaacag    2940
gggaaacaac acaatcccac aaaatagctc agagagaaac catcactgat ggctacagca    3000
ccaaggtatg caatggcaat ccattcgaca ttcatctgtg acctgagcaa aatgatttat    3060
ctctccatga atggttgctt cttttccctca tgaaaaggca atttccacac tcacaatatg    3120
caacaaagac aaacagagaa caattaatgt gctccttcct aatgtcaaaa ttgtagtggc    3180
aaagaggaga acaaaatctc aagttctgag taggttttag tgattggata agaggctttg    3240
acctgtgagc tcacctggac ttcatatcct tttggataaa aagtgctttt ataactttca    3300
ggtctccgag tctttattca tgagactgtt ggtttaggga cagacccaca atgaaatgcc    3360
tggcatagga aagggcagca gagccttagc tgaccttttc ttgggacaag cattgtcaaa    3420
caatgtgtga caaaactatt tgtactgctt tgcacagctg tgctgggcag ggcaatccat    3480
tgccacctat cccaggtaac cttccaactg caagaagatt gttgcttact ctctctagac    3540
ccccaagtca accaactat gcaggtatgc tgacaacgct atgatgacag cctgttctga    3600
tcaagatctc atttgttcat ggacaatttt tgttgcttgc agctggtctt ccattgggaa    3660
agagtgtagt atatccttct catctgacag aaaagcagaa attctcatgc tccacactta    3720
atctacattg ttttaaacca ccagctactt cttggagagg aaaaatggct tttataagac    3780
tcacaaaaca aagctctgca agtcaaatgc atacaaaact gttctgtagg tctgaatca    3840
ggacactatg tggaagtcaa atagagaagc tttaaaaaaa cctttgggat cattctcatc    3900
ttatatttgc agcacgatac tatgacagtg ataactgaca taactgcatc aatttccttg    3960
atattttatt tgtcttaaag tacaagacat agagatggac gtaaagatgg acatatgact    4020
caggtctgga caggtccgtg gtccatgtat gataaaagag atgaagggaa ggagaatgga    4080
gactgtctaa gaagggcttc agggacgttc tgaaggcaga tttgactgaa tcagatgtac    4140
tgtccaagtc tcatatgtag caatggaaga ctgatattgg agaaatataa agaaatggct    4200
```

```
gtgaactcaa agtgaccctg aacagaaaag ggatatggag ttaaaataat ggcacagaac    4260
tgaggtttat atgatatacc atgggctgca gagggtcaga gtgctccacc atgggcctct    4320
cttgggctgc agggaacttc tgttctacac ctggaacacc tcctgccctc ctccgcactg    4380
acctcagtgt catcagggct gtttctctca cattttctca ctcacctctc ccaactacca    4440
ttgtacagca gttgttctta catcttgctc ctcctgaggt gcatctagca tcgatcactg    4500
gctcagctct ggccagtggc agctcccttt gaggcacacg ggacagctgc tgggctctgt    4560
tcacagaggc cactccagca gacctccact accacaactt gtagtgtaaa tccactacaa    4620 cttttctgagc tacagaaatg aaatggagac cctctctgct atgggataca aaagaggaaa    4680
cgtggcgttt agtgctctgg ctcactggta cacccaacca cagggtgaga agcagcctgt    4740
tgttattcac tactcttagg acagattatg gtgaattgtt aataaaagca tttcttcata    4800
acatccaaag gaggaaatac actaaattat attttttatt tattaattac acatgcttaa    4860
ttatatatgg catggttgct ttgaaagaac cttgtcctta ctgaccagat ctgctgtttg    4920
ctgagacaaa atggctgaca attttggcca tggtggatac cttccccctt ttctgtagca    4980
ttaggacaga agttattctg gagcctgtct gacaagtcag acttgataac tttaagtatt    5040
tggaagtgtg cttttcatgc tggatgtcat ctccagaacc tccctgtctg gtaagcagtt    5100
ccctgcctta gtaagagccg aaacggtctc tcttttcctt gttatctcac caggatatta    5160
caatgtgaca ggactatctg aactacgcca acctgcaaat tccaaatata tatatatata    5220
tgtaagatat ctatacacaa attattagtg tttgattgac accagatgac agagaagtgc    5280
atctgagaaa acctattccc aatctccttt ctctttctgc agactgacat gcatttcata    5340
ggtagagata acatttactg ggaagcacat ctatcatcat aaaaagcagg caagattttc    5400
agactttctt agtggctgaa atagaagcaa aagacgtgat taaaaacaaa atgaaacaaa    5460
aaaaatcagt tgatacctgt ggtgtagaca tccagcaaaa aaatattatt tgcactacca    5520
tcttgtctta agtcctcaga cttggcaagg agaatgtaga tttctacagt atatatgttt    5580
tcacaaaagg aaggagagaa acaaagaaa atggcactga ctaaacttca gctagtggta    5640
taggaaagta attctgctta acagagattg cagtgatctc tatgtatgtc ctgaagaatt    5700
atgttgtact ttttttccccc attttttaaat caaacagtgc tttacagagg tcagaatggt    5760
ttctttactg tttgtcaatt ctattatttc aatacagaac aatagcttct ataactgaaa    5820
tatatttgct attgtatatt atgattgtcc ctcgaaccat gaacactcct ccagctgaat    5880
ttcacaattc ctctgtcatc tgccaggcca ttaagttatt catggaagat ctttgaggaa    5940
cactgcaagt tcatatcata aacacatttg aaattgagta ttgttttgca ttgtatggag    6000
ctatgttttg ctgtatcctc agaaaaaaag tttgttataa agcattcaca cccataaaaa    6060
gatagattta atattccag ctataggaaa gaaagtgcgt ctgctcttca ctctagtctc    6120
agttggctcc ttcacatgca tgcttcttta tttctcctat tttgtcaaga aaataatagg    6180
tcacgtcttg ttctcactta tgtcctgcct agcatggctc agatgcacgt tgtagataca    6240
agaaggatca aatgaaacag acttctggtc tgttactaca accatagtaa taagcacact    6300
aactaataat tgctaattat gttttccatc tctaaggttc ccacattttt ctgttttctt    6360
aaagatccca ttatctggtt gtaactgaag ctcaatggaa catgagcaat atttcccagt    6420
cttctctccc atccaacagt cctgatggat tagcagaaca ggcagaaaac acattgttac    6480
ccagaattaa aaactaatat ttgctctcca ttcaatccaa aatggaccta ttgaaactaa    6540
```

-continued

```
aatctaaccc aatcccatta aatgatttct atggcgtcaa aggtcaaact tctgaaggga      6600
acctgtgggt gggtcacaat tcaggctata tattccccag ggctcagcca gtgtctgtac      6660
atacagctag aaagctgtat tgcctttagc agtcaagctc gaaaggtaag caactctctg      6720
gaattacctt ctctctatat tagctcttac ttgcacctaa actttaaaaa attaacaatt      6780
attgtgctat gtgttgtatc tttaagggtg aagtacctgc gtgataccc ctataaaaac      6840 ttctcacctg tgtatgcatt ctgcactatt ttattatgtg taaaagcttt gtgtttgttt      6900
tcaggaggct tattctttgt gcttaaaata tgttttaat ttcagaacat cttatcctgt       6960
cgttcactat ctgatatgct ttgcagtttg cttgattaac ttctagccct acagagtgca      7020
cagagagcaa aatcatggtg ttcagtgaat tctggggagt tattttaatg tgaaaattct      7080
ctagaagttt aattcctgca aagtgcagct gctgatcact acacaagata aaaatgtggg      7140
gggtgcataa acgtatattc ttacaataat agatacatgt gaacttatat acagaaaaga      7200
aaatgagaaa aatgtgtgtg tgtatactca cacgtggt cagtaaaaac ttttgagggg         7260
tttaatacag aaaatccaat cctgaggccc cagcactcag tacgcatata aagggctggg      7320
ctctgaagga cttctgactt tcacagatta tataaatctc aggaaagcaa ctagattcat      7380
gctggctcca aaagctgtgc tttatataag cacactggct atacaatagt tgtacagttc      7440
agctctttat aatagaaaca gacagaacaa gtataaatct tctattggtc tatgtcatga      7500
acaagaattc attcagtggc tctgttttat agtaaacatt gctattttat catgtctgca      7560
tttctcttct gtctgaatgt caccactaaa atttaactcc acagaaagtt tatactacag      7620
tacacatgca tatctttgag caaagcaaac catacctgaa agtgcaatag agcagaatat      7680
gaattacatg cgtgtctttc tcctagacta catgacccca tataaattac attacttatc      7740
tattctgcca tcaccaaaac aaaggtaaaa atacttttga agatctactc atagcaagta      7800
gtgtgcaaca aacagatatt tctctacatt tatttttagg gaataaaaat aagaaataaa      7860
atagtcagca agcctctgct ttctcatata tctgtccaaa cctaaagttt actgaaattt      7920
gctctttgaa tttccagttt tgcaagccta tcagattgtg ttttaatcag aggtactgaa      7980
aagtatcaat gaattctagc tttcactgaa caaaaatatg tagaggcaac tggcttctgg      8040
gacagtttgc tacccaaaag acaactgaat gcaaatacat aaatagattt atgaatatgg      8100
ttttgaacat gcacatgaga ggtggatata gcaacagaca cattaccaca gaattacttt      8160
aaaactactt gttaacattt aattgcctaa aaactgctcg taatttactg ttgtagccta      8220
ccatagagta ccctgcatgg tactatgtac agcattccat ccttacattt tcactgttct      8280
gctgtttgct ctagacaact cagagttcac catgggctcc atcggtgcag caagcatgga      8340
attttgtttt gatgtattca aggagctcaa agtccaccat gccaatgaga acatcttcta      8400
ctgccccatt gccatcatgt cagctctagc catggtatac ctgggtgcaa aagacagcac      8460
caggacacaa ataaataagg tgagcctaca gttaaagatt aaaacctttg ccctgctcaa      8520
tggagccaca gcacttaatt gtatgataat gtcccttgga aactgcatag ctcagaggct      8580
gaaaatctga aaccagagtt atctaaaagt gtggccacct ccaactccca gagtgttacc      8640
caaatgcact agctagaaat cttgaaactg gattgcataa cttcttttg tcataaccat       8700 tatttcagct actattattt tcaattacag gttgttcgct ttgataaact tccaggattc      8760
ggagacagta ttgaagctca ggtacagaaa taatttcacc tccttctcta tgtccctttc      8820
ctctggaagc aaaatacagc agatgaagca atctcttagc tgttccaagc cctctctgat      8880
gagcagctag tgctctgcat ccagcagttg ggagaacact gttcataaga acagagaaaa      8940
```

```
agaaggaagt aacaggggat tcagaacaaa cagaagataa aactcaggac aaaaataccg  9000
tgtgaatgag gaaacttgtg gatatttgta cgcttaagca agacagctag atgattctgg  9060
ataaatgggt ctggttggaa aagaaggaaa gcctggctga tctgctggag ctagattatt  9120
gcagcaggta ggcaggagtt ccctagagaa aagtatgagg gaattacaga agaaaaacag  9180
cacaaaattg taaatattgg aaaaggacca catcagtgta gttactagca gtaagacaga  9240
caggatgaaa aatagttttg taaacagaag tatctaacta ctttactctg ttcatacact  9300
acgtaaaact tactaagtaa taaaactaga ataacaacat cttttctttct ctttgtattc  9360
agtgtggcac atctgtaaac gttcactctt cacttagaga catcctcaac caaatcacca  9420
aaccaaatga tgtttattcg ttcagccttg ccagtagact ttatgctgaa gagagatacc  9480
caatcctgcc agtaagttgc tctaaaatct gatctgagtg tattccatgc caaagctcta  9540
ccattctgta atgcaaaaac agtcagagtt ccacatgttt cactaagaaa atttcttttt  9600
ctcttgtttt tacaaatgaa agagaggaca aataacattt ctctatcacc gacctgaaac  9660
tctacagtct tcagagaatg aatggcttgc taaaagaatg tcaaatctta ctatacagct  9720
atttcatatt acactactaa atacactata aggcatagca tgtagtaata cagtgtaaaa  9780
tagcttttta cactactata ttattaatat ctgttaattc cagtcttgca tttcacattt  9840
gcaaaacgtt ttgaaattcg tatctgaaag ctgaatactc ttgctttaca ggaatacttg  9900
cagtgtgtga aggaactgta tagaggaggc ttggaaccta tcaactttca aacagctgca  9960
gatcaagcca gagagctcat caattcctgg gtagaaagtc agacaaatgg taaggtagaa  10020
catgctttgt acatagtgag agttggttca ccctaatact gagaacttgg atatagctca  10080
gccagcgtgc tttgcgttca agcttaccag agctgttgta tgcctgttaa gcagggcata  10140
cagtcatgag gctcttgaaa aatcttaaca gacaaagggc aatggaaaat cggagttaag  10200
ggatggtagg gataaaatgc atagaaaagag gtaccacaat tttgattttt gccctaatgc  10260
ctctctgcgt ggttcctcaa tttttctact tcattcctca tctcctcaga gcattccttt  10320
ccctcatgct tgaaacacag atgaaagact gtgaattcta actgagatga aacatccac  10380
aaccacacaa cctctggtgt ggagtcacat tctgtgaagg caaaaactag gccacgtaat  10440
ctatgcgtgc aagctacgcg taagctatgt gtgtgacagg acaatgtgag gaacatacta  10500
tgtgcacaag gactgcagaa taaacaggag caaagttttt gaagaaaaca gagtaaaatc  10560
ctgttttcct cttttgttac attctttaca tatatctcaa atttcctctt tggttagaag  10620
caagtaatat ttatgtttct tggtactgtt tgggttgaag accattctgg gataagagaa  10680
attccagtgg ttcttcccct aatcataaaa tgtcaggttt agttttttg taacacagaa  10740
atctcttcat cttttatctt ttgttgtgat tcttgataga gagagaaaca agacttactg  10800
acaatagcag caagaaaatc aatcttggaa gaacaagatt gcaattgcaa aaacaaacca  10860
atgtccttgc ccctacatcc tcttccccat aaattctaca ttctctatct accttgtgct  10920
tgccaacatg atatacgtaa actctctttt cctattcatt cttaaaggaa ttatcagaaa  10980
tgtccttcag ccaagctccg tggattctca aactgcaatg gttctggtta atgccattgt  11040
cttcaaagga ctgtgggaga aagcatttaa ggatgaagac acacaagcaa tgcctttcag  11100
agtgactgag gtatatgggc ataccttaga gatgtaatct agaatttatg aagagagtag  11160
acatgttgtt tatgaacac tgcattagcg tatctgctca tttgtctgca tctctttcag  11220
acactgtgtt aaaagcaggg aattttcctt atgtctctct cgtcacaata ttcctgacat  11280
```

-continued

```
tgcaaagctc ctgagaaata acttcagatt ccacttttcc taggaaggct tctggatgag   11340
aactaatcat cttaactgta actagacatt tctgcatcca agaataatct ttgttaaaac   11400
tatattctct ctctcttttt tttttttttt tggttctcca gcaagaaagc aaacctgtgc   11460
agatgatgta ccagattggt ttatttagag tggcatcaat ggcttctgag aaaatgaaga   11520
tcctggagct tccatttgcc agtgggacaa tgagcatgtt ggtgctgttg cctgatgaag   11580
tctcaggcct tgagcaggta tggccctaga agttggcttc agaatattaa aaacacatgg   11640
aaatttagct gttgtaaagc tcttttcaac acagttatcc taaaacattt aaccagcaca   11700
aatttcatca tgattcaata tgtgattgtt gcatagaagt gtagatttgt cccactgggt   11760
cctgcaatag cccatgctga gcatggcttg ctgaaagaac tgctttagag ggtgaaaagt   11820
ttgacacagc agacaagatg attctcacct aagcagctgt tactgtagtg gcttgaactc   11880
taaaggtctt gtatctccat tcctgtgcac tgaggagctt cttggaaagt tcatataagg   11940
tttactagtt ctaactatta tctcatttgg tggcactcaa tgtgctttgt tcacgtcttc   12000
ataaattaat ctatctaaaa attggatgtg gttaaagcaa tttcagaaat aacatgtaca   12060
taatgtacaa ttattgatat gaacagaaca caggcatagc atattgtaat taggaggact   12120
gtagttattt tgaataggaa acacaatgta ataaatgaga attcattgaa atgttagtat   12180
gctaactcaa tctaaattat aaagataaag aggcatttaa tcacagctag atttccatca   12240
cttgtgacag acaggcatat gaatgattat gtacagctct aggaaaaaaa gtatgtagga   12300
aaactagtac attttgatta gaaagtctga aaatgaggtg ccttgatcaa agagaatacg   12360
tgtgtttgag aaaaaaaaag tttggataga ggtggtaaga gagaatatat tgaaatggtg   12420
tttctacaaa ctgccatggc cagatttgtg taagagacat tcagtaagta ggcaaggaaa   12480
gaaatattac taggtacaaa gcaacatcag taataccaaa agaaaccaat tattccagat   12540
gccaatctcg taatagggtt aagagatttc caccccctcta gtggtcacca gtgcaaccag   12600
taactttgct aatttacatt ttctttttttt aaatggcaga tatagctttg aactgagtga   12660
tcatgaactg gtactgtgta atagatgaag acatacttga cgactaaact tctgattttt   12720
aaaaactcaa attctcttga aagatcagtt cccagtctag taacagctga tagtttaagt   12780
atcagtaatt ggctaccatt aacaactggc tcctgagagg tcttaaatgt agagacagct   12840
ttaaactcaa aagcacagag tgattttttag aatagatttc ccaagcaaag aaaataaaca   12900
gggaggagct ttaagggagt agccatctca ttattattat tatttaaaga aatggcagca   12960
agcctacaaa agaaaaataa gacagagcag agaagaaaga gtcatggtat gcttttctat   13020
cttagcaaaa ttaatctcta catgcctagg aaaaagccat gacaagagca atcagttcaa   13080
aaggtgtatg caaaaaacca cataatagta actagtactg cattgccagg aaggaagtta   13140
tgtcgccatt ccatggatct cattctcatt tccttgcagc ttgagagtat aatcaacttt   13200
gaaaaactga ctgaatggac cagttctaat gttatggaag agaggaagat caaagtgtac   13260
ttacctcgca tgaagatgga ggaaaaatac aacctcacat ctgtcttaat ggctatgggc   13320
attactgacg tgtttagctc ttcagccaat ctgtctggca tctcctcagc agagagcctg   13380
aagatatctc aagctgtcca tgcagcacat gcagaaatca tgaagcagg cagagaggtg   13440 gtagggtcag cagaggctgg agtggatgct gcaagcgtct ctgaagaatt tagggctgac   13500
catccattcc tcttctgtat caagcacatc gcaaccaacg ccgttctctt ctttggcaga   13560
tgtgtttccc cttaaaaaga agaaagctga aaaactctgt cccttccaac aagacccaga   13620
gcactgtagt atcaggggta aaatgaaaag tatgttatct gctgcatcca gacttcataa   13680
```

```
aagctggagc ttaatctaga aaaaaaatca gaaagaaatt acactgtgag aacaggtgca   13740
attcactttt cctttacaca gagtaatact ggtaactcat ggatgaaggc ttaagggaat   13800
gaaattggac tcacagtact gagtcatcac actgaaaaat gcaacctgat acatcagcag   13860
aaggtttatg ggggaaaaat gcagccttcc aattaagcca gatatctgta tgaccaagct   13920
gctccagaat tagtcactca aaatctctca gattaaatta tcaactgtca ccaaccattc   13980
ctatgctgac aaggcaattg cttgttctct gtgttcctga tactacaagg ctcttcctga   14040
cttcctaaag atgcattata aaaatcttat aattcacatt tctccctaaa ctttgactca   14100
atcatggtat gttggcaaat atggtatatt actattcaaa ttgttttcct tgtacccata   14160
tgtaatgggt cttgtgaatg tgctcttttg ttcctttaat cataataaaa acatgtttaa   14220
gcaaacactt ttcacttgta gtatttgaag tacagcaagg ttgtgtagca gggaaagaat   14280
gacatgcaga ggaataagta tggacacaca ggctagcagc gactgtagaa caagtactag   14340
tgggtgagaa gttgaacaag agtcccctac aagcaactta atctaataag ctagtggtct   14400
acatcagcta aaagagcata gtgagggatg aaattggttc tcctttctaa gcatcacctg   14460
ggacaactca tctggagcag tgtgtccaat ctgccgctgc cctgatctcg gctggggtga   14520
tgggacagac cttggctgcc actgagacat ctgagacact gagatctgtc tcaactcaga   14580
tttacccaag aacagctcat tgccaacaga acaaaatctc aaacttatgg ctagtgatga   14640
cagcagtcag ttgtcccatc tgtgacccac caaggctggc atgctggaat gagcaggctt   14700
tggtggcatg tagttactgg acagcaccac tgacatgggc aggggaaaaa ctgagcatgg   14760
tgtaaatcac tgcctcaaag ccacttctct gtgcctgcac catgcttgaa agctcttcta   14820
caggagctgg gtttgttcaa gaaagcttct gtttctccca tctgcttctt gtaccttcac   14880
agggacagag ttagaagggt acagccatgg ctggaagggg ctgactttca aatgtgccta   14940
attttccttt ggttgctgct gcagctgcag aagaagggt tcagaagcca agagctttga    15000
gataaggatg cctaacctat gttgaagaca tttgtgctga cacctcaggc cccaggatag   15060
gacaactgct ggattgtggc taacccacta gctacagaac ctaatttata ttaccagatt   15120
aggaagagca aaagaacatg tatttataac aggaggtctt ctgtgcttct ctactaaaag   15180
gtgctgtgaa ggagcccaca gtgcagcagt gtatgaggcc tgaaagaggc cgcagcacac   15240 gaaagagccct ggtaggagca gcacacagag gggcaggagg gctgggggaa ctgccaccca   15300
tggggacctg tgtgaagcag tgcactcctg aggggtggac tgcgtgggaa aggaaaagaa   15360
agcaaacaga cctgtgatga actgtcacac agactgcaga gtgacagagg agggcacgag   15420
gcagtgcgcc cactgcaggg agtggcgctc cttcctcaca gcagcgctaa cagcttggca   15480
ccaatattca gtagtctgtg gtgatacttt ttccagtttc accacacagc atttcgcttg   15540
ttctacttgt tttagctttc cccctccaca agataacaca tactttgcca gtcagtccct   15600
aagaccttaa cttaacagtt agcaaacagg atcttgcaaa agaaggaaga taacatgaca   15660
ccaccttcac tggtgtataa atagttcaaa tactttcctt cactttcccg taaattagtt   15720
gattgcaggt caggagataa caggggaact tactgcaaga gagaaaatga tgtttaatat   15780
tgtcttggac tttctggtgg tctgggcatg aaaatggggt actcaaaatc ctcgggacgt   15840 ttattttttca cctgatttat tcccaaactg cactatttct aggccattgg agttcttatc   15900
aattaaatta tactttggct ctctgctatc tcactccctt tcatcttcag catcactttc   15960
agcacaatta caggagaaga cttagactca gagctttagg actcatcata agaggctttc   16020
```
attgctctgt caccacaccc catatagatc t                                16051

<210> SEQ ID NO 23
<211> LENGTH: 7334
<212> TYPE: DNA
<213> ORGANISM: Artificial Sequence
<220> FEATURE:
<223> OTHER INFORMATION: Description of Artificial Sequence: Synthetic
      pBS-OM-4.4 vector polynucleotide

<400> SEQUENCE: 23

```
atcaagctta tcgataccgt cgacctcgag gggggggcccg gtacccagct tttgttccct    60
ttagtgaggg ttaatttcga gcttggcgta atcatggtca tagctgtttc ctgtgtgaaa   120
ttgttatccg ctcacaattc cacacaacat acgagccgga agcataaagt gtaaagcctg   180
gggtgcctaa tgagtgagct aactcacatt aattgcgttg cgctcactgc ccgctttcca   240
gtcgggaaac ctgtcgtgcc agctgcatta atgaatcggc caacgcgcgg ggagaggcgg   300
tttgcgtatt gggcgctctt ccgcttcctc gctcactgac tcgctgcgct cggtcgttcg   360
gctgcggcga gcggtatcag ctcactcaaa ggcggtaata cggttatcca cagaatcagg   420
ggataacgca ggaaagaaca tgtgagcaaa aggccagcaa aaggccagga accgtaaaaa   480
ggccgcgttg ctggcgtttt tccataggct ccgcccccct gacgagcatc acaaaaatcg   540
acgctcaagt cagaggtggc gaaacccgac aggactataa agataccagg cgtttccccc   600
tggaagctcc ctcgtgcgct ctcctgttcc gaccctgccg cttaccggat acctgtccgc   660
ctttctccct tcgggaagcg tggcgctttc tcatagctca cgctgtaggt atctcagttc   720
ggtgtaggtc gttcgctcca agctgggctg tgtgcacgaa ccccccgttc agcccgaccg   780
ctgcgcctta tccggtaact atcgtcttga gtccaacccg gtaagacacg acttatcgcc   840
actggcagca gccactggta acaggattag cagagcgagg tatgtaggcg gtgctacaga   900
gttcttgaag tggtggccta actacggcta cactagaagg acagtatttg gtatctgcgc   960
tctgctgaag ccagttacct tcggaaaaag agttggtagc tcttgatccg gcaaacaaac  1020
caccgctggt agcggtggtt tttttgtttg caagcagcag attacgcgca gaaaaaaagg  1080
atctcaagaa gatcctttga tcttttctac ggggtctgac gctcagtgga acgaaaactc  1140
acgttaaggg attttggtca tgagattatc aaaaaggatc ttcacctaga tccttttaaa  1200
ttaaaaatga agttttaaat caatctaaag tatatatgag taaacttggt ctgacagtta  1260
ccaatgctta atcagtgagg cacctatctc agcgatctgt ctatttcgtt catccatagt  1320
tgcctgactc cccgtcgtgt agataactac gatacgggag ggcttaccat ctggccccag  1380
tgctgcaatg ataccgcgag acccacgctc accggctcca gatttatcag caataaacca  1440
gccagccgga agggccgagc gcagaagtgg tcctgcaact ttatccgcct ccatccagtc  1500
tattaattgt tgccgggaag ctagagtaag tagttcgcca gttaatagtt tgcgcaacgt  1560
tgttgccatt gctacaggca tcgtggtgtc acgctcgtcg tttggtatgg cttcattcag  1620
ctccggttcc caacgatcaa ggcgagttac atgatccccc atgttgtgca aaaaagcggt  1680
tagctccttc ggtcctccga tcgttgtcag aagtaagttg gccgcagtgt tatcactcat  1740
ggttatggca gcactgcata attctcttac tgtcatgcca tccgtaagat gcttttctgt  1800
gactggtgag tactcaacca agtcattctg agaatagtgt atgcggcgac cgagttgctc  1860
ttgcccggcg tcaatacggg ataataccgc gccacatagc agaactttaa aagtgctcat  1920
cattggaaaa cgttcttcgg ggcgaaaact ctcaaggatc ttaccgctgt tgagatccag  1980
```

```
ttcgatgtaa cccactcgtg cacccaactg atcttcagca tcttttactt tcaccagcgt    2040
ttctgggtga gcaaaaacag gaaggcaaaa tgccgcaaaa aagggaataa gggcgacacg    2100
gaaatgttga atactcatac tcttccttt tcaatattat tgaagcattt atcagggtta    2160
ttgtctcatg agcggataca tatttgaatg tatttagaaa aataaacaaa tagggggttcc    2220
gcgcacattt ccccgaaaag tgccacctaa attgtaagcg ttaatatttt gttaaaattc    2280
gcgttaaatt tttgttaaat cagctcattt tttaaccaat aggccgaaat cggcaaaatc    2340
ccttataaat caaagaata gaccgagata gggttgagtg ttgttccagt ttggaacaag     2400
agtccactat taagaacgt ggactccaac gtcaaagggc gaaaaaccgt ctatcagggc     2460
gatggcccac tacgtgaacc atcaccctaa tcaagttttt tggggtcgag gtgccgtaaa    2520
gcactaaatc ggaaccctaa agggagcccc cgatttagag cttgacgggg aaagccggcg    2580
aacgtggcga aaaggaagg gaagaaagcg aaaggagcgg gcgctagggc gctggcaagt     2640
gtagcggtca cgctgcgcgt aaccaccaca cccgccgcgc ttaatgcgcc gctacagggc    2700
gcgtcccatt cgccattcag gctgcgcaac tgttgggaag ggcgatcggt gcgggcctct    2760
tcgctattac gccagctggc gaaaggggga tgtgctgcaa ggcgattaag ttgggtaacg    2820
ccagggtttt cccagtcacg acgttgtaaa acgacggcca gtgaattgta atacgactca    2880
ctatagggcg aattggagct ccaccgcggt ggcggccgct ctagaactag tggatccttc    2940
ttaaaagca gaccatcatt cactgcaaac ccagagcttc atgcctctcc ttccacaacc    3000
gaaaacagcc ggcttcattt gtctttttta aatgctgttt tccaggtgaa ttttggccag    3060
cgtgttggct gagatccagg agcacgtgtc agctttctgc tctcattgct cctgttctgc    3120
attgcctctt tctggggttt ccaagagggg gggagacttt gcgcggggat gagataatgc    3180
cccttttctt agggtggctg ctgggcagca gagtggctct gggtcactgt ggcaccaatg    3240
ggaggcacca gtgggggtgt gttttgtgca gggggggaagc attcacagaa tggggctgat    3300
cctgaagctt gcagtccaag gctttgtctg tgtacccagt gaaatccttc ctctgttaca    3360
taaagcccag ataggactca gaaatgtagt cattccagcc cccctcttcc tcagatctgg    3420
agcagcactt gtttgcagcc agtcctcccc aaaatgcaca gacctcgccg agtggaggga    3480
gatgtaaaca gcgaaggtta attacctcct tgtcaaaaac actttgtggt ccatagatgt    3540
ttctgtcaat cttacaaaac agaaccgaga ggcagcgagc actgaagagc gtgttcccat    3600
gctgagttaa tgagacttgg cagctcgctg tgcagagatg atccctgtgc ttcatgggag    3660
gctgtaacct gtctccccat cgccttcaca ccgcagtgct gtcctggaca cctcacctc     3720
cataagctgt aggatgcagc tgcccaggga tcaagagact tttcctaagg ctcttaggac    3780
tcatcttgtc cgctcagtag cgtgcagcaa ttactcatcc caactatact gaatgggttt    3840
ctgccagctc tgcttgtttg tcaataagca tttcttcatt ttgcctctaa gtttctctca    3900
gcagcaccgc tctgggtgac ctgagtggcc acctggaacc cgaggggcac agccaccacc    3960
tccctgttgc tgctgctcca gggactcatg tgctgctgga tggggggaag catgaagttc    4020
ctcacccaga cacctgggtt gcaatggctg cagcgtgctc ttcttggtat gcagattgtt    4080
tccagccatt acttgtagaa atgtgctgtg gaagcccttt gtatctcttt ctgtggccct    4140
tcagcaaaag ctgtgggaaa gctctgaggc tgctttcttg ggtcgtggag gaattgtatg    4200
ttccttcttt aacaaaaatt atccttagga gagagcactg tgcaagcatt gtgcacataa    4260
aacaattcag gttgaaaggg ctctctggag gtttccagcc tgactactgc tcgaagcaag    4320
gccaggttca agatggctc aggatgctgt gtgccttcct gattatctgt gccaccaatg     4380
```

```
gaggagattc acagccactc tgcttcccgt gccactcatg gagaggaata ttcccttata      4440
ttcagataga atgttatcct ttagctcagc cttccctata accccatgag ggagctgcag      4500
atccccatac tctcccttc  tctggggtga aggccgtgtc ccccagcccc ccttcccacc      4560
ctgtgcccta agcagcccgc tggcctctgc tggatgtgtg cctatatgtc aatgcctgtc      4620
cttgcagtcc agcctgggac atttaattca tcaccagggt aatgtggaac tgtgtcatct      4680 tccctgcag  ggtacaaagt tctgcacggg gtcctttcgg ttcaggaaaa ccttcactgg      4740
tgctacctga atcaagctct atttaataag ttcataagca catggatgtg ttttcctaga      4800
gatacgtttt aatggtatca gtgattttta tttgctttgt tgcttacttc aaacagtgcc      4860
tttgggcagg aggtgaggga cgggtctgcc gttggctctg cagtgatttc tccaggcgtg      4920
tggctcaggt cagatagtgg tcactctgtg gccagaagaa ggacaaagat ggaaattgca      4980
gattgagtca cgttaagcag gcatcttgga gtgatttgag gcagtttcat gaaagagcta      5040
cgaccactta ttgttgtttt cccttttac aacagaagtt ttcatcaaaa taacgtggca       5100
aagcccagga atgtttggga aaagtgtagt taaatgtttt gtaattcatt tgtcggagtg      5160
ctaccagcta agaaaaaagt cctacctttg gtatggtagt cctgcagaga atacaacatc      5220
aatattagtt tggaaaaaaa caccaccacc accagaaact gtaatggaaa atgtaaacca      5280
agaaattcct tgggtaagag agaaaggatg tcgtatactg gccaagtcct gcccagctgt      5340
cagcctgctg accctctgca gttcaggacc atgaaacgtg gcactgtaag acgtgtcccc      5400
tgcctttgct tgcccacaga tctctgccct tgtgctgact cctgcacaca agagcatttc      5460
cctgtagcca aacagcgatt agccataagc tgcacctgac tttgaggatt aagagtttgc      5520
aattaagtgg attgcagcag gagatcagtg gcagggttgc agatgaaatc cttttctagg      5580
ggtagctaag ggctgagcaa cctgtcctac agcacaagcc aaaccagcca agggttttcc      5640
tgtgctgttc acagaggcag ggccagctgg agctggagga ggttgtgctg ggacccttct      5700
ccctgtgctg agaatggagt gatttctggg tgctgttcct gtggcttgca ctgagcagct      5760
caagggagat cggtgctcct catgcagtgc caaaactcgt gtttgatgca gaaagatgga      5820
tgtgcacctc cctcctgcta atgcagccgt gagcttatga aggcaatgag ccctcagtgc      5880
agcaggagct gtagtgcact cctgtaggtg ctagggaaaa tctctggttc ccagggatgc      5940
attcataagg gcaatatatc ttgaggctgc gccaaatctt tctgaaatat tcatgcgtgt      6000
tcccttaatt tatagaaaca aacacagcag aataattatt ccaatgcctc ccctcgaagg      6060
aaacccatat ttccatgtag aaatgtaacc tatatacaca cagccatgct gcatccttca      6120
gaacgtgcca gtgctcatct cccatggcaa aatactacag gtattctcac tatgttggac      6180
ctgtgaaagg aaccatggta agaaacttcg gttaaaggta tggctgcaaa actactcata      6240
ccaaaacagc agagctccag acctcctctt aggaaagagc cacttggaga gggatggtgt      6300
gaaggctgga ggtgagagac agagcctgtc ccagttttcc tgtctctatt ttctgaaacg      6360
tttgcaggag gaaaggacaa ctgtactttc aggcatagct ggtgccctca cgtaaataag      6420
ttccccgaac ttctgtgtca tttgttctta agatgctttg gcagaacact ttgagtcaat      6480
tcgcttaact gtgactaggt ctgtaaataa gtgctccctg ctgataaggt tcaagtgaca      6540
tttttagtgg tatttgacag catttacctt gctttcaagt cttctaccaa gctcttctat      6600
acttaagcag tgaaaccgcc aagaaaccct tcctttatc aagctagtgc taaataccat       6660
taacttcata ggttagatac ggtgctgcca gcttcacctg gcagtggttg gtcagttctg      6720
```

| | |
|---|---|
| ctggtgacaa agcctccctg gcctgtgctt ttacctagag gtgaatatcc aagaatgcag | 6780 |
| aactgcatgg aaagcagagc tgcaggcacg atggtgctga gccttagctg cttcctgctg | 6840 |
| ggagatgtgg atgcagagac gaatgaagga cctgtcccct actcccctca gcattctgtg | 6900 |
| ctatttaggt ttctaccaga gtccttaaga ggttttttt tttttttggtc caaaagtctg | 6960 |
| tttgtttggt tttgaccact gagagcatgt gacacttgtc tcaagctatt aaccaagtgt | 7020 |
| ccagccaaaa tcaattgcct gggagacgca gaccattacc tggaggtcag gacctcaata | 7080 |
| aatattacca gcctcattgt gccgctgaca gattcagctg gctgctccgt gttccagtcc | 7140 |
| aacagttcgg acgccacgtt tgtatatatt tgcaggcagc ctcgggggga ccatctcagg | 7200 |
| agcagagcac cggcagccgc ctgcagagcc gggcagtacc tcaccatggc catggcaggt | 7260 |
| gtcttcgtgc tgttctcttt cgtgctttgt ggcttcctcc caggtgagta actcccagag | 7320 |
| tgctgcagaa gctt | 7334 |

<210> SEQ ID NO 24
<211> LENGTH: 4327
<212> TYPE: DNA
<213> ORGANISM: Artificial Sequence
<220> FEATURE:
<223> OTHER INFORMATION: Description of Artificial Sequence: Synthetic
    pAVIJCR-A137.91.1.2 vector polynucleotide

<400> SEQUENCE: 24

| | |
|---|---|
| gccaatgtgg tacttcccac attgtataag aaatttggca agtttagagc aatgtttgaa | 60 |
| gtgttgggaa atttctgtat actcaagagg gcgttttttga caactgtaga acagaggaat | 120 |
| caaaaggggg tgggaggaag ttaaaagaag aggcaggtgc aagagagctt gcagtcccgc | 180 |
| tgtgtgtacg acactggcac catggctttg acctttgcct tactggtggc tctcctggtg | 240 |
| ctgagctgca agagcagctg ctctgtgggc tgcgatctgc ctcagaccca cagcctgggc | 300 |
| agcaggagga ccctgatgct gctggctcag atgaggagaa tcagcctgtt tagctgcctg | 360 |
| aaggataggc acgattttgg ctttcctcaa gaggagtttg gcaaccagtt tcagaaggct | 420 |
| gagaccatcc ctgtgctgca cgagatgatc cagcagatct ttaacctgtt tagcaccaag | 480 |
| gatagcagcg ctgcttggga tgagaccctg ctggataagt tttacaccga gctgtaccag | 540 |
| cagctgaacg atctggaggc ttgcgtgatc cagggcgtgg gcgtgaccga ccccctctg | 600 |
| atgaaggagg atagcatcct ggctgtgagg aagtactttc agaggatcac cctgtacctg | 660 |
| aaggagaaga agtacagccc ctgcgcttgg gaagtcgtga gggctgagat catgaggagc | 720 |
| tttagcctga gcaccaacct gcaagagagc ttgaggtcta aggagtaaaa agtctagagt | 780 |
| cggggcggcc ggccgcttcg agcagacatg ataagataca ttgatgagtt tggacaaacc | 840 |
| acaactagaa tgcagtgaaa aaaatgcttt atttgtgaaa tttgtgatgc tattgcttta | 900 |
| tttgtaacca ttataagctg caataaacaa gttaacaaca caattgcat tcatttatg | 960 |
| tttcaggttc agggggaggt gtgggaggtt ttttaaagca agtaaaacct ctacaaatgt | 1020 |
| ggtaaaatcg ataaggatcc gtcgaccgat gcccttgaga gccttcaacc cagtcagctc | 1080 |
| cttccggtgg cgcgggggca tgactatcgt cgccgcactt atgactgtct tctttatcat | 1140 |
| gcaactcgta ggacaggtgc cggcagcgct cttccgcttc ctcgctcact gactcgctgc | 1200 |
| gctcggtcgt tcggctgcgg cgagcggtat cagctcactc aaaggcggta atacggttat | 1260 |
| ccacagaatc aggggataac gcaggaaaga acatgtgagc aaaaggccag caaaaggcca | 1320 |
| ggaaccgtaa aaaggccgcg ttgctggcgt ttttccatag gctccgcccc cctgacgagc | 1380 |

-continued

```
atcacaaaaa tcgacgctca agtcagaggt ggcgaaaccc gacaggacta taaagatacc    1440
aggcgttttcc ccctggaagc tccctcgtgc gctctcctgt tccgaccctg ccgcttaccg    1500
gatacctgtc cgcctttctc ccttcgggaa gcgtggcgct ttctcaatgc tcacgctgta    1560
ggtatctcag ttcggtgtag gtcgttcgct ccaagctggg ctgtgtgcac gaaccccccg    1620
ttcagcccga ccgctgcgcc ttatccggta actatcgtct tgagtccaac ccggtaagac    1680
acgacttatc gccactggca gcagccactg gtaacaggat tagcagagcg aggtatgtag    1740
gcggtgctac agagttcttg aagtggtggc ctaactacgg ctacactaga aggacagtat    1800
ttggtatctg cgctctgctg aagccagtta ccttcggaaa aagagttggt agctcttgat    1860
ccggcaaaca aaccaccgct ggtagcggtg gttttttttgt ttgcaagcag cagattacgc    1920
gcagaaaaaa aggatctcaa gaagatcctt tgatcttttc tacggggtct gacgctcagt    1980
ggaacgaaaa ctcacgttaa gggattttgg tcatgagatt atcaaaaagg atcttcacct    2040
agatcctttt aaattaaaaa tgaagtttta aatcaatcta agtatatat gagtaaactt    2100
ggtctgacag ttaccaatgc ttaatcagtg aggcacctat ctcagcgatc tgtctatttc    2160
gttcatccat agttgcctga ctccccgtcg tgtagataac tacgatacgg agggcttac    2220
catctggccc cagtgctgca atgataccgc gagacccacg ctcaccggct ccagatttat    2280
cagcaataaa ccagccagcc ggaagggccg agcgcagaag tggtcctgca actttatccg    2340
cctccatcca gtctattaat tgttgccggg aagctagagt aagtagttcg ccagttaata    2400
gtttgcgcaa cgttgttgcc attgctacag gcatcgtggt gtcacgctcg tcgtttggta    2460
tggcttcatt cagctccggt tcccaacgat caaggcgagt tacatgatcc cccatgttgt    2520
gcaaaaaagc ggttagctcc ttcggtcctc cgatcgttgt cagaagtaag ttggccgcag    2580
tgttatcact catggttatg gcagcactgc ataattctct tactgtcatg ccatccgtaa    2640
gatgcttttc tgtgactggt gagtactcaa ccaagtcatt ctgagaatag tgtatgcggc    2700
gaccgagttg ctcttgcccg gcgtcaatac gggataatac cgcgccacat agcagaactt    2760
taaaagtgct catcattgga aaacgttctt cggggcgaaa actctcaagg atcttaccgc    2820
tgttgagatc cagttcgatg taacccactc gtgcacccaa ctgatcttca gcatctttta    2880
ctttcaccag cgtttctggg tgagcaaaaa caggaaggca aaatgccgca aaaaagggaa    2940
taagggcgac acggaaatgt tgaatactca tactcttcct ttttcaatat tattgaagca    3000
tttatcaggg ttattgtctc atgagcggat acatatttga atgtatttag aaaaataaac    3060
aaatagggt tccgcgcaca tttccccgaa aagtgccacc tgacgcgccc tgtagcggcg    3120
cattaagcgc ggcgggtgtg gtggttacgc gcagcgtgac cgctacactt gccagcgccc    3180
tagcgcccgc tcctttcgct ttcttccctt cctttctcgc cacgttcgcc ggctttcccc    3240
gtcaagctct aaatcggggg ctccctttag ggttccgatt tagtgcttta cggcacctcg    3300
accccaaaaa acttgattag ggtgatggtt cacgtagtgg gccatcgccc tgatagacgg    3360
tttttcgccc tttgacgttg gagtccacgt tctttaatag tggactcttg ttccaaactg    3420
gaacaacact caaccctatc tcggtctatt cttttgattt ataagggatt tgccgatttc    3480
cggcctattg gttaaaaaat gagctgattt aacaaaaatt taacgcgaat tttaacaaaa    3540
tattaacgtt tacaatttcc cattcgccat tcaggctgcg caactgttgg gaagggcgat    3600
cggtgcgggc ctcttcgcta ttacgccagc ccaagctacc atgataagta agtaatatta    3660
aggtacggga ggtacttgga gcggccgcaa taaaatatct ttattttcat tacatctgtg    3720
tgttggtttt ttgtgtgaat cgatagtact aacatacgct ctccatcaaa acaaaacgaa    3780
```

```
acaaaacaaa ctagcaaaat aggctgtccc cagtgcaagt gcaggtgcca gaacatttct    3840
ctatcgatag gtaccgagct cttacgcgtg ctagccccga tgtacgggcc agatatacgc    3900
gttgacattg attattgact agttattaat agtaatcaat tacggggtca ttagttcata    3960
gcccatatat ggagttccgc gttacataac ttacggtaaa tggcccgcct ggctgaccgc    4020
ccaacgaccc ccgcccattg acgtcaataa tgacgtatgt tcccatagta acgccaatag    4080
ggactttcca ttgacgtcaa tgggtggact atttacggta aactgcccac ttggcagtac    4140
atcaagtgta tcatatgcca gtacgcccc ctattgacgt caatgacggt aaatggcccg    4200
cctggcatta tgcccagtac atgaccttat gggactttcc tacttggcag tacatctacg    4260
tattagtcat cgctattacc atgcatggct ttgacctttg ccttactggt ggctctcctg    4320
gtgctta                                                              4327

<210> SEQ ID NO 25
<211> LENGTH: 244
<212> TYPE: DNA
<213> ORGANISM: Artificial Sequence
<220> FEATURE:
<223> OTHER INFORMATION: Description of Artificial Sequence: Synthetic
      RRE (rev responsive element) polynucleotide

<400> SEQUENCE: 25
aattgaggag ctttgttcct tgggttcttg ggagcagcag gaagcactat gggcgcagcg     60
tcaatgacgc tgacggtaca ggccagacaa ttattgtctg gtatagtgca gcagcagaac    120
aatttgctga gggctattga ggcgcaacag catctgttgc aactcacagt ctggggcatc    180
aagcagctcc aggcaagaat cctggctgtg gaaagatacc taaaggatca acagctcctg    240
gtac                                                                 244

<210> SEQ ID NO 26
<211> LENGTH: 158
<212> TYPE: DNA
<213> ORGANISM: Artificial Sequence
<220> FEATURE:
<223> OTHER INFORMATION: Description of Artificial Sequence: Synthetic
      ALV CTE (constitutive transport element) polynucleotide

<400> SEQUENCE: 26
aatgtgggga gggcaaggct tgcgaatcgg gttgtaacgg gcaaggcttg actgagggga     60
caatagcatg tttaggcgaa aagcggggct tcggttgtac gcggttagga gtcccctcag    120
gatatagtag tttcgctttt gcatagggag ggggaaat                            158

<210> SEQ ID NO 27
<211> LENGTH: 55
<212> TYPE: DNA
<213> ORGANISM: Artificial Sequence
<220> FEATURE:
<223> OTHER INFORMATION: Description of Artificial Sequence: Synthetic
      p10.0-OM-IFN-1 primer

<400> SEQUENCE: 27
ggcgtcgacg gatccgttaa ccctagaact agtggatctc tgcccttgtg ctgac          55

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Synthetic
``` p10.0-OM-IFN-2 oligonucleotide

<400> SEQUENCE: 28
ggcctcgagc ctagactttt tactccttag a                                       31

<210> SEQ ID NO 29
<211> LENGTH: 346
<212> TYPE: DNA
<213> ORGANISM: Artificial Sequence
<220> FEATURE:
<223> OTHER INFORMATION: Description of Artificial Sequence: Synthetic
      ALV vector 5' LTR polynucleotide

<400> SEQUENCE: 29
aatgtagtct tatgcaatac tcttgtagtc ttgcaacatg cttatgtaac gatgagttag        60
caacatgcct tataaggaga gaaaaagcac cgtgcatgcc gattggtggg agtaaggtgg       120
tatgatcgtg gtatgatcgt gccttgttag gaaggcaaca gacgggtcta acacggattg       180
gacgaaccac tgaattccgc attgcagaga tattgtattt aagtgcctag ctcgatacaa       240
taaacgccat ttgaccattc accacattgg tgtgcacctg ggttgatggc cggaccgttg       300
attccctgrc gactacgagc acatgcatga agcagaaggc ttcatt                     346

METHOD OF USING A TRANSGENIC CHICKEN TO PRODUCE EXOGENOUS PROTEINS IN ITS EGGS

RELATED APPLICATION INFORMATION

This application is a continuation application of U.S. patent application Ser. No. 14/194,010, filed Feb. 28, 2014, which is a continuation-in-part of U.S. patent application Ser. No. 13/747,201, filed Jan. 22, 2013, which is continuation of U.S. patent application Ser. No. 13/179,281, filed Jul. 8, 2011, now U.S. Pat. No. 8,383,399, issued Feb. 26, 2013, which is Divisional of U.S. patent application Ser. No. 11/978,360, filed Oct. 29, 2007, which claims the benefit of US provisional application Nos. 60/930,491, filed May 16, 2007 and 60/994,203, filed Sep. 18, 2007 and is a continuation-in-part of U.S. patent application Ser. No. 11/699,257, filed Jan. 26, 2007 and is also a continuation-in-part of U.S. patent application No. 11/799,253, filed May 1, 2007 which is a continuation-in-part of U.S. patent application Ser. No. 11/210,165, filed Aug. 23, 2005 which claims the benefit of US provisional application No. 60/640,203, filed Dec. 29, 2004. The disclosures of each of these U.S. patent applications and provisional applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Jul. 18, 2016, is named 535_00020134_SL.txt and is 110,538bytes in size.

FIELD OF THE INVENTION

The present invention relates generally to the use of promoters which function in cells of a transgenic avian (e.g., oviduct cells) such as a transgenic chicken and vectors which contain such promoters. More specifically, the invention relates to recombinant nucleic acids and expression vectors, transfected cells and transgenic animals, for example, transgenic avians such as transgenic chickens, that contain vectors with gene expression controlling regions operably linked to coding sequences.

BACKGROUND

The field of transgenics was initially developed to understand the action of a single gene in the context of the whole animal and the phenomena of gene activation, expression and interaction. Transgenics technology has also been used to produce models for various diseases in humans and other animals and is among the most powerful tools available for the study of genetics, and the understanding of genetic mechanisms and function. From an economic perspective, the use of transgenic technology to convert animals into "protein factories" for the production of specific proteins or other substances of pharmaceutical interest (Gordon et al., 1987, Biotechnology 5: 1183-1187; Wilmut et al., 1990, Theriogenology 33: 113-123) offers significant advantages over more conventional methods of protein production by gene expression.

One system useful for expressing foreign proteins is the avian reproductive system. The production of an avian egg begins with formation of a large yolk in the ovary of the hen. The unfertilized oocyte or ovum is positioned on top of the yolk sac.

After ovulation, the ovum passes into the infundibulum of the oviduct where it is fertilized, if sperm are present, and then moves into the magnum of the oviduct, which is lined with tubular gland cells. These cells secrete the egg-white proteins, including ovalbumin, lysozyme, ovomucoid, conalbumin and ovomucin, into the lumen of the magnum where they are deposited onto the avian embryo and yolk. In the past exogenous protein production has been performed in the avian reproductive system specifically targeting the avian oviduct.

Advantages of targeting the avian oviduct for exogenous protein expression can include proper folding and post-translation modification of the target protein, the ease of product recovery, and a shorter developmental period of birds such as chickens compared to other animal species.

Directing expression of a heterologous gene product in the oviduct of a transgenic avian can be significantly advantageous over ubiquitous expression in the bird. That is, the consequences of ubiquitous expression of a bioactive gene product in a host animal may be undesirable. For example, in certain instances the ubiquitous presence of the recombinant protein may be harmful to the development of the avian which can kill the bird. Additionally, the bird's health may be negatively effected leading to reduced levels of protein production.

By weight, approximately 60% of an avian egg is composed of albumen which is composed of four major protein components; ovalbumin, ovomucoid, lysozyme and ovotransferrin with ovalbumin and ovomucoid being present in the greatest quantities.

The ovalbumin promoter, ovomucoid promoter and lysozyme promoter have been successfully employed for the production of heterologous (exogenous) protein in the oviduct of transgenic avians in the past. See, for example, U.S. Pat. No. 6,875,588, issued Apr. 5, 2005; U.S. Pat. No. 7,176,300, issued Feb. 13, 2007; U.S. Pat. No. 7,199,279, issued Apr. 3, 2007; and US patent publication No. 2006/0130170, published Jun. 15, 2006(the disclosures of each of these three issued patents and one published patent application are incorporated in their entirety herein by reference) which discloses the production of exogenous protein in the avian oviduct facilitated by various avian promoters which are primarily or exclusively expressed in the oviduct. Though expression levels in avians using the promoters and fragments of the promoters disclosed in these issued patents and published application have been at useful levels, the yeilds have typically been well below 0.1 mg/ml of egg white.

What is needed is a system that will provide for high level expression of an exogenous coding sequence in the cells of a transgenic avian, in particular, in the oviduct cells (e.g., tubular gland cells) of a transgenic avian.

SUMMARY OF THE INVENTION

The present invention meets this need and more. After years of exogenous protein production in transgenic avian oviduct tissue with modest yield the inventors of the present invention have discovered that such production levels can be boosted by about 10 fold to about 100 fold and more by employing new compositions and methods as disclosed herein.

In one aspect, the invention is directed to transgenic avians (e.g., chicken, turkey, quail) containing in their genome an exogenous nucleotide sequence which includes a promoter component and a SIN vector. Typically, the promoter component is linked to a coding sequence exogenous to the avian, i.e., the coding sequence is not normally or naturally present in the avian. Typically, the exogenous nucleotide sequence is integrated into the genome of the avian. In one particularly useful embodiment, the promoter component functions or expresses primarily in the oviduct (e.g., tubular gland cells) of an avian. For example, the promoter component may be an oviduct specific promoter. For example, the promoter component may be one of an avian ovomucoid promoter component, an avian ovalbumin promoter component, an avian lysozyme promoter component and an avian ovoinhibitor promoter component (i.e., conalbumin promoter component).

SIN vectors have been shown by the inventors to be particularly useful for increasing the quantity of exogenous protein produced in the avian oviduct. This effect can be further enhanced when the SIN vector is also an SC negative vector (i.e., a vector not containing a selectable marker cassette with a functional promoter).

The invention also includes methods of making the transgenic avians of the invention and methods of producing an exogenous protein using transgenic avians of the invention. In one embodiment, the transgenic avian has a nucleotide sequence in its genome comprising a vector which is at least one of a SIN vector and an SC negative vector. Typically, the nucleotide sequence includes a promoter component linked to an exogenous coding sequence.

In one useful embodiment, the exogenous coding sequence is expressed in avian oviduct cells and is secreted from the oviduct cells. For example, the exogenous coding sequence may be expressed in tubular gland cells. In one embodiment, the exogenous protein is deposited in a hard shell egg laid by the transgenic avian. In one embodiment, the exogenous protein is a human protein. In one embodiment, the exogenous protein is a therapeutic protein, e.g., a cytokine.

In one embodiment, the transgenic avian contains an exogenous nucleotide sequence in its genome which has a SC negative vector and a promoter component linked to an exogenous coding sequence encoding an exogenous protein. In one embodiment, the SC negative vector is also a SIN vector.

In one aspect, avian leukosis virus vector (ALV), a murine leukemia virus (MLV) retroviral vector, moloney murine leukemia Virus (MMLV) and a lentiviral vector can be used in accordance with the invention.

The invention includes chimeric transgenic avians and fully transgenic germline avians which can be obtained from germline chimeras as is understood by a practitioner of skill in the art of poultry breeding.

The invention also includes gene expression controlling regions or promoters having a nucleotide, sequence (i.e., DNA sequence) similar or identical to the following sequences numbered 1 to 8. In a particularly useful embodiment of the invention, the fragments are listed top to bottom in the 5' to 3' linear order in which they are present on a single DNA molecule. For example, the 3' end of the 3.5 kb OV fragment of sequence 1 would be covalently linked to the 5' end of the 5' UTR-5' portion and the 3' end of the 5' UTR-5' portion would be covalently linked to the 5' end of 5' UTR-3' portion. However, the invention is not limited to any particular order of the fragments and intervening nucleotide sequences may be present between the fragments.

1. 3.5 kb OV fragment (includes DHS I, II & III)
   5' UTR-5' portion (from Exon L)
   5' UTR-3' portion (from Exon 1);
2. 3.5 kb OV fragment (includes DHS I, II & III)
   5' UTR-5' portion (from Exon L)
   Intron A
   5' UTR-3' portion (from Exon 1)
   3' UTR;
3. 3.5 kb OV fragment (includes DHS I, II & III)
   5' UTR-5' portion (from Exon L)
   Intron A
   5' UTR-3' portion (from Exon 1);
4. 3.5 kb OV fragment (includes DHS I, II & III)
   5' UTR-5' portion (from Exon L)
   5' UTR-3' portion (from Exon 1)
   3' UTR;
5. 3.5 kb OV fragment (includes DHS I, II & III)
   5' UTR-5' portion (from Exon L)
   Intron A
   5' UTR-3' portion (from Exon 1)
   3' UTR/DHS A (bp 13576 to 15163 of SEQ ID NO: 22)
6. 3.5 kb OV fragment (includes DHS I, II & III)
   5' UTR-5' portion (from Exon L)
   5' UTR-3' portion (from Exon 1)
   3' UTR/DHS A (bp 13576 to 15163 of SEQ ID NO: 22)
7. 3.5 kb OV fragment (includes DHS I, II & III)
   5' UTR-5' portion (from Exon L)
   Intron A
   5' UTR-3' portion (from Exon 1)
   partial 3' UTR
   RRE (Rev response element) FIG. 9a
8. ALV CTE (FIG. 9b) inserted 5' of 3.5 kb OV fragment
   3.5 kb OV fragment (includes DHS I, II & III)
   5' UTR-5' portion (from Exon L)
   Intron A
   5' UTR-3' portion (from Exon 1)
   partial 3' UTR;

Coordinates of some of the elements for specific ovalbumin constructs disclosed herein (e.g., constructs 1 to 8 described above) are shown in the 16051 by ovalbumin DNA segment of SEQ ID NO: 22 as follows:

3.5 kb OV fragment (includes DHS I, II & III): Start: 3199 End: 6659 of FIG. 8 (SEQ ID NO: 22);

1.4 kb OV fragment (includes DHS I & II): Start: 5209 End: 6659 of FIG. 8 (SEQ ID NO: 22);

3.8 kb OV fragment: Start: 2863 End: 6659 of FIG. 8 (SEQ ID NO: 22);

5.2 kb OV fragment: Start: 1463 End: 6659 of FIG. 8 (SEQ ID NO: 22);

5' UTR-5' portion (from Exon L): Start: 6659 End: 6705 of FIG. 8 (SEQ ID NO: 22);

5' UTR-3' portion (from Exon 1): Start: 8295 End: 8311 of FIG. 8 (SEQ ID NO: 22);

3' UTR: Start: 13576 End: 14209 of FIG. 8 (SEQ ID NO: 22);

partial 3' UTR: Start 13576 End: 13996 of FIG. 8 (SEQ ID NO: 22);

Intron A: Start: 6706 End: 8294 of FIG. 8 (SEQ ID NO: 22);

Intron E: Start: 10010 End: 10968 of FIG. 8 (SEQ ID NO: 22);

Exon L: Start: 6659 End: 6705 of FIG. 8 (SEQ ID NO: 22);

Exon 1: Start: 8295 End: 8478 of FIG. 8 (SEQ ID NO: 22);

Exon 2: Start: 8731 End: 8781 of FIG. 8 (SEQ ID NO: 22);

Exon 3: Start: 9363 End: 9491 of FIG. 8 (SEQ ID NO: 22);

Exon 4: Start: 9892 End: 10009 of FIG. 8 (SEQ ID NO: 22);

Exon 5: Start: 10968 End: 11110 of FIG. 8 (SEQ ID NO: 22);

Exon 6: Start: 11442 End: 11597 of FIG. 8 (SEQ ID NO: 22);

Exon 7: Start: 13180 End: 13575 of FIG. 8 (SEQ ID NO: 22);

+1 SITE: Start: 6659 End: 6659 of FIG. 8 (SEQ ID NO: 22);

ATG: Start: 8312 End: 8312 of FIG. 8 (SEQ ID NO: 22);

Poly A: Start: 14204 End: 14209 of FIG. 8 (SEQ ID NO: 22);

TATA: Start: 6627 End: 6632 of FIG. 8 (SEQ ID NO: 22);

DHS A: Start: 13858 End: 15163 of FIG. 8 (SEQ ID NO: 22);

DHS IV: Start: 459 End: 859 of FIG. 8 (SEQ ID NO: 22);

DHS III: Start: 3253 End: 3559 of FIG. 8 (SEQ ID NO: 22);

DHS II: Start: 5629 End: 6009 of FIG. 8 (SEQ ID NO: 22); and

DHS I: Start: 6359 End: 6659 of FIG. 8 (SEQ ID NO: 22).

Promoter constructs are also contemplated that have a nucleotide sequence 80% identical and 85% identical and 90% identical and 91% identical and 92% identical and 93% identical and 94% identical and 95% identical and 96% identical and 97% identical and 98% identical and 99% identical to each of the promoter constructs disclosed herein, such as those described above (i.e., 1 to 8 above).

The invention also contemplates promoter constructs which correspond to promoter constructs 1 through 8 above in which the 3.5 kb OV fragment is replaced with the 3.8 kb OV fragment. The invention also contemplates promoter constructs which correspond to promoter constructs 1 through 8 in which the 3.5 kb OV fragment is replaced with the 5.2 kb OV fragment.

Promoter constructs are also contemplated for each of the above specified recombinant promoters (i.e., 1 to 8) in which DHS III is omitted from the construct.

Promoter constructs are contemplated corresponding to each of constructs 2, 3, 5, 7 and 8 above in which Intron A is replaced with Intron E which may lead to increased levels of exogenous protein production. Intron A and E have DNA sequences that induce alignment of histones in surrounding DNA regions. Such alignment can provide for transcriptional regulation of the OV gene. Without wishing to be bound to any particular theory or mechanism of operation, substitution of Intron E with Intron A may provide a preferential spacing of histones that result from use of Intron E (i.e., the periodicity for Intron A is 202 bp+/−5 bp, for Intron E is 196 bp+/−5 bp). For example, it is believed that the packaging of DNA by histones leads to topological alteration of DNA the manipulation of which can lead to preferential alignment of binding sites for proteins responsible for the transcription regulation (e.g., transcription factors) leading to an enhanced level of transcription.

Also included in the invention are vector constructs, and other constructs and nucleotide sequences disclosed herein, having a nucleotide sequence 80% identical and 85% identical and 90% identical and 91% identical and 92% identical and 93% identical and 94% identical and 95% identical and 96% identical and 97% identical and 98% identical and 99% identical to each vector construct and other constructs and nucleotide sequences disclosed herein.

Any useful combination of features described herein is included within the scope of the present invention provided that the features included in any such combination are not mutually inconsistent as will be apparent from the context, this specification, and the knowledge of one of ordinary skill in the art Additional objects and aspects of the present invention will become more apparent upon review of the detailed description set forth below when taken in conjunction with the accompanying figures, which are briefly described as follows.

BRIEF DESCRIPTION OF THE FIGURES

FIG. 8*a-e* (SEQ ID NO: 22) shows a segment of a chicken ovalbumin gene.

FIG. 9*a* (SEQ ID NO: 25) shows the RRE (rev responsive element) sequence of a lenti virus. FIG. 9*b* (SEQ ID NO: 26) shows the ALV CTE (constitutive transport element) sequence.

FIG. 10*a* shows a diagram of the segment deleted from an exemplary retroviral LTR (ALV) to make a SIN vector. FIG. 10*b* (SEQ ID NO: 29) shows the sequence of the LTR shown in 10*a*. The underlined sequence is the deleted sequence.

DETAILED DESCRIPTION

Definitions

Figure 1:
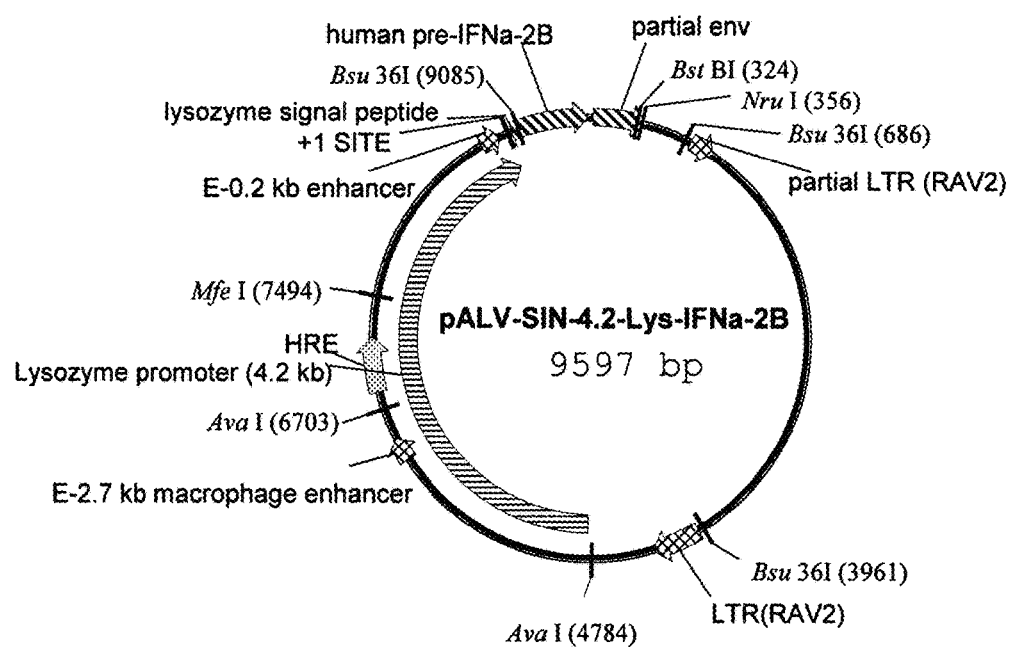
FIG. 1 shows a circular map of the pALV-SIN-4.2-Lys-IFNa-2B vector. The sequence of pALV-SIN-4.2-Lys-IFNa-2B is shown in SEQ ID NO: 1.

The term "animal" is used herein to include all vertebrate animals, including avians and may include humans. It also includes an individual animal in all stages of development, including embryonic and fetal stages.

The term "antibody" as used herein refers to polyclonal and monoclonal antibodies and functional fragments thereof. An antibody includes modified or derivatised antibody variants that retain the ability to specifically bind an epitope. Antibodies are capable of selectively binding to a target antigen or epitope. Antibodies may include, but are not limited to polyclonal antibodies, monoclonal antibodies (mAbs), humanized and other chimeric antibodies, single chain antibodies (scFvs), Fab fragments, F(ab')$_2$ fragments and disulfide-linked Fvs (sdFv) fragments.

The term "avian" as used herein refers to any species, subspecies or strain of organism of the taxonomic class ava, such as, but not limited to, such organisms as chicken, turkey, duck, goose, quail, pheasants, parrots, finches, hawks, crows and ratites including ostrich, emu and cassowary. The term includes the various known strains of Gallus gallus, or chickens, (for example, White Leghorn, Brown Leghorn, Barred-Rock, Sussex, N.H., R.I., Ausstralorp, Minorca, Amrox, California Gray, Italian Partridge-colored), as well as strains of turkeys, pheasants, quails, duck, ostriches and other poultry commonly bred in commercial quantities.

The phrase "based on" or "derived from" as in a retroviral vector being based on or derived from a particular retrovirus or based on a nucleotide sequence of a particular retrovirus mean that the genome of the retroviral vector contains a substantial portion of the nucleotide sequence of the genome of the particular retrovirus. The substantial portion may be a particular gene or nucleotide sequence such as the nucleotide sequence encoding the gag, pol and/or env proteins or other structural or functional nucleotide sequence of the virus genome such as sequences encoding the LTRs or may be substantially the complete retrovirus genome, for example, most (e.g., more than 60% or more than 70% or more than 80% or more than 90%) or all of the retrovirus genome, as will be apparent from the context in the specification as the knowledge of one skilled in the art. Examples of retroviral vectors that are based on or derived from a retrovirus are the NL retroviral vectors (e.g., NLB) which are based on the ALV retrovirus as disclosed in Cosset et al, Journal of Virology (1991) vol 65, p 3388-3394.

The term "coding sequence" and "coding region" as used herein refer to nucleotide sequences and nucleic acid sequences, including both RNA and DNA, that encode genetic information for the synthesis of an RNA, a protein, or any portion of an RNA or protein. Nucleotide sequences that are not naturally part of a particular organism's genome are referred to as "foreign nucleotide sequences," "heterologous nucleotide sequences" or "exogenous nucleotide sequences". "Heterologous proteins" are proteins encoded by foreign, heterologous or exogenous nucleotide sequences and therefore are often not naturally expressed in the cell. A nucleotide sequence that has been isolated and then reintroduced into the same type (e.g., same species) of organism is not considered to be a naturally occurring part of a particular organism's genome and is therefore considered exogenous or heterologous.

The term "construct" as used herein refers to a linear or circular nucleotide sequence such as DNA that has been assembled from more than one segments of nucleotide sequence which have been isolated from a natural source or have been chemically synthesized, or combinations thereof.

The term "complementary" as used herein refers to two nucleic acid molecules that can form specific interactions with one another. In the specific interactions, an adenine base within one strand of a nucleic acid can form two hydrogen bonds with thymine within a second nucleic acid strand when the two nucleic acid strands are in opposing polarities. Also in the specific interactions, a guanine base within one strand of a nucleic acid can form three hydrogen bonds with cytosine within a second nucleic acid strand when the two nucleic acid strands are in opposing polarities. Complementary nucleic acids as referred to herein, may further comprise modified bases wherein a modified adenine may form hydrogen bonds with a thymine or modified thymine, and a modified cytosine may form hydrogen bonds with a guanine or a modified guanine.

The term "cytokine" as used herein refers to any secreted amino acid sequence that affects the functions of cells and is a molecule that modulates interactions between cells in the immune, inflammatory or hematopoietic responses. A cytokine includes, but is not limited to, monokines and lymphokines regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-alpha) and Tumor Necrosis Factor beta (TNF-beta).

The term "expressed" or "expression" as used herein refers to the transcription from a gene to give an RNA nucleic acid molecule at least complementary in part to a region of one of the two nucleic acid strands of the gene. The term "expressed" or "expression" as used herein can also refer to the translation of RNA to produce a protein or peptide.

The term "expression vector" as used herein refers to a nucleic acid vector that comprises a gene expression controlling region, such as a promoter or promoter component, operably linked to a nucleotide sequence coding at least one polypeptide.

The term "fragment" as used herein can refer to, for example, an at least about 10, 20, 50, 75, 100, 150, 200, 250, 300, 500, 1000, 2000, 5000, 6,000, 8,000, 10,000, 20,000, 30,000, 40,000, 50,000 or 60,000 nucleotide long portion of a nucleic acid that has been constructed artificially (e.g., by chemical synthesis) or by cleaving a natural product into multiple pieces, using restriction endonucleases or mechanical shearing, or enzymatically, for example, by PCR or any other polymerizing technique known in the art, or expressed in a host cell by recombinant nucleic acid technology known to one of skill in the art. The term "fragment" as used herein may also refer to, for example, an at least about 5, 10, 20, 30, 40, 50, 75, 100, 150, 200, 250, 300, 400, 500, 1000, 2000, 5000, 6,000, 8,000 or 10,000 amino acid portion of an amino acid sequence, which portion is cleaved from a naturally occurring amino acid sequence by proteolytic cleavage by at least one protease, or is a portion of the naturally occurring amino acid sequence synthesized by chemical methods or using recombinant DNA technology (e.g., expressed from a portion of the nucleotide sequence encoding the naturally occurring amino acid sequence) known to one of skill in the art. "Fragment" may also refer to a portion, for example, of about 5%, about 10%, about 20%, about 30%, about 40%, about 50%, about 60%, about 70%, about 80% about 90% about 95% or about 99% of a particular nucleotide sequence or amino acid sequence.

"Functional portion" or "functional fragment" are used interchangeably and as used herein means a portion or fragment of a whole capable of performing, in whole or in part, a function of the whole. For example, a biologically functional portion of a molecule means a portion of the molecule that performs a biological function of the whole or intact molecule. For example, a functional portion of a gene expression controlling region is a fragment or portion of the specified gene expression controlling region that, in whole or in part, regulates or controls gene expression (e.g., facilitates either in whole or in part) in a biological system (e.g., a promoter). Functional portions may be of any useful size. For example, a functional fragment may range in size from about 20 bases in length to a length equal to the entire length of the specified sequence minus one nucleotide. In another example, a functional fragment may range in size from about 50 bases in length to a length equal to the entire length of the specified sequence minus one nucleotide. In another example, a functional fragment may range in size from about 50 bases in length to about 20 kb in length. In another example, a functional fragment may range in size from about 500 bases in length to about 20 kb in length. In another example, a functional fragment may range in size from about 1 kb in length to about 20 kb in length. In another example, a functional fragment may range in size from about 0.1 kb in length to about 10 kb in length. In another example, a functional fragment may range in size from about 20 bases kb in length to about 10 kb in length.

The term "gene expression controlling region" as used herein refers to nucleotide sequences that are associated with a coding sequence and which regulate, in whole or in part, expression of the coding sequence, for example, regulate, in whole or in part, the transcription of the coding sequence. Gene expression controlling regions may be isolated from a naturally occurring source or may be chemically synthesized and can be incorporated into a nucleic acid vector to enable regulated transcription in appropriate cells. The "gene expression controlling regions" may precede, but is not limited to preceding, the region of a nucleic acid sequence that is in the region 5' of the end of a coding sequence that may be transcribed into mRNA.

The terms "heterologous", "exogenous" and "foreign" are used interchangeably herein and in general refer to a biomolecule such as a nucleic acid or a protein that is not normally found in a certain organism or in a certain cell, tissue or other component contained in or produced by an organism. For example, a protein that is heterologous or exogenous to an egg is a protein that is not normally found in the egg. As used herein, the terms "heterologous", "exogenous" and "foreign" with reference to nucleic acids, such as DNA and RNA, are used interchangeably and refer to nucleic acid that does not occur naturally as part of a chromosome, a genome or cell in which it is present or which is found in a location(s) and/or in amounts that differ from the location(s) and/or amounts in which it occurs in nature. It can be nucleic acid that is not endogenous to the genome, chromosome or cell and has been exogenously introduced into the genome, chromosome or cell. Examples of heterologous DNA include, but are not limited to, a DNA comprising a gene expression control region and DNA that encodes a product or products, for example, RNA or protein product. Examples of heterologous DNA include, but are not limited to, gene expression controlling regions or promoters disclosed herein once isolated from the avian and as used thereafter, e.g., after re-introduction into an avian genome.

The term "isolated nucleic acid" as used herein covers, for example, (a) a DNA which has the sequence of part of a naturally occurring genomic molecule but is not flanked by at least one of the sequences that flank that part of the molecule in the genome of the species in which it naturally occurs; (b) a nucleic acid which has been incorporated into a vector or into the genomic DNA of a prokaryote or eukaryote in a manner such that the resulting vector or genomic DNA is not identical to naturally occurring DNA from which the nucleic acid was obtained; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring. Isolated nucleic acid molecules of the present invention can include, for example, natural allelic variants as well as nucleic acid molecules modified by nucleotide deletions, insertions, inversions, or substitutions.

The term "nucleic acid" as used herein refers to any linear or sequential array of nucleotides and nucleosides, for example cDNA, genomic DNA, mRNA, tRNA, oligonucleotides, oligonucleosides and derivatives thereof. For ease of discussion, non-naturally occurring nucleic acids may be referred to herein as constructs. Nucleic acids can include bacterial plasmid vectors including expression, cloning, cosmid and transformation vectors such as, animal viral vectors such as, but not limited to, modified adenovirus, influenza virus, polio virus, pox virus, retroviruses such as avian leukosis virus (ALV) retroviral vector, a murine leukemia virus (MLV) retroviral vector, and a lentivirus vector, and the like and fragments thereof. In addition, the nucleic acid can be an LTR of an avian leukosis virus (ALV) retroviral vector, a murine leukemia virus (MLV) retroviral vector, or a lentivirus vector and fragments thereof. Nuclic acids can also include NL vectors such as NLB, NLD and NLA and fragments thereof and synthetic oligonucleotides such as chemically synthesized DNA or RNA. Nucleic acids can include modified or derivatised nucleotides and nucleosides such as, but not limited to, halogenated nucleotides such as, but not only, 5-bromouracil, and derivatised nucleotides such as biotin-labeled nucleotides.

The term "vector" and "nucleic acid vector" as used herein refers to a natural or synthetic single or double stranded plasmid or viral nucleic acid molecule that can be transfected or transformed into cells and replicate independently of, or within, the host cell genome. A circular double stranded vector can be linearized by treatment with an appropriate restriction enzyme based on the nucleotide sequence of the vector. A nucleic acid can be inserted into a vector by cutting the vector with restriction enzymes and ligating the desired pieces together.

The term "operably linked" refers to an arrangement of elements wherein the components so described are configured so as to perform their usual function. Gene expression controlling regions or promoters (e.g., promoter components) operably linked to a coding sequence are capable of effecting the expression of the coding sequence. The controlling sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "oviduct specific promoter" as used herein refers to promoters and promoter components which are functional, i.e., provide for transcription of a coding sequence, to a large extent, for example, primarily (i.e., more than 50% of the transcription product produced in the animal by a particular promoter type being produced in oviduct cells) or exclusively in oviduct cells of a bird. Examples of oviduct specific promoters include, ovalbumin promoter, ovomucoid promoter, ovoinhibitor promoter, lysozyme promoter and ovotransferrin promoter and functional portions of these promoters, e.g., promoter components.

The terms "percent sequence identity" "percent identity" as used in, for example, "% identical" and "percent sequence homology" "percent homology", as used in, for example, "% homology" and "percent sequence similarity" each refer to the degree of sequence matching between two nucleic acid sequences or two amino acid sequences as determined using the algorithm of Karlin & Attschul (1990) Proc. Natl. Acad. Sci. 87: 2264-2268, modified as in Karlin & Attschul (1993) Proc. Natl. Acad. Sci. 90: 5873-5877. Such an algorithm is incorporated into the NBLAST and XBLAST programs of Attschul et al. (1990) T. Mol. Biol. Q15: 403-410. BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference amino acid sequence. To obtain gapped alignments for comparison purposes, Gapped BLAST is utilized as described in Attschul et al. (1997) Nucl. Acids Res. 25: 3389-3402. When utilizing BLAST and Gapped BLAST programs, the default parameters of the respective programs (e.g. XBLAST and NBLAST) are used. Other algorithms, programs and default settings may also be suitable such as, but not only, the GCG-Sequence Analysis Package of the U.K. Human Genome Mapping Project Resource Centre that includes programs for nucleotide or amino acid sequence comparisons.

The terms "polynucleotide," "oligonucleotide", "nucleotide sequence" and "nucleic acid sequence" can be used interchangeably herein and include, but are not limited to, coding sequences, i.e., polynucleotide(s) or nucleic acid sequence(s) which are transcribed and translated into polypeptide in vitro or in vivo when placed under the control of appropriate regulatory or control sequences; controlling sequences, e.g., translational start and stop codons, promoter sequences, ribosome binding sites, polyadenylation signals, transcription factor binding sites, transcription termination sequences, upstream and downstream regulatory domains, enhancers, silencers, DNA sequences to which a transcription factor(s) binds and alters the activity of a gene's promoter either positively (induction) or negatively (repression) and the like. No limitation as to length or to synthetic origin are suggested by the terms described herein.

As used herein the terms "polypeptide" and "protein" refer to a polymer of amino acids of three or more amino acids in a serial array, linked through peptide bonds. The term "polypeptide" includes proteins, protein fragments, protein analogues, oligopeptides and the like. The term "polypeptides" includes polypeptides as defined above that are encoded by nucleic acids, produced through recombinant technology (e.g., isolated from a transgenic bird), or synthesized. The term "polypeptides" further contemplates polypeptides as defined above that include chemically modified amino acids or amino acids covalently or noncovalently linked to labeling ligands.

The term "promoter" as used herein refers to a DNA sequence useful to initiate transcription initiation by an RNA polymerase in an avian cell. A "promoter component" is a DNA sequence that can, by itself or, in combination with other DNA sequences effect or facilitate transcription. Specific promoter components such as ovalbumin promoter components, ovomucoid promoter components and lysozyme promoter components and other promoters and promoter components disclosed and claimed herein do not describe a specific promoter sequence. Rather, they encompass any sequence or sequence fragment of the respective promoter that is useful to effect or facilitate transcription of a coding sequence. For example, an ovomucoid promoter component includes, without limitation, the about 1.8 kb, the about 3.9 kb and the about 10 kb ovomucoid promoters disclosed in US publication No. 11/649,543, published May 17, 2007, which is incorporated in its entirety herein by reference. "Promoter components" can also encompass rearranged gene expression controlling regions which function to initiate RNA transcription and hybrid DNA molecules composed of naturally occurring DNA sequences and/or synthetic DNA sequences which function to initiate RNA transcription.

The terms "recombinant nucleic acid" and "recombinant DNA" as used herein refer to combinations of at least two nucleic acid sequences that are not naturally found in a eukaryotic or prokaryotic cell. The nucleic acid sequences may include, but are not limited to, nucleic acid vectors, gene expression regulatory elements, origins of replication, suitable gene sequences that when expressed confer antibiotic resistance, protein-encoding sequences and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

As used herein, the term "regulatory sequences" includes promoters, enhancers, and other elements that may control gene expression.

An "SC negative vector" is a vector that does not contain a selectable or screenable cassette marker having a functional promoter. The promoter may be deleted in whole or in part or may be inactivated by a nucleotide sequence insertion. Screenable cassettes include, without limitation, DNA sequences for antibiotic resistance markers such as neomycin resistance and DNA sequences for other selectable markers such as GFP or lacZ.

A "SIN vector" is a self-inactivating vector. In particular, a SIN vector is a retroviral vector having an altered genome such that upon integration into genomic DNA of the target cell (e.g., avian embryo cells) the 5' LTR of the integrated retroviral vector will not function as a promoter. For example, a portion or all of the nucleotide sequence of the retroviral vector that results in the U3 region of the 5' LTR of the retroviral vector once integrated may be deleted or altered in order to reduce or eliminate promoter activity of the 5' LTR. In certain examples, deletion of the CAAT box and/or the TAATA box from U3 of the 5' LTR can result in a SIN vector, as is understood in the art.

A "SIN/SC negative vector" is a vector, i.e., a retroviral vector, that is both a SIN vector and a SC negative vector.

The term "sense strand" as used herein refers to a single stranded DNA, molecule from a genomic DNA that may be transcribed into RNA and translated into the natural polypeptide product of the gene. The term "antisense strand" as used herein refers to the single strand DNA molecule of a genomic DNA that is complementary with the sense strand of the gene.

A "therapeutic protein" or "pharmaceutical protein" is a substance that, in whole or in part, makes up a drug. In particular, "therapeutic proteins" and "pharmaceutical proteins" include an amino acid sequence which in whole or in part makes up a drug.

The terms "transcription regulatory sequences" and "gene expression control regions" and "promoter components" as used herein refer to nucleotide sequences that are associated with a nucleic acid sequence and which regulate the transcriptional expression of a coding sequence. Exemplary transcription regulatory sequences include enhancer elements, hormone response elements, steroid response elements, negative regulatory elements, and the like. The "transcription regulatory sequences" may be isolated and incorporated into a vector nucleic acid to enable regulated transcription in appropriate cells of portions of the vector DNA. The "transcription regulatory sequence" may precede, but is not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron" regions, or may be in regions of nucleic acid sequence that are in the region of nucleic acid.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with high concentrations of salt such as, but not only a calcium or magnesium salt, an electric field, detergent, or liposome mediated transfection, to render the host cell competent for the uptake of the nucleic acid molecules.

As used herein, a "transgenic animal" is any non-human animal, such as an avian species, including the chicken, in which one or more of the cells of the avian may contain heterologous nucleic acid introduced by way of human intervention, such as by transgenic techniques known in the art (see, for example, US patent publication No. 2007/0243165, published Oct. 18, 2007, the disclosure of which is incorporated in its entirety herein by reference) including those disclosed herein. The nucleic acid is introduced into an animal, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animal, the transgene can cause cells to express a recombinant form of the target protein or polypeptide. The terms "chimeric animal" or "mosaic animal" are used herein to refer to animals in which a transgene is found, or in which the recombinant nucleotide sequence is expressed in some but not all cells of the animal. A germ-line chimeric animal contains a transgene in its germ cells and can give rise to a transgenic animal in which most or all cells of the offspring animal will contain the transgene.

As used herein, the term "transgene" means a nucleic acid sequence (encoding, for example, a human protein) that is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene according to the present invention can include a vector of the invention (e.g., SIN vector) which contains sequences useful for exogenous protein production in an avian (e.g., in an avian oviduct).

Techniques useful for isolating and characterizing the nucleic acids and proteins of the present invention are well known to those of skill in the art and standard molecular biology and biochemical manuals may be consulted to select suitable protocols for use without undue experimentation. See, for example, Sambrook et al, 1989, "Molecular Cloning: A Laboratory Manual", 2nd ed., Cold Spring Harbor, the content of which is herein incorporated by reference in its entirety.

Abbreviations:

Abbreviations used herein may include the following: aa, amino acid(s); bp, base pair(s); cDNA, DNA complementary to an RNA; nt, nucleotide(s); kb, 1000 base pairs; μg, microgram; ml, milliliter; ng, nanogram.

Description:

SIN vectors designed and used in accordance with the invention can reduce or eliminate promoter interference of promoters of interest which are employed in transgenic avians. In a particularly useful embodiment, the promoters (i.e., promoter components) of interest preferentially express their gene product in oviduct cells or oviduct tissue, e.g., oviduct specific promoters. Examples of such promoters (e.g., promoter components) include but are not limited to, functional portions of the ovalbumin, lysozyme, conalbumin (i.e., ovotransferrin), ovomucoid, ovomucin, and/or ovoinhibitor gene expression controlling regions or promoter regions. In one embodiment, the promoter of interest is a combination or a fusion of one or more promoters or a fusion of a fragment of one or more promoters such as ovalbumin, lysozyme, conalbumin (i.e., ovotransferrin), ovomucoid, ovomucin, and/or ovoinhibitor promoters with another promoter or promoter fragment such as a viral promoter (e.g., an LTR promoter).

SIN vectors have been shown to be particularly useful with oviduct specific promoters. Without wishing to limit the invention to any particular theory or mechanism of operation it is believed that oviduct specific promoters can be particularly susceptible to influences of a retroviral LTR promoter. As a result, SIN vectors are particularly useful when employed in combination with avian oviduct specific promoters.

In one particularly useful embodiment, a SIN vector is produced in which an interfering promoter (e.g., an LTR promoter) that can at least partially inhibit transcription of a coding sequence operably linked to an oviduct specific promoter of the invention is inactivated, for example, by a deletion, insertion or transposition of all or part of the interfering promoter sequence. For example, the vector pALV-SIN-4.2-Lys-IFNa-2B, shown in FIG. 1, the 3' RAV2 LTR has a deletion in the enhancer such that when the retroviral region integrates, the 5' LTR is inactivated, as is understood in the art. For a detailed diagrammatic of an LTR deletion, see FIG. 10.

In one useful embodiment of the invention, a SIN vector is employed that is also an SC negative vector to produce a SIN/SC negative vector. The combination of SC negative vector and SIN vector can result in a vector with a substantially reduced amount of promoter interference compared to a vector that is only a SIN vector or only a SC negative vector. For example, pALV-SIN-4.2-Lys-IFNa-2B as well as other SIN vectors disclosed in the Examples also lacks an antibiotic resistance marker making it both a SC negative vector and a SIN vector.

SIN vectors, SC negative vectors and SIN/SC negative vectors are contemplated for use in accordance with the invention in any useful avian such as chicken, quail and turkey to produce chimeras including germ-line chimeras and progeny birds produced using breeding techniques such as those known to practitioners of ordinary skill in the art. In addition, it is contemplated that an SC negative retroviral vector (which is a non-SIN vector) will also enhance or increase the quantity of exogenous protein produced in a transgenic avian relative to a transgenic avian produced with essentially the same retroviral vector that is not a SC negative vector.

Without wishing to limit the invention to any particular theory or mechanism of operation it is believed that the lack of a selectable marker cassette decreases the presence of promoter elements such as enhancers which would otherwise be in cis and in close proximity to the promoter employed for exogenous protein production in avian oviduct cells (e.g., oviduct specific promoters). This close proximity may allow for interference by the transcription regulating elements of the marker gene with the promoter of interest, i.e., the promoter employed for exogenous protein production. However, the invention contemplates that marker gene coding sequences, for example, and without limitation, neomycin resistance coding sequence and beta lactamase coding sequence, may be operably linked to a promoter (i.e., second promoter) which does not interfere with the promoter employed for exogenous protein production in avian oviduct cells (i.e., first promoter). For example, it is contemplated that if the marker promoter and the promoter of interest are the same or similar promoters, interference by the selectable cassette will be minimized or eliminated. For example, a second ovalbumin promoter operably linked to a marker gene coding sequence may not interfere with a first ovalbumin promoter employed for exogenous protein production in avian oviduct cells.

The invention contemplates the employment of any useful oviduct specific promoter, and oviduct specific promoter fragments, in vectors of the invention for exogenous protein expression in avians. For example, promoters and useful (e.g., functional) fragments of promoters (e.g., promoter components) disclosed in US patent publication No. 2005/0176047, filed Jan. 31, 2005, the disclosure of which is incorporated in its entirety herein by reference, and US patent publication No. 2007/0124829, filed Jan. 26, 2007, the disclosure of which is incorporated in its entirety herein by reference, and US patent publication No. 2006/0130170, filed Dec. 11, 2003, the disclosure of which is incorporated in its entirety herein by reference, are contemplated for use in conjunction with SIN vectors and SC negative vectors and SIN/SC negative vectors in accordance with the invention.

The invention also contemplates other promoters and transcriptionally functional portions thereof (e.g., promoter components) for use as promoters of interest in accordance with the invention such as a cytomegalovirus (CMV) promoter, a rous-sarcoma virus (RSV) promoter, a (β-actin promoter (e.g., a chicken (β-actin promoter) a murine leukemia virus (MLV) promoter, a mouse mammary tumor virus (MMTV) promoter.

The invention also includes various ovalbumin promoter components which are contemplated for use in producing exogenous proteins in transgenic avians. Each of the promoters disclosed herein are contemplated for use in vectors in accordance with the invention.

Examples of vectors of the invention which contain recombinant ovalbumin DNA are shown below. The fragments are listed top to bottom in the 5' to 3' linear order in which they are present on a single DNA molecule. For example, the 3' end of the 3.5 kb OV fragment of sequence 1 would be covalently linked to the 5' end of the 5' UTR-5' portion and the 3' end of the 5' UTR-5' portion would be covalently linked to the 5' end of 5' UTR-3' portion.

1. pSIN-OV-3.5-CSI
    3.5 kb OV fragment (includes DHS I, II & III)
    5' UTR-5' portion (from Exon L)
    5' UTR-3' portion (from Exon 1)
2. pSIN-OV-3.5-Int-CSI-inv
    3.5 kb OV fragment (includes DHS I, II & III)
    5' UTR-5' portion (from Exon L)
    Intron A
    5' UTR-3' portion (from Exon 1)
    3' UTR
3. pSIN-OV-3.5-Int-CSI
    3.5 kb OV fragment (includes DHS I, II & III)
    5' UTR-5' portion (from Exon L)
    Intron A
    5' UTR-3' portion (from Exon 1)
4. pSIN-OV-3.5-CSI-UTR-inv
    3.5 kb OV fragment (includes DHS I, II & III)
    5' UTR-5' portion (from Exon L)
    5' UTR-3' portion (from Exon 1)
    3' UTR
5. pSIN-OV-3.5-Int-CSI-LUTR-inv
    3.5 kb OV fragment (includes DHS I, II & III)
    5' UTR-5' portion (from Exon L)
    Intron A
    5' UTR-3' portion (from Exon 1)
    3' UTR/DHS A (bp 13576 to 15163 of FIG. 8);
6. pS1N-OV-3.5-CSI-LUTR-inv
    3.5 kb OV fragment (includes DHS I, II & III)
    5' UTR-5' portion (from Exon L)
    5' UTR-3' portion (from Exon 1)
    3' UTR/DHS A (bp 13576 to 15163 of FIG. 8);
7. pSIN-OV-3.5-Int-CSI-RRE
    3.5 kb OV fragment (includes DHS I, II & III)
    5' UTR-5' portion (from Exon L)
    Intron A
    5' UTR-3' portion (from Exon 1)
    partial 3' UTR
    RRE (Rev response element) FIG. 9a Construct 7 includes RRE to allow transport of the unspliced RNA genome to the cytoplasm and thus may enhance packaging of intact retroviral RNA. RRE is only active in presence of the Rev protein. Rev activity is provided in the form of DNA encoding the Rev, RNA encoding the Rev, and/or the Rev protein, which is well known in the art and commercially available (e.g., Invitrogen, Inc.), during the transient transfection of retroviral components. Thus the intron will be present in the transgene contained in the genome of the transgenic bird produced by the virus particles (the rev protein is not present in the cells of the transgenic bird). As a result the RNA should be spliced in the oviduct cells of a laying hen resulting in an enhanced level of protein expression compared to a same transgenic bird having the same transgene without the intron.

8. pS1N-CTE-OV-3.5-Int-CSI
    ALV CTE (FIG. 9b) inserted 5' of 3.5 kb OV fragment
    3.5 kb OV fragment (includes DHS I, II & III)
    5' UTR-5' portion (from Exon L)
    Intron A
    5' UTR-3' portion (from Exon 1)
    partial 3' UTR Coordinates for some of the elements for the above eight vectors are described elsewhere in the application. For example, coordinates of sequences from the ovalbumin nucleotide sequence are described in the Summary section above. CSI means a coding sequence of interest, i.e., nucleotide sequence encoding the protein desired to be expressed in a transgenic avian oviduct.

SIN vectors, SIN/SC negative vectors and SC negative vectors for use in accordance with the invention include vectors such as Avian Leukemia/Leukosis Viruses (ALV), for example, and without limitation, RAV-0, RAV-1, RAV-2;

Avian Sarcoma Viruses (ASV); Avian Sarcoma/Acute Leukemia Viruses (ASLV) including, without limitation, Rous Sarcoma Virus (RSV) ; Fujinami Sarcoma Viruses (FSV); Avian Myeloblastosis Viruses (AMV); Avian Erythroblastosis Viruses (AEV); Avian Myelocytomatosis Viruses (MCV), for example, and without limitation, MC29; Reticuloendotheliosis Viruses (REV), for example, and without limitation, Spleen Necrosis Virus (SNV). The invention also contemplates other useful retroviral vector, including, without limitation, retroviral vectors based upon Murine Leukemia Viruses (MLV); Molony Murine Sarcoma Viruses (MMSV); Moloney Murine Leukemia Viruses (MMLV); and lentiviruses (e.g., human immunodeficiency virus (HIV), feline immunodeficiency virus (FIV), bovine immunodeficiency virus (BIV) and simian immunodeficiency virus (SIV) which are altered to be SIN vectors, SIN/SC negative vectors or SC negative vectors as is understood by a practitioner of ordinary skill in the art.

In one very specific embodiment, a portion of the 5' LTR of a modified ALV vector disclosed in Cosset et al, J of Virology (1991) vol 65, no. 6, p 3388-3394, the disclosure of which is incorporated in its entirety herein by reference, is deleted to produce a SIN vector. In particular, nucleotides 1 to 173 were deleted from the ALV based vector LTR sequence shown in SEQ ID NO: 29. Specific deletions from 5' LTR sequences useful to produce SIN vectors from other vectors which can be used in avian transgenesis can be determined by a practitioner of ordinary skill in the art.

In one particularly useful embodiment, the invention is drawn to the production of therapeutic proteins which may be produced in the oviduct of a transgenic avian, such as a chicken, in accordance with the invention. Exemplary proteins for production in accordance with the invention include, without limitation, erythropoietin, GM-CSF, interferon β, fusion protein, CTLA4-Fc fusion protein, growth hormones, cytokines, structural proteins, interferon, lysozyme, (β-casein, albumin, α-1 antitrypsin, antithrombin III, collagen, factors VIII, IX, X (and the like), fibrinogen, lactoferrin, protein C, tissue-type plasminogen activator (tPA), somatotropin, and chymotrypsin, immunoglobulins, antibodies, immunotoxins, factor VIII, b-domain deleted factor VIII, factor VIIa, factor IX, anticoagulants; hirudin, alteplase, tpa, reteplase, tpa, tpa-3 of 5 domains deleted, insulin, insulin lispro, insulin aspart, insulin glargine, long-acting insulin analogs, glucagons, tsh, follitropin-beta, fsh, pdgh, inf-beta, inf-alpha 1, ifn-alpha 2, inf-beta, inf-beta 1b, ifn-beta 1a, ifn-gamma, ifn-gamma 1b, il-2, il-11, hbsag, ospa, dornase-alpha dnase, beta glucocerebrosidase, tnf-alpha, il-2-diptheria toxin fusion protein, tnfr-lgg fragment fusion protein laronidase, dnaases, alefacept, tositumomab, murine mab, alemtuzumab, rasburicase, agalsidase beta, teriparatide, parathyroid hormone derivatives, adalimumab (1gg1), anakinra, nesiritide, human b-type natriuretic peptide (hbnp), colony stimulating factors, pegvisomant, human growth hormone receptor antagonist, recombinant activated protein c, omalizumab, immunoglobulin e (lge) blocker, lbritumomab tiuxetan, ACTH, glucagon, somatostatin, somatotropin, thymosin, parathyroid hormone, pigmentary hormones, somatomedin, luteinizing hormone, chorionic gonadotropin, hypothalmic releasing factors, etanercept, antidiuretic hormones, prolactin and thyroid stimulating hormone, an immunoglobulin polypeptide, immunoglobulin polypeptide D region, immunoglobulin polypeptide J region, immunoglobulin polypeptide C region, immunoglobulin light chain, immunoglobulin heavy chain, an immunoglobulin heavy chain variable region, an immunoglobulin light chain variable region and a linker peptide. Production of each of these, and other, proteins is contemplated using methods, vectors and promoters of the invention.

The present invention is further illustrated by the following examples, which are provided by way of illustration and should not be construed as limiting. The contents of all references, published patents and patents cited throughout the present application are hereby incorporated by reference in their entireties.

EXAMPLE 1

Production of pALV-SIN-4.2-Lys-IFNa-2B

The vector pALV-SIN-4.2-Lys-IFNa-2B (shown in FIG. 1) was constructed and is shown in FIG. 1. The sequence of pALV-SIN-4.2-Lys-IFNa-2B is shown in SEQ ID NO: 1. The 4.2 Kb lysozyme promoter spans from nucleotides 4810 to 9008 of SEQ ID NO: 1. The lysozyme signal peptide coding sequence spans from nucleotides 9037 to 9090 of SEQ ID NO: 1. The interferon alpha 2b coding sequence spans from nucleotides 9091 to 9585 of SEQ ID NO: 1. Other components of the sequence include LTRs spanning from nucleotides 4000 to 4345 and from nucleotides 725 to 897 of SEQ ID NO: 1.

pALV-SIN-4.2-Lys-IFNa-2B can be constructed by a variety of methods which are apparent to a practitioner of skill in the art. However, the method believed to be the most useful for making the vector is as follows: A 3427 bp region of pNLB-CMV-IFN-alpha2B (disclosed in U.S. patent application Ser. No. 11/167,052, filed Jun. 24, 2005, the disclosure of which is incorporated in its entirety herein by reference) is PCR amplified using primers ATGCGCGCAT-TGGTAATTGATCGGCTGG (Primer ALV-SIN-1, SEQ ID NO: 2) and ATATGCGGCCGCGGTACCGC-CCGGGCATCGATATCAAGCTTACGGTTCACT A AAC-GAGCTCTGCTTATATAGACCTCCCA (Primer ALV-SIN-2, SEQ ID NO: 3). The product is digested with BssHII and Not I resulting in a 3428 bp fragment which can be isolated by gel purification. A 1436 bp region of pNLB-CMV-IFN-alpha2B is PCR amplified with primers ATATGCGGC-CGCGTCGACGGCCGGCCAGATCTGCTGAGCCG-GTCGCTACCA TTACCAGT (Primer ALV-SIN-3, SEQ ID NO: 4) and ATACGCGTATTCCCTAACGATCACGTCG (Primer ALV-SIN-4, SEQ ID NO: 5). The resulting product is digested with Not I and Mlu I yielding a 1438 bp fragment which is isolated by gel purification. A Bluescript II SK vector containing a BssHII stuffer fragment is digested with BssHII resulting in a linearized Bluescript vector of 2788 bp which is gel purified and then ligated to the 3428 bp and 1438 bp PCR products to yield JCR.A108.49.5.24.

JCR.A108.49.5.24 is digested with Hind III and the resulting 6823 bp fragment is circularized by ligation to yield JCR.A108.76.1.1.

A 1175 bp region of JCR.A108.76.1.1 is PCR amplified with primers CTGAAGTGTAAGGAATGTAAG (Primer ALV-SIN-5, SEQ ID NO: 6) and GCGCGTCTCATC-CCCCTCCCTATGCAAAAG (Primer ALV-SIN-6, SEQ ID NO: 7) and the resulting fragment is digested with Blp I and Esp3I producing a 1030 by fragment which is isolated by gel purification. A 660 bp region of JCR.A108.76.1.1 is PCR amplified with primers GGGCGTCTCAGGGACGGATTG-GACGAACCACTGAATT (Primer ALV-SIN-7, SEQ ID NO: 8) and TTAGTGCTTTACGGCACCTC (Primer ALV-SIN-8, SEQ ID NO: 9) and digested with Esp3I and DraIII resulting in a 596 bp fragment which is isolated by gel purification. JCR.A108.76.1.1 is digested with DraIII and Blp I and the 5024 bp linear vector is ligated to the 1030 and 596 bp PCR fragments to produce pALV-SIN.

pALV-SIN is digested with BamHI and the 4795 bp linear vector is isolated by gel purification. A 4815 bp region of JCR.115.93.1.2 (disclosed in US patent application No. 2007/0124829, filed Jan. 26, 2007,) is PCR amplified with primers GACGGATCCGATACCGTCCCTATTTTTGT-GTTTGCTTC (Primer ALV-SIN-9, SEQ ID NO: 10) and TAACGGATCCTAGACTTTTTACTCCTTAGA (Primer ALV-SIN-10, SEQ ID NO: 11) and is digested with BamHI. The resulting 4802 fragment is ligated to the 4795 bp linear pALV-S1N to produce pALV-SIN-4.0-Lys-IFNa-2B.

EXAMPLE 2

Production of Transgenic Quail Using pALV-SIN-4.2-Lys-IFNa-2B

Transduction particles of the vector pALV-SIN-4.2-Lys-IFNa-2B were produced in fibroblast cells as disclosed in US patent publication No. 2007/0077650, published Apr. 5, 2007, entitled: Rapid Production of High Titer Virus, the disclosure of which is incorporated in its entirety herein by reference.

Fertilized Japanese quail eggs were windowed essentially according to the Speksnijder procedure disclosed in U.S. Pat. No. 5,897,998, the disclosure of which is incorporated in its entirety herein by reference. Eighty eggs were injected in the subgerminal cavity with about 7 microliters (approximately $7 \times 10^4$ viral particles total) of pALV-SIN-4.2-Lys-IFNa-2B transducing particles per egg. Since no selectable marker is used in pALV-SIN-4.2-Lys-IFNa-2B, the concentration of viral particles is estimated based upon past results for viral particle production where a selectable cassette or marker was used in the vector which allowed for particle quantification. Sixteen chicks hatched about 18 days after injection and human IFN levels were measured by IFN ELISA from serum samples collected from chicks 12 weeks after hatch. None were positive for the IFN protein in the serum.

In order to identify G0 quail which contained the interferon alpha 2 coding sequence containing transgene in their genome, DNA was extracted from blood of the birds and the DNA samples were subjected to Taqman® analysis on a 7700 Sequence Detector (Perkin Elmer).

Figure 2:
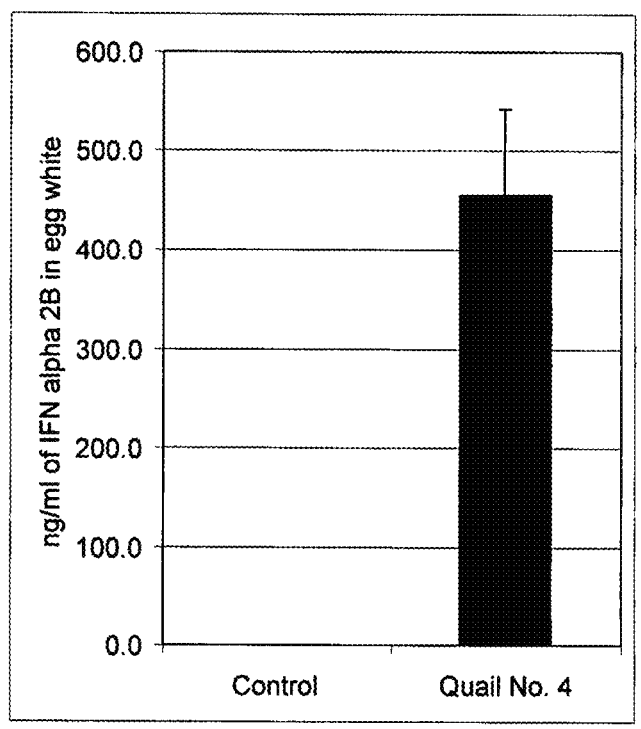
FIG. 2 is a bar graph illustrating expression levels of IFNa in the egg white of a transgenic quail. G0 quail was produced by injection of pALV-SIN-4.0-Lys-IFNa-2B retroviral vector transduction particles into Japanese quail embryos.

Eggs from eight G0 quail were tested for the presence of the IFN protein in the egg white by ELISA. Quail No. 4 was found to have significant levels of IFN in egg white from her eggs. FIG. 2 shows a bar graph illustrating expression levels of IFN in the egg white of Quail No. 4. Quail No. 4 expressed IFN-alpha-2 at 0.45 µg/ml of egg white, which is a high level of expression for a G0 avian. There was no interferon alpha 2 detected in the blood of Quail No. 4 which is particularly significant. For example, in certain instances the recombinant protein may be harmful to the development or health of the avian when present in the blood which can kill the bird or can lead to reduced levels of protein production.

EXAMPLE 3

Production of Transgenic Quail Using pALV-SIN-6.5-Lys-IFNa-2B

The 4.2 kb lysozyme promoter of vector pALV-SIN-4.2-Lys-IFNa-2B is removed and replaced with a 6.5 kb lysozyme promoter corresponding to about nucleotides 5363 to 11863 of SEQ ID NO: 12, using standard methodologies known to practitioners of skill in the art, resulting in pALV-SIN-6.5-Lys-IFNa-2B. Transduction particles of the new vector pALV-SIN-6.5-Lys-IFNa-2B are produced as disclosed in US patent publication No. 2007/0077650, published Apr. 5, 2007.

Fertilized chicken eggs or Japanese quail eggs are windowed and about $7 \times 10^4$ pALV-SIN-6.5-Lys-IFNa-2B transducing particles are injected into the subgerminal cavity of each egg. Eggs hatch 21 or 18 days after injection and chimeric birds are identified that contain the active transgene in their genome, as described in Example 2. Fully transgenic 01 birds which contain the transgene in their genome are produced from chimeras using methods known in the art, i.e., crossing male chimeras with non-transgenic females.

EXAMPLE 4

Production of Vector pSIN-OV-3.5-I-CTLA4-Fc-Inv

This vector includes the ovalbumin Dnase hypersensitive sites (DHS) I, II and III, the first exon (exon L), the first intron and the CTLA4-Fc fusion protein coding sequence inserted in frame with the ATG of second exon (exon 1) and with the 3' untranslated region (UTR). The expression cassette is inserted in the inverse orientation into an avian leukosis virus (ALV) vector, which was made self-inactivating (SIN) by deletion of nucleotides 1 to 173 of the ALV LTR sequence shown in SEQ ID NO: 29.

The vector was constructed as follows: pNLB-3.9-OM-CTLA4-Fc, disclosed in Example 20 of US patent publication No. 2007/0113299, published May 17, 2007, the disclosure of which is incorporated in its entirety herein by reference, was cut with Nae I and Not I. The Not I site was filled in by Klenow reaction. The resulting 8125 by fragment was gel purified, religated, producing pOM-3.9-CTLA4-dSacI.

pOM-3.9-CTLA4-dSacl was cut with EcoRI and Kpn I and the 8115 bp fragment gel purified. The 3' UTR of the chicken ovalbumin gene was PCRed from BAC 26, disclosed in US patent publication No. 2006/0130170, published Jun. 15, 2006, with the primers 5'-GCGGAAT-TCAAAGAAGAAAGCTGAAAAAC-3' (SEQ ID NO: 13) and 5'-GCGGGTACCTTCAAATACTACAAGTGAAA-3' (SEQ ID NO: 14). The 3' UTR PCR was cut with Eco RI and Kpn I and the 684 bp fragment gel purified. The 8115 bp fragment of pOM-3.9-CTLA4-dSacI was ligated to the 684 bp fragment of 3' UTR PCR, producing pOM-3.9-CTLA4-OV3'UTR.

The 3.5 kb OV promoter region, exon L, first intron and the UTR of exon 1 was PCR amplified with BAC26 as a template and with primers 5'-GGCCTCGAGTCAAGTTCT-GAGTAGGTTTTAGTG-3' (SEQ ID NO: 15) and 5'-GCGCGTCTCTGTCTAGAGCAAACAGCAGAACA-GTGAAAATG-3' (SEQ ID NO: 16). The PCR product was cut with Xho I and Esp3I and the 5094 bp product was gel purified.

Figure 3:
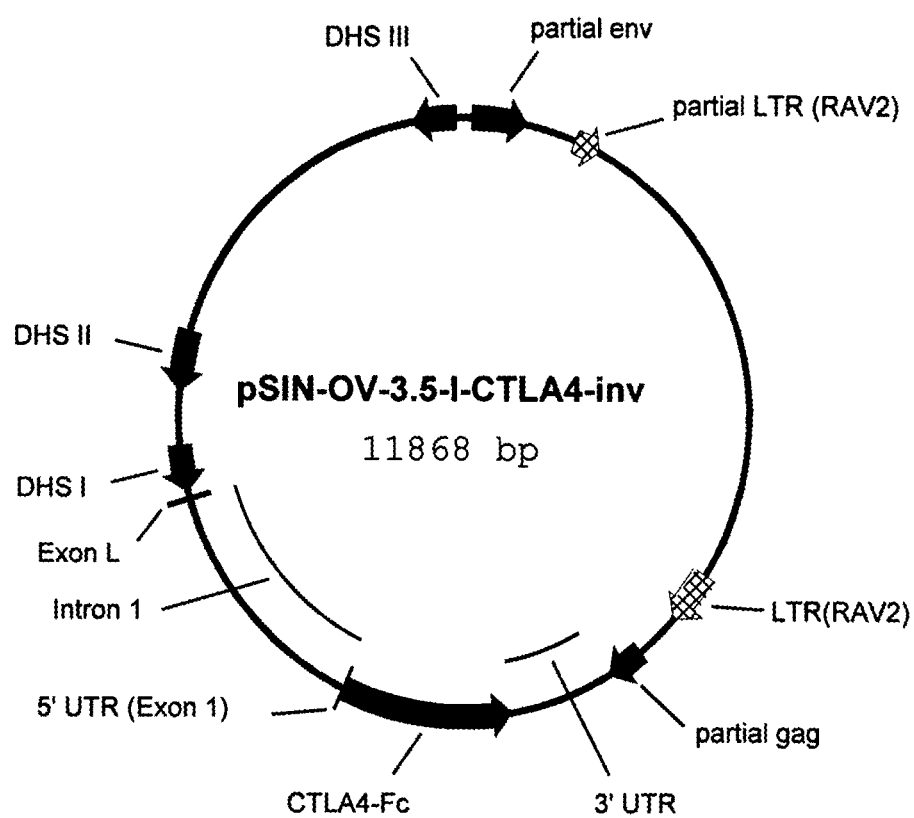
FIG. 3 shows a circular map of the pSIN-OV-3.5-I-CTLA4-inv vector. The nucleotide sequence of pSIN-OV-3.5-I-CTLA4-inv is shown in SEQ ID NO: 19.

A 5' portion of the CTLA4-Fc gene was PCR amplified using pOM-3.9-CTLA4 as a template and primers 5'-GCGCGTCTCAAGACAACTCAGAGTTCAC-CATGGGTGTACTGCTCACACAG-3' (SEQ ID NO: 17) and 5'-GGCCCGGGAGTTTTGTCAGAAGATTTGGG-3' (SEQ ID NO: 18). The PCR product was cut with Esp3I and SacI and the 384 bp product gel purified.

pOM-3.9-CTLA4-OV3'UTR was cut with Sac I and Xho I, the 4473 bp product gel purified and ligated to the 5094 bp OV PCR fragment and 384 bp CTLA4-Fc fragment, producing pOV-3.5-I-CTLA4.

pALV-SIN, disclosed, for example, in Example 10 of parent case US patent publication No. 2007/0124829, published May 31, 2007, was cut with Mfe I and Xho I, filled in with Klenow and the 4911 bp fragment gel purified.

pOV-3.5-I-CTLA4 was cut with XhoI and BamHI, filled in with Klenow and the 6957 bp fragment gel purified. This fragment was ligated into the 4911 bp fragment of pAVI-SIN such that the CTLA4-Fc gene and flanking expression elements are in the opposite orientation of the ALV long terminal repeats, producing pSIN-OV-3.5-I-CTLA4-inv. See FIG. 3 and SEQ ID NO: 19. Such opposite orientation may be preferred if the coding sequence of interest (i.e., CSI) in the transgene contains one or more introns or splice sites.

EXAMPLE 5

Production of Transgenic Quail Using SIN-OV-3.5-I-CTLA4-inv

Retroviral particles containing the pSIN-OV-3.5-I-CTLA4-inv vector (FIG. 3) and pseudotyped with the VSV envelope protein were produced as described in US patent publication No. 2007/0077650, published Apr. 5, 2007. Virus particles were harvested at 48 hours post-transfection, concentrated and on the same day, approximately 4 microliters of the virus suspension containing about $1 \times 10^5$ particles was injected into the subgerminal cavity of stage X quail eggs. Eggs were resealed and hatched.

ALV has a CTE element in the 3' end of its genome that allows transport of unspliced retroviral RNA to the cytoplasm. In pSIN-OV-3.5-I-CTLA4-inv, due to the inverse orientation of the OV promoter relative to the LTRs, the CTE is upstream of the OV promoter such that the CTE element is only in RNAs derived from the 5' LTR promoter and not in RNAs transcribed by the OV promoter. Therefore, any RNA transcribed by the OV promoter should be spliced prior to being transported into the cytoplasm.

Egg whites from chimeric quail were assayed using an ELISA for CTLA4-Fc. One quail was found to have CTLA4-Fc in her egg white at approximately 16 μg/ml. The transgenesis level in these quail is estimated at about 5% or less. Thus the level in a G1 should be substantially greater. It is expected that similar levels would be seen in a chicken and other avians, as the quail and chicken ovalbumin genes, as well as ovalbumin genes of other avians, are very similar.

EXAMPLE 6

Construction of pSIN-3.9-OM-CTLA4-Fc

Figure 4:
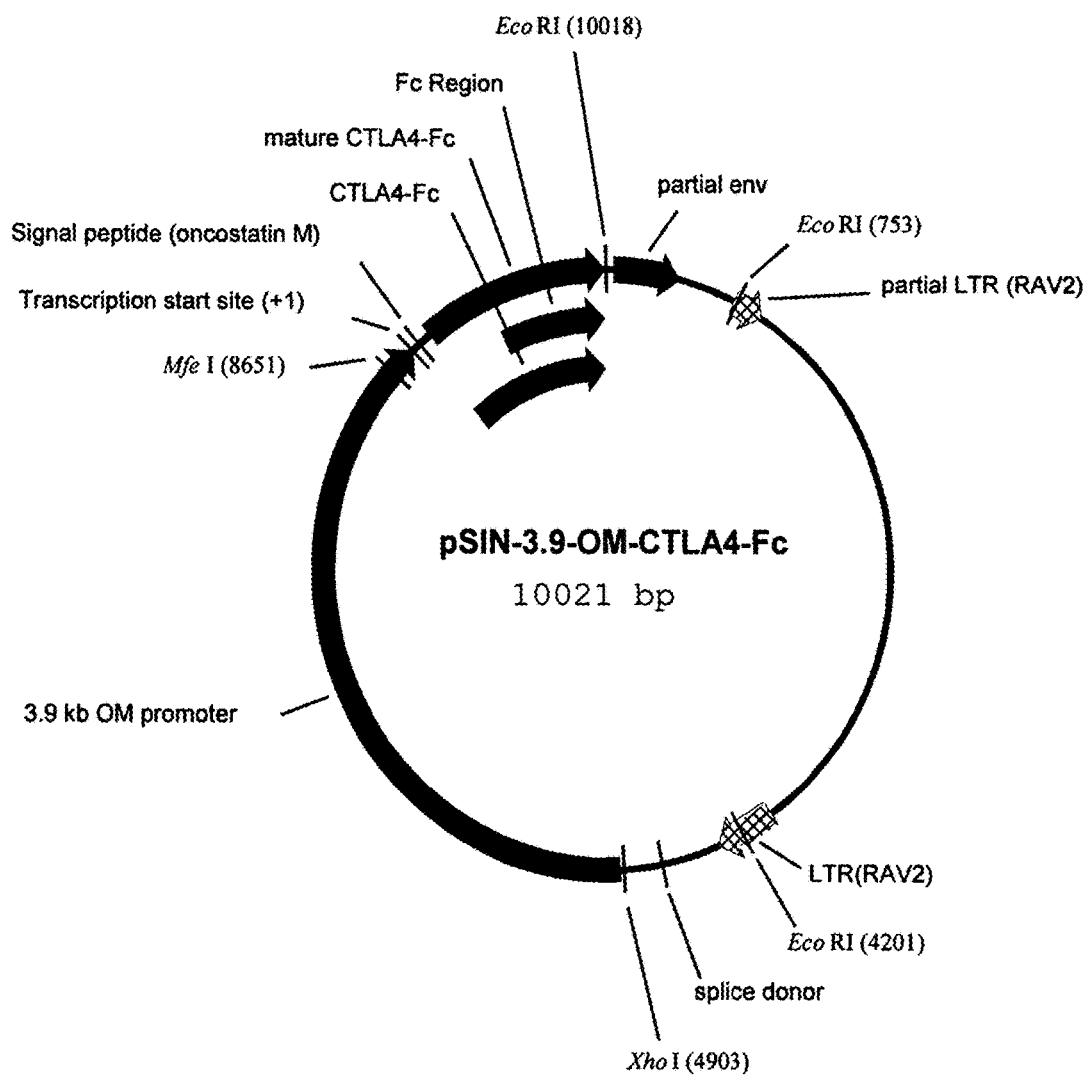
FIG. 4 shows a circular map of the pSIN-3.9-OM-CTLA4-Fc vector. The nucleotide sequence of pSIN-3.9-OM-CTLA4-Fc is shown in SEQ ID NO: 20.

The 4907 bp Mfe I/Xho I fragment of pALV-SIN (disclosed, for example, in US patent publication No. 2007/0124829, published May 31, 2007) was ligated to the 5115 XhoI/EcoRI fragment of pOM-3.9-CTLA4 (shown in FIG. 15 of US patent publication No. 2007/0113299, published May 17, 2007), producing pSIN-3.9-OM-CTLA4-Fc Shown in FIG. 4 and SEQ ID NO: 20,

EXAMPLE 7

Production of Transgenic Chickens Using pSIN-3.9-OM-CTLA4-Fc

Retroviral particles pseudotyped with the VSV envelope protein and containing the pSIN-3.9-OM-CTLA4-Fc (FIG. 4) vector were produced as described in US patent publication No. 2007/0077650, published Apr. 5, 2007. Virus was harvested at 48 hours post-transfection, concentrated and on the same day approximately 7 microliters injected into the subgerminal cavity of stage X eggs. Eggs were resealed and incubated until hatch.

Egg white from hens was assayed using an ELISA for CTLA4-Fc. One hen was found to have CTLA4-Fc in her egg white at approximately 0.37 μg/ml. The transgenesis level in these hens is estimated at 5% or less. Thus the levels in a G1 should be substantially greater.

Any useful coding sequence may be inserted in place of the CTLA4-Fc coding sequence for production of the corresponding product.

EXAMPLE 8

Construction of pSIN-1.8-OM-IFNa-2B

Figure 5:
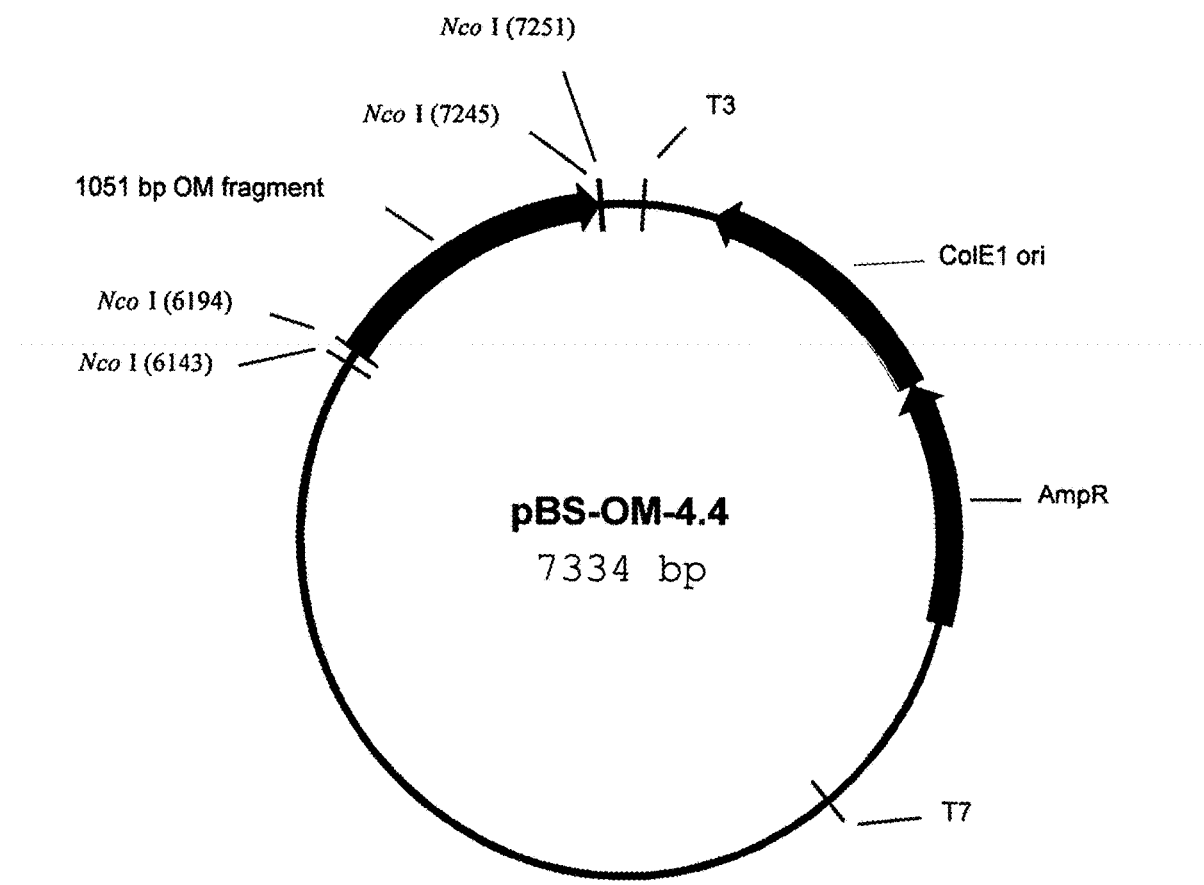
FIG. 5 shows a circular map of the pBS-OM-4.4 vector. The nucleotide sequence of pBS-OM-4.4 is shown in SEQ ID NO: 23.
Figure 6:
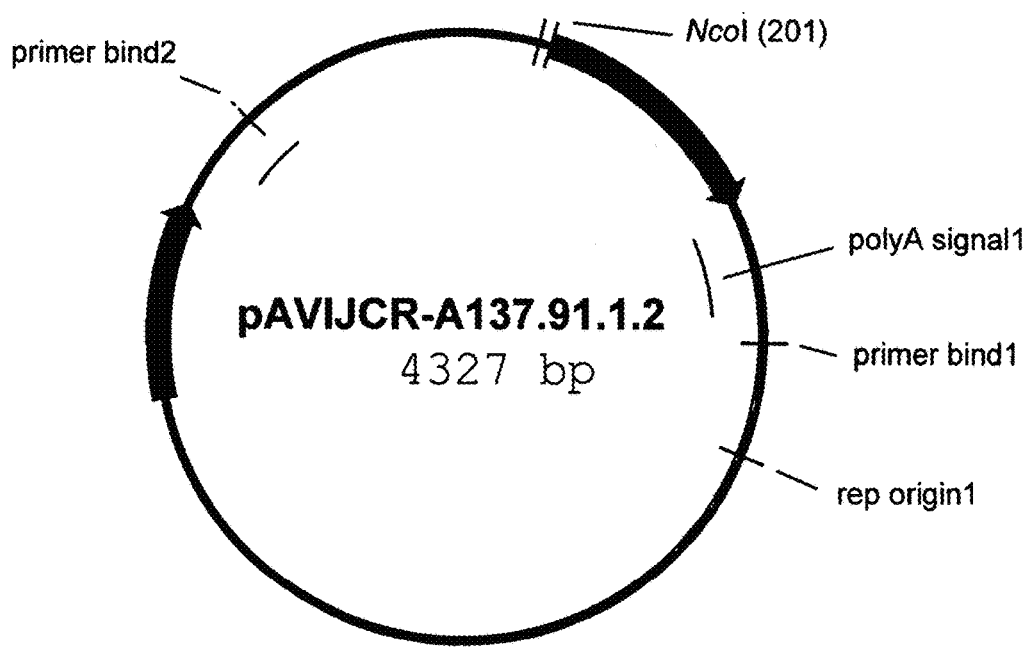
FIG. 6 shows a circular map of the pAVIJCR-A137.91.1.2 vector. The nucleotide sequence of pAVIJCR-A137.91.1.2 is shown in SEQ ID NO: 24.

The 1051 bp Nco I-Nco I fragment from pBS-OM-4.4 (FIG. 5 SEQ ID NO: 23) was inserted into the Nco I site of pAVIJCR-A137.91.1.2 (FIG. 6 SEQ ID NO: 24), thereby inserting the 1 kb ovomucoid promoter in front of an IFN coding sequence and SV40 polyadenylation signal and producing plkb-OM-IFNMM. A 1816 bp Cla I-Sac I fragment of plkb-OM-IFNMM was inserted into the 6245 bp Cla I-Sac I fragment of pBS-OM-4.4, thereby fusing the 4.4 kb ovomucoid fragment with the IFN coding sequence and producing p4.4OM-IFNMM. The 8511 bp BamH I-Sal I fragment of pBS-OMUP-10 was ligated to the 5148 bp BamH I-Sal I fragment of p4.4OM-IFN, thereby placing the 10 kb ovomucoid promoter in front of the IFN coding sequence, producing p10-OM-IFN.

Figure 7:
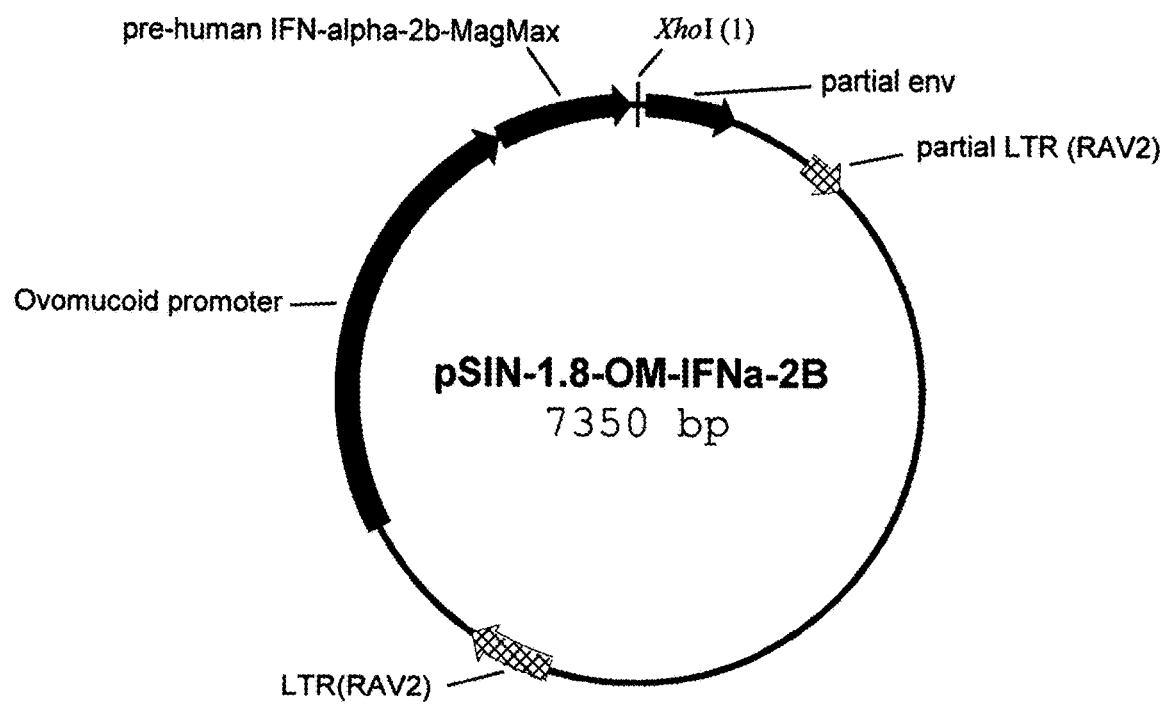
FIG. 7 shows a circular map of the pSIN-1.8-OM-IFNa-2B plasmid vector. The nucleotide sequence of pSIN-1.8-OM-IFNa-2B is shown in SEQ ID NO: 21.

Region 2487-4889 of p10.0-OM-IFN was PCR amplified with primers 5'-GGCGTCGACGGATCCGTTAACCCTA-GAACTAGTGGATCTCTGCCCTTGTGC TGAC-3' (SEQ ID NO: 27) and 5'-GGCCTCGAGCCTAGACTTTT-TACTCCTTAGA-3' (SEQ ID NO: 28). The PCR product was digested with Sal I and Xho I and the 2435 bp isolated. pALV-SIN (disclosed, for example, in US patent publication No. 2007/0124829, published May 31, 2007) was digested with Xho I and the 4915 bp fragment isolated and ligated to the 2435 bp fragment, producing pSIN-1.8-OM-IFNa-2B, shown in FIG. 7 and SEQ ID NO: 21.

EXAMPLE 9

Production of Transgenic Chickens Using pSIN-1.8-OM-IFNa-2B

Retroviral particles having the pSIN-1.8-OM-IFNa-2B transgene and pseudotyped with the VSV envelope protein were produced as described in US patent publication No. 2007/0077650, published Apr. 5, 2007. Virus was harvested at 48 hours post-transfection, concentrated and, on the same day, approximately 7 microliters injected into the subgerminal cavity of stage X eggs. Eggs were resealed and incubated until hatch.

Egg whites from hens were assayed using an ELISA for IFNa-2B. Hens were found to have IFNa-2B in egg white at levels that ranged from 1.5 to 865.0 ng/ml with IFNa-2B levels at least about 600 fold lower in the serum. The transgenesis level in these hens is estimated at 5% or less.

Five G0 sperm positive roosters were bred to non-transgenic hens. Of 1251 offspring, 30 carried the pSIN-1.8-OM-IFNa-2B transgene. Six of the 30 hens expressed human IFN-α-2B at 34.1 to 165.6 μg/ml of egg white. Each of the six hens had a single copy of the transgene. Serum levels of human IFN-α-2B were 0.3 to 9.2 ng/ml which, on average, was 30,000 fold lower than egg white levels.

EXAMPLE 10

Production of Transgenic Chickens Using Lentivirus Vectors And Moloney Murine Leukemia Virus The invention specifically contemplates the employment of other retroviral vectors that are useful in avian transgenesis to be used in accordance with the present invention. Such vectors can be employed to produce transgenic avians, for example, in the same way as ALV-SIN vectors have been used in Examples 1 to 9 above. For example, Moloney Murine Leukemia Virus (MMLV) and Lentiviral Vectors can be used in accordance with the invention, each, for example, by deleting one or more of the CAAT box; the TAATA box; and enhancer contained in the U3 region of the upstream LTR of each virus to produce a SIN vector. Alternatively, or in addition (i.e., in conjunction with a SIN vector) no transcriptionally active markers or selectable cassettes are included in each of the retroviral vectors.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

What is claimed is:

1. A method of using a transgenic chicken to produce an exogenous protein comprising:
   providing a transgenic chicken whose genome comprises a self-inactivating avian leukosis viral (ALV) vector encoding an exogenous protein operably linked to a promoter;
   obtaining a hard shell egg containing the exogenous protein from the transgenic chicken,
   wherein the promoter comprises a nucleic acid sequence that is at least 90% identical to a nucleic acid molecule comprising from 5' to 3':
   i) an ovalbumin Dnase hypersensitive site (DNS) III consisting of nucleotides 3253-3559 of SEQ ID NO: 22;
   ii) an ovalbumin DNS II consisting of nucleotides 5629-6009 of SEQ ID NO: 22;
   iii) an ovalbumin DNS I consisting of nucleotides 6359-6659 of SEQ ID NO: 22;
   iv) a 5' UTR-5' portion from Exon L consisting of nucleotides 6659-6705 of SEQ ID NO: 22;
   v) intron A consisting of nucleotides 6706-8294 of SEQ ID NO: 22;
   vi) a 5' UTR-3' portion from Exon I consisting of nucleotides 8295-8311 of SEQ ID NO: 22;
   vii) a 3' UTR.

2. The method of claim 1, wherein the exogenous protein is a human protein.

3. The method of claim 1, wherein the exogenous protein is a therapeutic protein.

4. The method of claim 1 wherein the exogenous protein is selected from the group consisting of erythropoietin, GM-C SF, interferon, fusion protein, CTLA4-Fc fusion protein, growth hormones, cytokines, structural, interferon, lysozyme, β-casein, albumin, α-1 antitrypsin, antithrombin III, collagen, factors VIII, IX, X (and the like), fibrinogen, lactoferrin, protein C, tissue-type plasminogen activator (tPA), somatotropin, chymotrypsin, immunoglobulins, antibodies, immunotoxins, factor VIII, b-domain deleted factor VIII, factor VIIa, factor IX, anticoagulants; hirudin, alteplase, reteplase, tPA- 3 of 5 domains deleted, insulin, insulin lispro, insulin aspart, insulin glargine, long-acting insulin analogs, glucagons, thyroid-stimulating hormone (tsh), follitropin-beta, follicle-stimulating hormone (fsh), pdgh, inf-beta, inf-alpha 1, ifn-alpha 2, inf-beta, inf-beta 1b, ifn-beta 1a, ifn-gamma, ifn-gamma 1b, il-2, il-11, HBsAg, dornase-alpha dnase, beta glucocerebrosidase, tnf-alpha, il-2-diptheria toxin fusion protein, tnfr-lgg fragment fusion protein laronidase, DNAses, alefacept, tositumomab, murine mab, alemtuzumab, rasburicase, agalsidase beta, teriparatide, parathyroid hormone derivatives, adalimumab (lgg1), anakinra, biological modifier, nesiritide, human b-type natriuretic peptide (hbnp), colony stimulating factors, pegvisomant, human growth hormone receptor antagonist, recombinant activated protein c, omalizumab, immunoglobulin E blocker, lbritumomab tiuxetan, ACTH, glucagon, somatostatin, somatotropin, thymosin, parathyroid hormone, pigmentary hormones, somatomedin, luteinizing hormone, chorionic gonadotropin, hypothalmic releasing factors, etanercept, antidiuretic hormones, prolactin, thyroid stimulating hormone, human immunoglobulin polypeptide D region, human immunoglobulin polypeptide J region, human immunoglobulin polypeptide C region, human immunoglobulin light chain, human immunoglobulin heavy chain, an human immunoglobulin heavy chain variable region, and an immunoglobulin light chain variable region.

5. The method of claim 1 further comprising isolating said protein.

* * * * *

UNITED STATES PATENT AND TRADEMARK OFFICE
CERTIFICATE OF CORRECTION

PATENT NO. : 10,182,561 B2  
APPLICATION NO. : 15/181987  
DATED : January 22, 2019  
INVENTOR(S) : Harvey et al.

Page 1 of 1

It is certified that error appears in the above-identified patent and that said Letters Patent is hereby corrected as shown below:

In the Claims

Column 99, Line 60, "GM-C SF" should read --GM-CSF--

Signed and Sealed this  
Third Day of September, 2019

Andrei Iancu  
*Director of the United States Patent and Trademark Office*